(12) United States Patent
Meng et al.

(10) Patent No.: US 9,249,192 B2
(45) Date of Patent: Feb. 2, 2016

(54) INFECTIOUS GENOMIC DNA CLONE AND SEROLOGICAL PROFILE OF TORQUE TENO SUS VIRUS 1 AND 2

(71) Applicant: Virginia Tech Intellectual Properties, Inc., Blacksburg, VA (US)

(72) Inventors: Xiang-Jin Meng, Blacksburg, VA (US); Yaowei Huang, Blacksbur

(56) References Cited

OTHER PUBLICATIONS

Kakkola, L., et al., "Expression of all six human Torque teno virus (TTV) proteins in bacteria and in insect cells, and analysis of their IgG responses" Virology 382, pp. 182-189, 2008.

Ott, C., et al., "Use of a TT virus ORF1 recombinant protein to detect anti-TT virus antibodies in human sera," J Gen Virol 81, pp. 2949-2958, 2000.

Ellis, et al., "Effect of coinfection with genogroup 1 porcine torque teno virus on porcine circovirus type 2-associated postweaning multisystemic wasting syndrome in gnotobiotic pigs". American Journal of Veterinary Research, Dec. 2008, pp. 1608-1614, vol. 69, Issue 12, Schaumburg, IL.

Aramouni, M., et al., "Torque teno sus virus 1 and 2 viral loads in postweaning multisystemic wasting syndrome (PMWS) and porcine dermatitis and nephropathy syndrome (PDNS) affected pigs, Vet Microbiol 153, pp. 377-381, 2011.

Gauger, P. C., et al., "Postweaning multisystemic wasting syndrome produced in gnotobiotic pigs following exposure to various amounts of porcine circovirus type 2a or type 2b," Vet Microbiol 153, pp. 229-239, 2011.

Huang, Y. W., et al., "Serological profile of Torque teno sus virus species 1 (TTSuV1) in pigs and antigenic relationships between two TTSuV1 genotypes (1a and 1b), between two species (TTSuV1 and 2), and between porcine and human anelloviruses," J. Virol., Submitted Manuscript, 2012.

Lee, S. S., et al. "Quantitative detection of porcine Torque teno virus in Porcine circovirus-2-negative and Porcine circovirus-associated disease-affected pigs," J Vet Diagn Invest 22, pp. 261-264, 2010.

Ninomiya, M., et al., "Development of PCR assays with nested primers specific for differential detection of three human anelloviruses and early acquisition of dual or triple infection during infancy." J Clin Microbiol 46, pp. 507-514, 2008.

De Villiers, E. M., et al., "The diversity of torque teno viruses: in vitro replication leads to the formation of additional replication-competent subviral molecules," J Virol 85, pp. 7284-7295, 2011.

Kakkola, L., et al., "Construction and biological activity of a full-length molecular clone of human Torque teno virus (TTN) genotype6," FEBS J 274, pp. 4719-4730, 2007.

Leppik, L., et al., "In vivo and in vitro intragenomic rearrangement of TT viruses," J Virol 81, pp. 9346-9356, 2007.

Ball, J.K., et al., "TT virus sequence heterogeneity in vivo: evidence for co-infection with multiple genetic types," J Gen Virol 80, Pt 7, pp. 1759-1768, 1999.

Forns, X., et al., "High prevalence of TT virus (TTV) infection in patients on maintenance hemodialysis: frequent mixed infections with different genotypes and lack of evidence of associated liver disease," J Med Virol 59, pp. 313-317, 1999.

Pesch, W., et al., "Porcine Torque teno virus: determination of viral genomic loads by genogroup-specific multiplex rt-PCR, detection of frequent multiple infections with genogroups 1 or 2, and establishment of viral full-length sequences," Vet Microbiol 143, pp. 202-212, 2010.

Finsterbusch, et al., "Gene expression of the human Torque Teno Virus isolate P/1C1," Virology 381, pp. 36-45, 2008.

Teixeira, T. F., et al., "Torque teno sus virus (TTSuV) in cell cultures and trypsin," PLoS One 6:e17501, 2011.

Beach, N. M., et al., "Productive infection of human hepatocellular carcinoma cells by porcine circovirus type 1," Vaccine 29, pp. 7303-7306, 2011.

Hattermann, K., et al., "Infection studies on human cell lines with porcine circovirus type 1 and porcine circovirus type 2," Xenotransplantation 11, pp. 284-294, 2004.

Ma, H., et al., "Investigations of porcine circovirus type 1 (PCV1) in vaccine-related and other cell lines," Vaccine 29, pp. 8429-8437, 2011.

Tischer, I., et al., "A very small porcine virus with circular single-stranded DNA," Nature 295, pp. 64-66, 1982.

Kekarainen, T., et al. "Swine torque teno virus detection in pig commercial vaccines, enzymes for laboratory use and human drugs containing components of porcine origin," J Gen Virol 90, pp. 648-653, 2009.

Mueller, B., et al., "Gene expression of the human Torque Teno Virus isolate P/1C1," Virology 381, pp. 36-45, 2008.

Martinez-Guino, L., et al., "Expression profile and subcellular localization of Torque teno sus virus proteins," J Gen Virol 92, pp. 2446-2457, 2011.

Miyata, H., et al. "Identification of a novel GC-rich 113-nucleotide region to complete the circular, single-stranded DNA genome of TT virus, the first human circovirus," J Virol 73, pp. 3582-3586, 1999.

Okamoto, H., et al., "The entire nucleotide sequence of a TT virus isolate from the United States (TUS01): comparison with reported isolates and phylogenetic analysis," Virology 259, pp. 437-448, 1999.

Huang, Y. W., et al., "Development of SYBR green-based real-time PCR and duplex nested PCR assays for quantitation and differential detection of species- or type-specific porcine Torque teno viruses," J Virol Methods 170, pp. 140-146, 2010.

Crowther, R. A., et al., "Comparison of the structures of three circoviruses: chicken anemia virus, porcine circovirus type 2, and beak and feather disease virus," J Virol 77, pp. 13036-13041, 2003.

Handa, A., et al. "Prevalence of the newly described human circovirus, TTV, in United States blood donors," Transfusion 40, pp. 245-251, 2000.

Zoller et al., DNA 3, pp. 479-488, 1984.

Fenaux, M., et al., "A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs," J Virol 78, pp. 6297-6303, 2004.

Halbur, P. G., et al. "Comparison of the pathogenicity of two US porcine reproductive and respiratory syndrome virus isolates with that of the Lelystad virus," Vet Pathol 32, pp. 648-660, 1995.

Ritterbusch, G.A., et al. "Natural Co-Infection of Torque Teno Virus and Porcine Circovirus 2 in the Reproductive Apparatus of Swine," Res. Vet Sci., 2011.

Huang, Y.W., et al., "Rescue of a Porcine Anellovirus (Torque teno sus virus 2) from Cloned Genomic DNA in Pigs," J. Virol. Submitted Manuscript, 2012.

O'Reilly et al., "Baculovirus Expression Vectors: A Lab Manual," Freeman & Co., 1995.

Schierack, P., "Characterization of a Porcine Intestinal Epithelial Cell Line for In Vitro Studies of Microbial Pathogenesis in Swine," Histochem. Cell Biology 125, pp. 293-305, 2006.

Emerson, S.U., et al. "In Vitro Replication of Hepatitis E Virus (HEV) Genomes and of an HEV Replicon Expressing Green Fluorescent Protein," J. Virol. 78, pp. 4838-4846, 2004.

Buck, C.B. et al., "Efficient Intracellular Assembly of Papillomaviral Vectors," J. Virol. 78, pp. 751-757, 2004.

Anderson, et al., "Failure to genotype herpes simplex virus by real-time PCR assay and melting curve analysis due to sequence variation within probe binding sites". Journal of Clinical Microbiology, 2003, pp. 2135-2137 vol. 41, American Society for Microbiology.

Bao, et al., "Virus Classification by Pairwise Sequence Comparison (PASC)", 2008, pp. 342-348, vol. 5, Elsevier Ltd. Oxford, U.K.

Biagini, et al., "Classification of TTV and related viruses (anelloviruses)". Current Topics in Microbiology Immunology, 2009, pp. 21-33, vol. No. 331, Springer-Verlag Berlin Heidelberg.

Biagini, et al., "Distribution and genetic analysis of TTV and TTMV major phylogenetic groups in French blood donors". Journal of Medical Virology, 2006, pp. 298-304, vol. No. 78, Issue No. 2, Journal of Medical Virology, Marseille, France.

Biagini, et al., "Circular genomes related to anelloviruses identified in human and animal samples by using a combined rolling-circle amplification/sequence-independent single primer amplification approach". Journal of General Virology, 2007, pp. 2696-2701, vol. 88, Pt 10, Marseille, France.

Brassard, et al., "Development of a real-time TaqMan PCR assay for the detection of porcine and bovine Torque teno virus", Journal of Applied Microbiology, Agriculture and Agri-food Canada, Nov. 2009, pp. 2191-2198, Food Research and Development Centre, Saint-Hyacinthe, QC, Canada.

(56) References Cited

OTHER PUBLICATIONS

Davidson, et al., "Unraveling the puzzle of human anellovirus infections by comparison with avian infections with the chicken anemia virus", Virus Research, 2008, pp. 1-15, vol. 137, Issue 1, Israel.
De Smit, et al., "Apoptosis-inducing proteins in chicken anemia virus and TT virus". Current Topics in Microbiology and Immunology, 2009, pp. 131-149, vol. 331.
Gallei, et al., "Porcine Torque teno virus: Determination of viral genomic loads by genogroup-specific multiplex rt-PCR, detection of frequent multiple infections with genogroups 1 or 2, and establishment of viral full-length sequences". Veterinary Microbiology, 2010, pp. 202-212, vol. 143, Veterinary Microbiology, Munster, Germany.
Gibellini, et al., "Simultaneous detection of HCV and HIV-1 by SYBR Green real time multiplex RT-PCR technique in plasma samples". Molecular and Cellular Probes, Mar. 2006, pp. 223-229, vol. 20.
Hino, et al., "Torque teno virus (TTV): current status". Reviews in Medical Virology, 2007, pp. 45-57, vol. 17, Wiley Interscience.
Hino, et al., "Relationship of Torque teno virus to chicken anemia virus". Current Topics in Microbiology and Immunology, 2009, pp. 117-130, vol. 331, Springer Verlag Berlin Heidelberg.
Ilyina, et al., "Conserved sequence motifs in the initiator proteins for rolling circle DNA replication encoded by diverse replicons from eubacteria, eucaryotes and archaebacteria". Nucleic Acids Research, pp. 3279-3285, vol. 20, No. 13, NIH, Bethesda, MD.
Huang, Y.W. et al., Multiple infection of porcine Torque teno virus in a single pig and characterization of the full-length genomic sequences of four U.S. prototype PTTV strains: Implication for genotyping of PTTV, Nov. 2009, p. 289-297, Virology, vol. 396.
Inami, et al., "Full-length nucleotide sequence of a simian TT virus isolate obtained from a chimpanzee: evidence for a new TT virus-like species". Virology, 2000, pp. 330-335, vol. 277, No. 2, Academic Press.
Jelcic, et al., "Isolation of multiple TT virus genotypes from spleen biopsy tissue from a Hodgkin's disease patient: genome reorganization and diversity in the hypervariable region". Journal of Virology, 2004, pp. 7498-7507, vol. 78, No. 14, American Society for Microbiology.
Kakkola, et al., "Replication of and protein synthesis by TT viruses". Current Topics in Microbiology and Immunology, 2009, pp. 53-64, vol. 331, Springer Verlag Berlin Heidelberg.
Kekarainen, et al., "Detection of swine Torque teno virus genogroups 1 and 2 in boar sera and semen". Theriogenology, 2007, pp. 966-971, vol. 68, No. 7.
Kekarainen, et al., "Prevalence of swine Torque teno virus in post-weaning multisystemic wasting syndrome (PMWS)-affected and non-PMWS-affected pigs in Spain". Journal of General Virology, 2006, pp. 833-837, vol. 87, Part 4, UK.
Krakowka, et al., "Evaluation of the effects of porcine genogroup 1 torque teno virus in gnotobiotic swine". American Journal of Veterinary Research, 2008, pp. 1623-1629, vol. 69.
Krakowka, et al., "Evaluation of induction of porcine dermatitis and nephropathy syndrome in gnotobiotic pigs with negative results for porcine circovirus type 2". American Journal of Veterinary Research, 2008, pp. 1615-1622, vol. 69, Part 12.
Maggi, et al., "Immunobiology of the Torque teno viruses and other anelloviruses". Current Topics in Microbiology and Immunology, 2009, pp. 65-90, vol. 331.
Martinez, "Simultaneous detection and genotyping of porcine reproductive and respiratory syndrome virus (PRRSV) by real-time RT-PCR and amplicon melting curve analysis using SYBR Green". Research in Veterinary Science, 2008, pp. 184-193 vol. 85, Issue 1.
McKeown, et al., "Molecular characterization of porcine TT virus, an orphan virus, in pigs from six different countries". Veterinary Microbiology, 2004, pp. 113-117, vol. 104, Issues 1-2.
Mouillesseaux, et al., Improvement in the specificity and sensitivity of detection for the Taura syndrome virus and yellow head virus of penaeid shrimp by increasing the amplicon size in SYBR Green real-time RT-PCR. Journal of Virological Methods, 2003, pp. 121-127, vol. 111, Issue 2.
Mueller, et al., "Gene expression of the human Torque Teno Virus isolate P/1C1" Virology, 2008, pp. 36-45, vol. 381, Issue 1.
Ng, et al., "Novel anellovirus discovered from a mortality event of captive California sea lions". Journal of General Virology, 2009, pp. 1256-1261, vol. 90, Pt 5.
Niel, et al., "Coinfection with multiple TT virus strains belonging to different genotypes is a common event in healthy Brazilian adults". Journal of Clinical Microbiology, 2000, pp. 1926-1930, vol. 38, No. 5.
Ninomiya, et al., "Analysis of the entire genomes of torque teno midi virus variants in chimpanzees: infrequent cross-species infection between humans and chimpanzees". Journal of General Virology, 2009, pp. 347-358, vol. 90, Pt 2.
Nishizawa, et al., "A novel DNA virus (TTV) associated with elevated transaminase levels in posttransfusion hepatitis of unknown etiology". Biochemical Biophysical Research Communications, 1997, pp. 92-97, vol. 241, No. 1.
Okamoto, et al., "History of discoveries and pathogenicity of TT viruses". Current Topics in Microbiology and Immunology, 2009, pp. 1-20, vol. 331.
Okamoto, et al., "TT viruses in animals". Current Topics in Microbiology and Immunology, 2009, pp. 35-52, vol. 331.
Okamoto, et al., "Genomic and evolutionary characterization of TT virus (TTV) in tupaias and comparison with species-specific TTVs in humans and non-human primates". Journal of General Virology, 2001, pp. 2041-2050, vol. 82, Pt 9.
Okamoto, et al., "Species-specific TT viruses in humans and nonhuman primates and their phylogenetic relatedness". Virology, 2000, pp. 368-378, vol. 277, No. 2.
Okamoto, et al., "TT virus mRNAs detected in the bone marrow cells from an infected individual". Biochemical and Biophysical Research Communications. 2000, pp. 700-707, vol. 279, No. 2.
Okamoto, et al., "Genomic characterization of TT viruses (TTVs) in pigs, cats and dogs and their relatedness with species-specific TTVs in primates and tupaias". Journal of General Virology, 2002, pp. pp. 700-707, vol. 83, Pt 6.
Opriessnig, et al., "Porcine circovirus type 2 associated disease: update on current terminology, clinical manifestations, pathogenesis, diagnosis, and intervention strategies". Journal of Veterinary Diagnostic Investestigation, 2007, pp. 591-615, vol. 19.
Pal, et al., "Development and validation of a duplex real-time PCR assay for the simultaneous detection and quantification of porcine circovirus type 2 and an internal control on porcine semen samples". Journal of Virological Methods, 2008, pp. 217-225, vol. 149.
Peters, et al., "Attenuation of chicken anemia virus by site-directed mutagenesis of VP2". Journal of General Virology, 2007, pp. 2168-2175, vol. 88, Pt. 8.
Peters, et al., "Site-directed mutagenesis of the VP2 gene of Chicken anemia virus affects virus replication, cytopathology and host-cell MHC class I expression". Journal of General Virology, 2006, pp. 823-831, vol. 87, Pt. 4.
Peters, et al., "Chicken anemia virus VP2 is a novel dual specificity protein phosphatase". Journal of Biological Chemistry, 2002, pp. 39566-39573, vol. 277, No. 42.
Pozzuto, et al., "In utero transmission of porcine torque teno viruses". Veterinary Microbiology, 2009, pp. 375-379, vol. 137.
Prasetyo, et al., "Replication of chicken anemia virus (CAV) requires apoptin and is complemented by VP3 of human torque teno virus (TTV)". Virology, 2009, pp. 85-92, vol. 385, No. 1.
Qiu, et al., "Human circovirus TT virus genotype 6 expresses six proteins following transfection of a full-length clone". Journal of Virology, 2005, pp. 6505-6510, vol. 79, No. 10.
Ririe, et al., "Product differentiation by analysis of DNA melting curves during the polymerase chain reaction". Analytical Biochemistry, 1997, pp. 154-160, vol. 245.

(56) References Cited

OTHER PUBLICATIONS

Sibila, et al., "Swine torque teno virus (TTV) infection and excretion dynamics in conventional pig farms". Veterinary Microbiology, 2009, pp. 213-228, vol. 139.

Takayama, et al., "Prevalence and persistence of a novel DNA TT virus (TTV) infection in Japanese haemophiliacs". British Journal of Haematology, 1999, vol. 104, No. 3, pp. 626-629.

Wilhelm, et al., "Real-time PCR protocol for the detection of porcine parvovirus in field samples". Journal of Virological Methods, 2006, pp. 257-260, vol. 134.

Genbank; GU456383.1.
Genbank; GU456384.1.
Genbank; GU456385.1.
Genbank; GU456386.1.

* cited by examiner

INFECTIOUS GENOMIC DNA CLONE AND SEROLOGICAL PROFILE OF TORQUE TENO SUS VIRUS 1 AND 2

REFERENCE TO RELATED APPLICATION

This patent application in a continuation-in-part of U.S. patent application Ser. No. 12/861,378, which claims the benefit of U.S. Provisional Patent Application No. 61/235,833, filed on Aug. 21, 2009, and U.S. Provisional Patent Application 61/316,519, filed on Mar. 23, 2010. The disclosures of the above mentioned priority applications are hereby incorporated by reference in their entirety into the present disclosure.

FIELD OF INVENTION

The present invention relates to infectious DNA clones of Torque teno sus virus (TTsuV), also known as porcine Torque teno virus (PTTV), and diagnosis of Torque teno sus virus (TTsuV) infection, particularly diagnosis of species- or type-specific TTsuV infection, and simultaneous infection of multiple strains from different genotypes.

BACKGROUND OF THE INVENTION

Anelloviruses are small, single-stranded, circular DNA viruses that infect a wide range of animal species from humans to domestic animals including pigs (Hino, S., and H. Miyata. 2007. Torque teno virus (TTV): current status. Rev Med Virol 17:45-57; Okamoto, H. 2009. TT viruses in animals. Curr Top Microbiol Immunol 331:35-52). Most recently, all human and other animal anelloviruses have been assigned into a newly established family Anelloviridae that includes nine genera (Biagini, P., M. Bendinelli, S. Hino, L. Kakkola, A. Mankertz, C. Niel, H. Okamoto, S. Raidal, C. G. Teo, and D. Todd. 2011. Anelloviridae, p. 331-341. In A. M. Q. King, M. J. Adams, E. B. Carstens, and E. J. Lefkowitz (ed.), Virus Taxonomy, 9th Report of the ICTV. Elsevier Academic Press, London). Human anelloviruses include Torque teno virus (TTV), Torque teno mini virus (TTMV) and Torque teno midi virus (TTMDV) that belong to three different genera. Human TTV, TTMV and TTMDV are non-enveloped spherical viruses with DNA genomes of 3.6-3.9, 2.8-2.9 and 3.2 kb in length, respectively (Okamoto, H. 2009. History of discoveries and pathogenicity of TT viruses. Curr Top Microbiol Immunol 331:1-20). These three groups of human anelloviruses show a high degree of genetic diversity, and infections of TTV, TTMV and TTMDV at a high prevalence in human populations have been documented worldwide (Ninomiya, M., M. Takahashi, T. Nishizawa, T. Shimosegawa, and H. Okamoto. 2008. Development of PCR assays with nested primers specific for differential detection of three human anelloviruses and early acquisition of dual or triple infection during infancy. J Clin Microbiol 46:507-14; Okamoto, H. 2009. History of discoveries and pathogenicity of TT viruses. Curr Top Microbiol Immunol 331:1-20). On the other hand, porcine anelloviruses or Torque teno sus viruses (TTsuV) is assigned into a new genus Iotatorquevirus comprising two species (TTsuV1 and TTsuV2), each also characterized by high genetic diversity with a genomic size of approximately 2.8 kb (Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:287-97; Niel, C., L. Diniz-Mendes, and S. Devalle. 2005. Rolling-circle amplification of Torque teno virus (TTV) complete genomes from human and swine sera and identification of a novel swine TTV genogroup. J Gen Virol 86:1343-7). TTSuV1 and TTSuV2 are highly prevalent in pig populations in many countries (Gallei, A., S. Pesch, W. S. Esking, C. Keller, and V. F. Ohlinger. 2010. Porcine Torque teno virus: determination of viral genomic loads by genogroup-specific multiplex rt-PCR, detection of frequent multiple infections with genogroups 1 or 2, and establishment of viral full-length sequences. Vet Microbiol 143:202-12; Kekarainen, T., M. Sibila, and J. Segales. 2006. Prevalence of swine Torque teno virus in post-weaning multisystemic wasting syndrome (PMWS)-affected and non-PMWS-affected pigs in Spain. J Gen Virol 87:833-7; McKeown, N. E., M. Fenaux, P. G. Halbur, and X. J. Meng. 2004. Molecular characterization of porcine TT virus, an orphan virus, in pigs from six different countries. Vet Microbiol 104:113-7).

Human and porcine anelloviruses share the same genomic structure, which consists of at least four presumed open reading frames (ORFs), ORF1, ORF2, ORF1/1 and ORF2/2, as well as a short stretch of high GC content in the untranslated region (UTR) (Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:287-97; Okamoto, H., M. Takahashi, T. Nishizawa, A. Tawara, K. Fukai, U. Muramatsu, Y. I Saito, and A. Yoshikawa. 2002. Genomic characterization of TT viruses (TTVs) in pigs, cats and dogs and their relatedness with species-specific TTVs in primates and tupaias. J Gen Virol 83:1291-7; 39. Qiu, J., L. Kakkola, F. Cheng, C. Ye, M. Soderlund-Venermo, K. Hedman, and D. J. Pintel. 2005. Human circovirus TT virus genotype 6 expresses six proteins following transfection of a full-length clone, J Virol 79:6505-10). The transcription pattern and related translational products of human TTV genogroup 1 have been experimentally determined by using two full-length TTV DNA clones (Mueller, B., A. Maerz, K. Doberstein, T. Finsterbusch, and A. Mankertz. 2008. Gene expression of the human Torque Teno Virus isolate P/1C1. Virology 381:36-45; 39. Qiu, J., L. Kakkola, F. Cheng, C. Ye, M. Soderlund-Venermo, K. Hedman, and D. J. Pintel. 2005. Human circovirus TT virus genotype 6 expresses six proteins following transfection of a full-length clone, J Virol 79:6505-10). It was shown that the human TTV genome expresses three or more spliced mRNAs encoding at least six proteins, ORF1, ORF2, ORF1/1, ORF2/2, ORF1/2 and ORF2/3 (Mueller, B., A. Maerz, K. Doberstein, T. Finsterbusch, and A. Mankertz. 2008. Gene expression of the human Torque Teno Virus isolate P/1C1. Virology 381:36-45). The transcriptional analysis and protein expression profile using cloned full-length genomic DNA have not been reported for TTSuV.

The ORF1 of TTSuV is believed to encode a viral capsid and replication-associated protein (Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:287-97; Okamoto, H., M. Takahashi, T. Nishizawa, A. Tawara, K. Fukai, U. Muramatsu, Y. I Saito, and A. Yoshikawa. 2002. Genomic characterization of TT viruses (TTVs) in pigs, cats and dogs and their relatedness with species-specific TTVs in primates and tupaias. J Gen Virol 83:1291-7). IgG antibodies against the ORF1 of TTV and TTSuV have been detected in human and pig sera, respectively (15. Huang, Y. W., K. K. Harrall, B. A. Dryman, N. M.

Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88; Kakkola, L., H. Boden, L. Hedman, N. Kivi, S. Moisala, J. Julin, J. Yla-Liedenpohja, S. Miettinen, K. Kantola, K. Hedman, and M. Soderlund-Venermo. 2008. Expression of all six human Torque teno virus (TTV) proteins in bacteria and in insect cells, and analysis of their IgG responses. Virology 382:182-9; 38. Ott, C., L. Duret, I. Chemin, C. Trepo, B. Mandrand, and F. Komurian-Pradel. 2000. Use of a TT virus ORF1 recombinant protein to detect anti-TT virus antibodies in human sera. J Gen Virol 81:2949-58).

The pathogenic potential of anellovirus is still controversial. Currently, human TTV is not considered to be directly associated with a particular disease, although recent studies suggested TTV may serve as an immunological trigger of multiple sclerosis (Maggi, F., and M. Bendinelli. 2010. Human anelloviruses and the central nervous system. Rev Med Virol 20:392-407). Similarly, whether TTSuV is associated with a swine disease is still debatable. TTSuV1 was shown to partially contribute to the experimental induction of porcine dermatitis and nephropathy syndrome (PDNS) and postweaning multisystemic wasting syndrome (PMWS or porcine circovirus associated disease, PCVAD) in a gnotobiotic pig model (Ellis, J. A., G. Allan, and S. Krakowka. 2008. Effect of coinfection with genogroup 1 porcine torque teno virus on porcine circovirus type 2-associated postweaning multisystemic wasting syndrome in gnotobiotic pigs. Am J Vet Res 69:1608-14; 22. Krakowka, S., C. Hartunian, A. Hamberg, D. Shoup, M. Rings, Y. Zhang, G. Allan, and J. A. Ellis. 2008. Evaluation of induction of porcine dermatitis and nephropathy syndrome in gnotobiotic pigs with negative results for porcine circovirus type 2. Am J Vet Res 69:1615-22). PMWS-affected pigs in Spain had a higher prevalence and viral loads of TTSuV2 than the PMWS-unaffected pigs (Aramouni, M., J. Segales, M. Sibila, G. E. Martin-Valls, D. Nieto, and T. Kekarainen. 2011. Torque teno sus virus 1 and 2 viral loads in postweaning multisystemic wasting syndrome (PMWS) and porcine dermatitis and nephropathy syndrome (PDNS) affected pigs. Vet Microbiol 153:377-81; 21. Kekarainen, T., M. Sibila, and J. Segales. 2006. Prevalence of swine Torque teno virus in post-weaning multisystemic wasting syndrome (PMWS)-affected and non-PMWS-affected pigs in Spain. J Gen Virol 87:833-7). Moreover, a significantly lower level of anti-TTSuV2 antibody was found in PCVAD-affected pigs than in PCVAD-unaffected pigs (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). However, results from other studies did not support a direct association of TTSuV1 or TTSuV2 with PCVAD or association of type 2 porcine circovirus (PCV2) and TTSuV with porcine reproductive failures (Gauger, P. C., K. M. Lager, A. L. Vincent, T. Opriessnig, M. E. Kehrli, Jr., and A. K. Cheung. 2011. Postweaning multisystemic wasting syndrome produced in gnotobiotic pigs following exposure to various amounts of porcine circovirus type 2a or type 2b. Vet Microbiol 153:229-39; Huang, Y. W., K. K. Harrall, B. A. Dryman, T. Opriessnig, E. M. Vaugh, M. B. Roof, and X. J. Meng. 2012. Serological profile of Torque teno sus virus species 1 (TTSuV1) in pigs and antigenic relationships between two TTSuV1 genotypes (1a and 1b), between two species (TTSuV1 and 2), and between porcine and human anelloviruses. J. Virol. Submitted Manuscript; Lee, S. S., S. Sunyoung, H. Jung, J. Shin, and Y. S. Lyoo. 2010. Quantitative detection of porcine Torque teno virus in Porcine circovirus-2-negative and Porcine circovirus-associated disease-affected pigs. J Vet Diagn Invest 22:261-4; Ritterbusch, G. A., C. A. Sa Rocha, N. Mores, N. L. Simon, E. L. Zanella, A. Coldebella, and J. R. Ciacci-Zanella. 2011. Natural co-infection of torque teno virus and porcine circovirus 2 in the reproductive apparatus of swine. Res Vet Sci. doi: 10.1016/j.rvsc.2011.04.001).

Due to the lack of a cell culture system to propagate anelloviruses, little is known regarding the molecular biology and pathogenesis of anelloviruses. In order to definitively characterize diseases associated with anellovirus infection, an appropriate animal model is needed. Since multiple infections of different genotypes or subtypes of human TTV or TTSuV are common events (Gallei, A., S. Pesch, W. S. Esking, C. Keller, and V. F. Ohlinger. 2010. Porcine Torque teno virus: determination of viral genomic loads by genogroup-specific multiplex rt-PCR, detection of frequent multiple infections with genogroups 1 or 2, and establishment of viral full-length sequences. Vet Microbiol 143:202-12; Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:287-97; Ninomiya, M., M. Takahashi, T. Nishizawa, T. Shimosegawa, and H. Okamoto. 2008. Development of PCR assays with nested primers specific for differential detection of three human anelloviruses and early acquisition of dual or triple infection during infancy. J Clin Microbiol 46:507-14), a biologically pure and isolated form of a specific anellovirus generated from full-length infectious DNA clone is also required for a pathological study of a single phenotype. Although infectious DNA clones of human TTV in cultured cells have been reported (de Villiers, E. M., S. S. Borkosky, R. Kimmel, K. Gunst, and J. W. Fei. 2011. The diversity of torque teno viruses: in vitro replication leads to the formation of additional replication-competent subviral molecules. J Virol 85:7284-95; Kakkola, L., J. Tommiska, L. C. Boele, S. Miettinen, T. Blom, T. Kekarainen, J. Qiu, D. Pintel, R. C. Hoeben, K. Hedman, and M. Soderlund-Venermo. 2007. Construction and biological activity of a full-length molecular clone of human Torque teno virus (TTN) genotype6. FEBS J 274:4719-30; Leppik, L., K. Gunst, M. Lehtinen, J. Dillner, K. Streker, and E. M. de Villiers. 2007. In vivo and in vitro intragenomic rearrangement of TT viruses. J Virol 81:9346-56), it is important to construct an infectious TTSuV DNA clone so that TTSuV can be used as a useful model to study the replication and transcription mechanisms and to dissect the structural and functional relationships of anellovirus genes. More importantly, the availability of a TTSuV infectious DNA clone will afford us an opportunity to use the pig as a model system to study the replication and pathogenesis of TTSuV or even human TTV.

Multiple infections of human TTV with different genotypes in a single human individual or TTSuV with different genotypes or subtypes in a single pig have been documented (Ball, J. K., R. Curran, S. Berridge, A. M. Grabowska, C. L. Jameson, B. J. Thomson, W. L. Irving, and P. M. Sharp. 1999. TT virus sequence heterogeneity in vivo: evidence for co-infection with multiple genetic types. J Gen Virol 80 (Pt 7): 1759 68; Forms, X., P. Hegerich, A. Darnell, S. U. Emerson, R. H. Purcell, and J. Bukh. 1999. High prevalence of TT virus (TTV) infection in patients on maintenance hemodialysis:

frequent mixed infections with different genotypes and lack of evidence of associated liver disease. J Med Virol 59:313-7; Gallei, A., S. Pesch, W. S. Esking, C. Keller, and V. F. Ohlinger. 2010. Porcine Torque teno virus: determination of viral genomic loads by genogroup-specific multiplex rt-PCR, detection of frequent multiple infections with genogroups 1 or 2, and establishment of viral full-length sequences. Vet Microbiol 143:202-12; Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396: 289-97; Jelcic, I., A. Hotz-Wagenblatt, A. Hunziker, H. Zur Hausen, and E. M. de Villiers. 2004. Isolation of multiple TT virus genotypes from spleen biopsy tissue from a Hodgkin's disease patient: genome reorganization and diversity in the hypervariable region. J Virol 78:7498-507; Niel, C., F. L. Saback, and E. Lampe. 2000. Coinfection with multiple TT virus strains belonging to different genotypes is a common event in healthy Brazilian adults. J Clin Microbiol 38:1926-30; Ninomiya, M., M. Takahashi, T. Nishizawa, T. Shimosegawa, and H. Okamoto. 2008. Development of PCR assays with nested primers specific for differential detection of three human anelloviruses and early acquisition of dual or triple infection during infancy. J Clin Microbiol 46:507-14). These findings raise the question whether the anti-ORF1 capsid antibodies recognized by the antigen from a particular TTV or TTSuV species/geno types also comprise anti-ORF1 antibodies against other distinct TTV or TTSuV species/genotypes and whether the anti-ORF1 antibodies from one TTV or TTSuV genotype can cross-protect against infection with another genotype. To our knowledge, for human TTV or TTSuV infection there is no information on this topic available to date. Furthermore, the antigenic diversity and relationship of anelloviruses have never been assessed (Maggi, F., and M. Bendinelli. 2009. Immunobiology of the Torque teno viruses and other anelloviruses. Curr Top Microbiol Immunol 331:65-90). It is reasonable to speculate that there is little, if any, antigenic cross-reactivity between different anellovirus species/genotypes, due to the fact that concurrent infections with multiple anelloviruses in a single individual or animal exist.

The inventors have previously developed and validated serum Western blot (WB) and indirect ELISA assays for detection of the IgG antibody against TTSuV2 in porcine sera using the purified recombinant TTSuV2-ORF1 protein expressed in *E. coli* (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). By using TTSuV2-specific real-time quantitative PCR (qPCR) and ELISA, The inventors further presented the combined virological and serological profile of TTSuV2 infection under natural or diseased conditions using 160 porcine sera collected from different sources (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). In the present invention, The inventors initially aimed to assess the serological profiles of the two TTSuV1 genotypes (TTSuV1a and TTSuV1b) in pigs, respectively. Subsequently, the inventors aimed to compare the virological and serological profiles of TTSuV1a and TTSuV1b with that of TTSuV2, and to determine the degree of correlation of IgG antibody levels between anti-TTSuV1a and -TTSuV1b and between anti-TTSuV1a or -1b and anti-TTSuV2. Finally, for the first time, the inventors assessed the antigenic relationships between two TTSuV1 genotypes (TTSuV1a and TTSuV1b), between two species (TTSuV1 and TTSuV2), and between porcine and human genogroup 1 anelloviruses using ELISA and immunofluorescence assay with antibody cross-reactions in PK-15 cells transfected with recombinant plasmids expressing the ORF1s from TTSuV1a, TTSuV1b and TTSuV2, respectively.

SUMMARY OF THE INVENTION

The present invention provides an infectious nucleic acid molecule of Torque teno sus virus (TTsuV) comprising a nucleic acid molecule encoding an infectious TTsuV which contains at least one copy of genomic sequence having at least 85% homology to a genomic sequence of TTsuV2.

According to one embodiment, the at least one copy of genomic sequence having at least 95% homology to the genomic sequence of TTsuV2.

According to another embodiment, the genomic sequence of TTsuV2 is of genomic clone of PTTV2c-VA. In one specific example, the genomic sequence is selected from sequences set forth in SEQ ID NO:1.

According to a further embodiment, the genomic sequence of TTsuV2 is of genomic clone of TTV2-#471942. In a specific example, the genomic sequence is selected from sequences set forth in SEQ ID NO:2.

According to an additional embodiment, the genomic sequence of TTsuV2 comprising at least one genetic marker in intron 1. In a specific example, the genetic marker in intron 1 is an artificially introduced restriction site.

The present invention provides a biologically functional plasmid or viral vector containing an infectious nucleic acid molecule of Torque teno sus virus (TTsuV) comprising a nucleic acid molecule encoding an infectious TTsuV which contains at least one copy of genomic sequence having at least 85% homology to a genomic sequence of TTsuV2.

According to one embodiment, the biologically functional plasmid or viral vector contains more than one copy of the infectious nucleic acid molecule.

According to one embodiment, the biologically functional plasmid or viral vector contains tandem copies of genomic clone of PTTV2c-VA.

The present invention provides an infectious TTsuV produced by cells containing the infectious nucleic acid sequence of TTsuV2 is of genomic clone of PTTV2c-VA.

The present invention provides a method for diagnosing TTsuV infection, comprising immobilizing an immunogentic fragment or a complete protein of a polypeptide sequence of ORF1 protein of TTsuV 1 or 2, contacting a serum sample from a pig suspected of TTsuV infection with the immobilized immunogentic fragment or complete protein, and detecting captured antibody specific to the immunogentic fragment.

According to one embodiment, the polypeptide sequence is selected from the group consisting of ORF1 proteins of TTsuV genotypes or subtypes TTsuV1a,\ or TTsuV1b.

According to another embodiment, the polypeptide sequence is selected from the group consisting of N-terminal truncated ORF1 proteins of TTsuV genotypes or subtypes TTsuV1a, TTsuV1b or TTsuV2. In a specific example, the polypeptide sequence is amino acid No. 317-635 of ORF1 protein of TTsuV1a. In another example, the polypeptide sequence is amino acid No. 322-639 of ORF1 protein of TTsuV1b.

BRIEF DESCRIPTION OF THE DRAWINGS

The above-mentioned features of the invention will become more clearly understood from the following detailed description of the invention read together with the drawings in which.

DETAILED DESCRIPTION OF THE INVENTION

Figure 1:
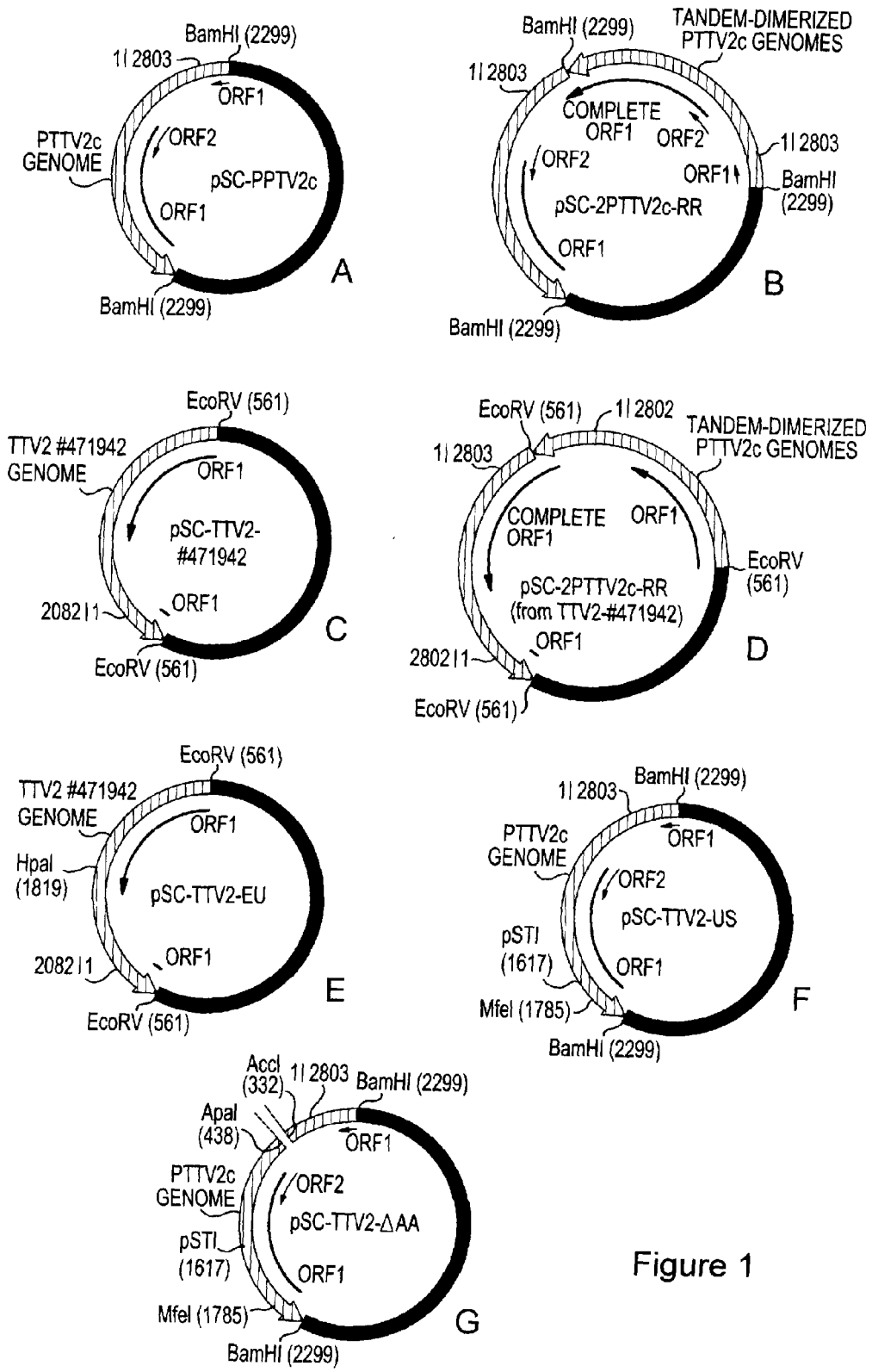
FIG. 1 is a schematic diagrams of TTsuV2 constructs containing full-length TTsuV2 genomic DNA. (A) pSC-PTTV2c (from the U.S. TTsuV2 isolate PTTV2c-VA; GenBank accession no. GU456386). (B) pSC-2PTTV2c-RR (tandem-dimerized PTTV2C-VA genomes). (C) pSC-TTV2-#471942 (from the German TTsuV2 isolate TTV2-#471942; GenBank accession no. GUI88046). (D) pSC-2PTTV2b-RR (tandem-dimerized TTV2-#471942 genomes). (E) pSC-TTV2-EU (derived from pSC-TTV2-#471942). A HpaI site as the silent genetic marker was introduced in this clone. (F) pSC-TTV2-US (derived from pSC-PTTV2c). PstI and MfeI sites as the silent genetic markers were introduced in this clone. (G) pSC-TTV2-AAA. A 104-bp deletion mutation was introduced between the AccI and ApaI sites ranging from the putative TATA box to the ORF1 start codon on the clone pSC-TTV2-US. The restriction enzymes (BamHI or EcoRV) used for plasmids constructions are shown. The plasmid backbone used for cloning was the pSC-B-amp/kan vector (indicated by black). Grey arrows indicate the TTsuV2 genomic copies.

FIG. 1 is a schematic diagrams of TTSuV2 constructs containing full-length TTSuV2 genomic DNA. (A) pSC-PTTV2c (from the U.S. TTSuV2 isolate PTTV2c-VA; GenBank accession no. GU456386; SEQ ID NO:1). (B) pSC-2PTTV2c-RR (tandem-dimerized PTTV2C-VA genomes). (C) pSC-TTV2 #472142 (from the German TTSuV2 isolate TTV2-#472142; GenBank accession no. GU188046; SEQ ID NO:2). (D) pSC-2PTTV2b-RR (tandem-dimerized TTV2-#471942 genomes). (E) pSC-TTV2-EU (derived from pSC-TTV2-#471942). A HpaI site as the silent genetic marker was introduced in this clone. (F) pSC-TTV2-US (derived from pSC-PTTV2c). PstI and MfeI sites as the silent genetic markers were introduced in this clone. (G) pSC-TTV2-AAA. A 104-bp deletion mutation was introduced between the AccI and ApaI sites ranging from the putative TATA box to the ORF1 start codon on the clone pSC-TTV2-US. The restriction enzymes (BamHI or EcoRV) used for plasmids constructions are shown. The plasmid backbone used for cloning was the pSC-B-amp/kan vector (indicated by black). Grey arrows indicate the TTSuV2 genomic copies.

In the present invention, the inventors describe the construction and initial characterization of full-length DNA clones of TTSuV2 in vitro and in vivo. The inventors provide, for the first time, definite evidence of splicing of TTSuV2 mRNA and expression of the putative ORF1 capsid protein by transfection of the TTSuV2 full-length DNA clones in cultured cells. Furthermore, rescue of TTSuV2 containing the introduced genetic markers in pigs was confirmed by sequencing of viral DNA obtained from pigs experimentally inoculated with the circular TTSuV2 genomic DNA. Anellovirus is a group of single-stranded circular DNA viruses infecting human and various other animal species. Animal models combined with reverse genetics systems of anellovirus have not been developed. The inventors report here the construction and initial characterization of full-length DNA clones of a porcine anellovirus, Torque teno sus virus 2 (TTSuV2), in vitro and in vivo. The inventors first demonstrated that five cell lines including PK-15 are free of TTSuV1 or TTSuV2 contamination, as determined by real-time PCR and immunofluorescence assay (IFA) using rabbit anti-TTSuV ORF1 sera. Recombinant plasmids harboring monomeric or tandem-dimerized TTSuV2 genomic DNA that originated from the United States and Germany were constructed. Circular TTSuV2 genomic DNA with or without introduced genetic markers and tandem-dimerized TTSuV2 plasmids were transfected into the PK-15 cells, respectively. Splicing of viral mRNAs was identified in transfected cells. Expression of TTSuV2-specific ORF1 in cell nuclei, especially in nucleoli, was detected by IFA. However, evidence of productive TTSuV2 infection was not observed in 12 different cell lines including the 293TT cell line transfected with the TTSuV2 DNA clones. Transfection with circular DNA from a TTSuV2 deletion mutant did not produce ORF1 proteins, suggesting that the observed ORF1 expression in this study is driven by TTSuV2 DNA replication in cells. Pigs inoculated with either the tandem-dimerized plasmids or circular DNA derived from the U.S. strain of TTSuV2 containing genetic markers developed viremia, and the introduced genetic markers were retained in viral DNA extracted from the sera of infected pigs. The availability of an infectious DNA clone of TTSuV2 will facilitate future study of porcine anellovirus pathogenesis and biology.

Figure 2:
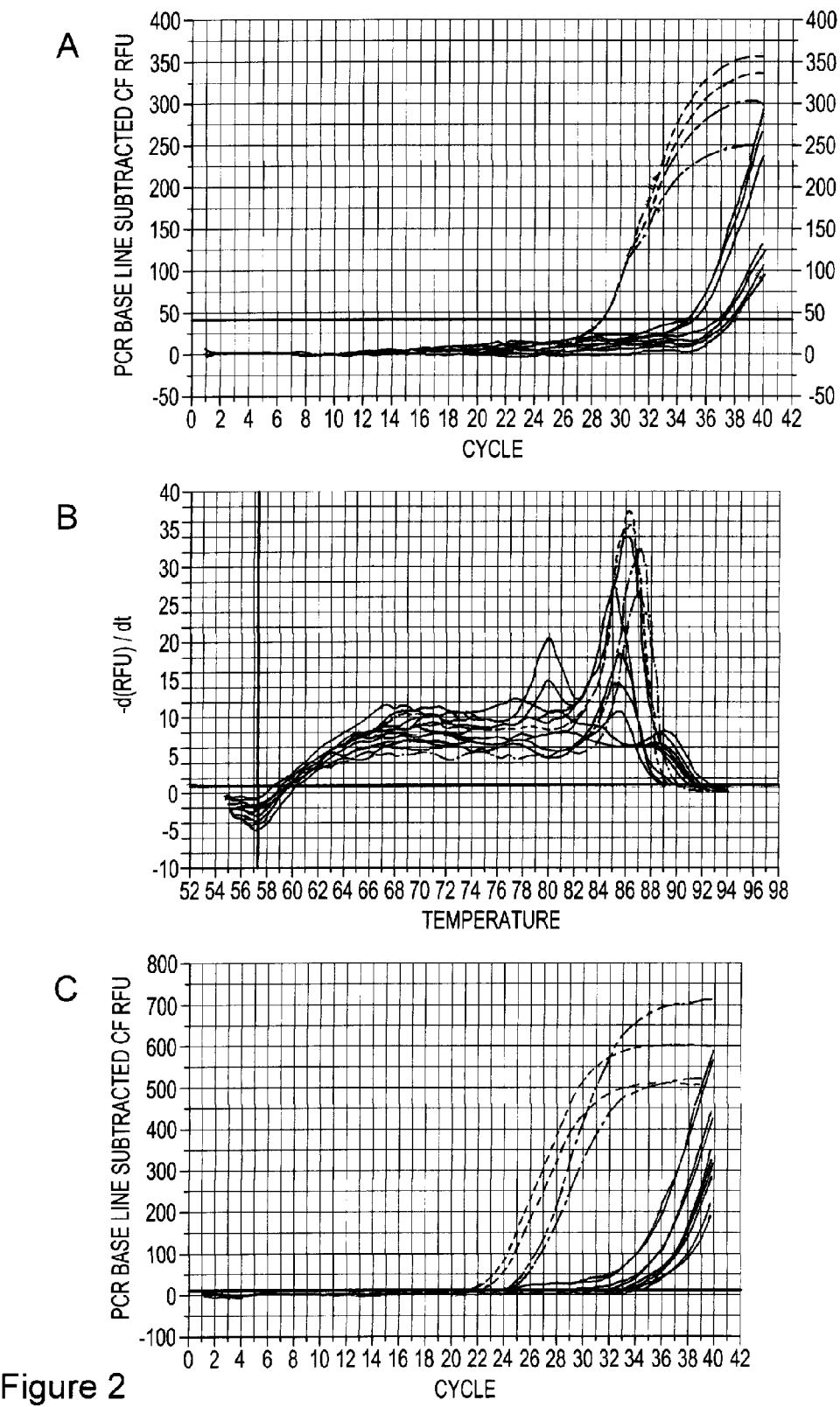
FIG. 2 illustrates detection of TTsuV1 or TTsuV2 contamination in live different cell lines (PCV1-free PK-15, 3D4/31, IPEC/J2, BHK-21 and MARC-145) and an CHE diseases-free porcine serum by real-time qPCR. Fluorescence curves (A and C) and melting curves (B and D) of TTsuV1 (A and B) or TTsuV2 (C and D) qPCR products are shown after 40 cycles of amplifications of the standard template with the minimum dilution limit ($10^{-4}$ pg; indicated by red), five different cell lines (blue) and the porcine serum (green). For each sample, duplicate determinations were made. (E) Detection of specific TTsuV1 or TTsuV2 qPCR products (marked by black arrowheads) by agarose gel electrophoresis.
Figure 2:
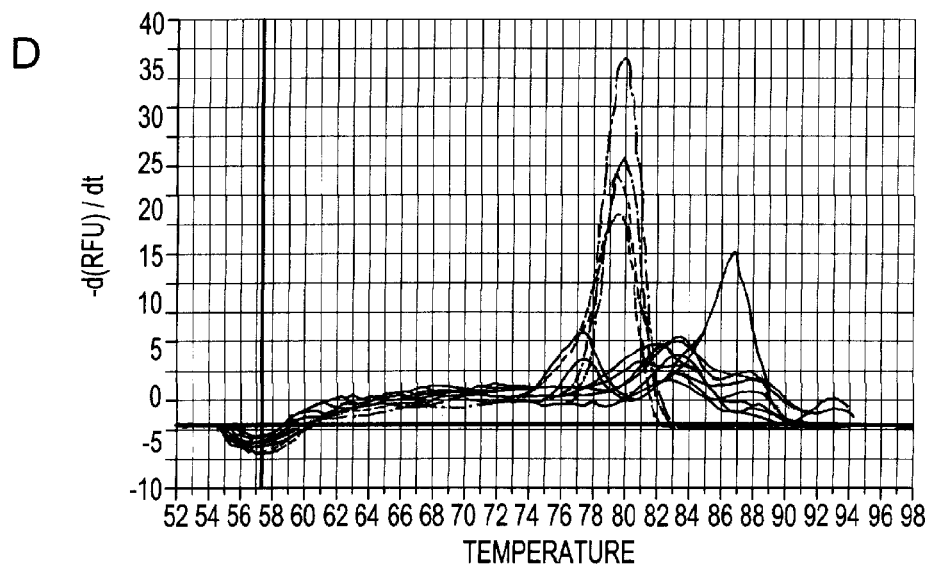
Figure 2:
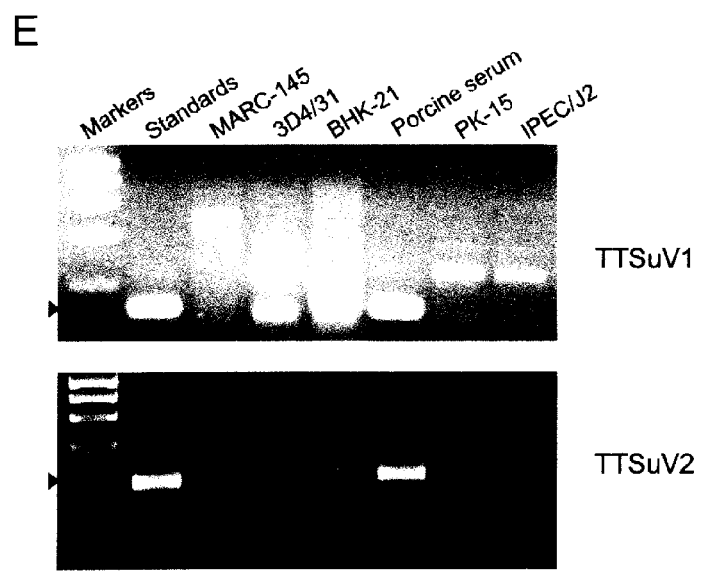

Neither the viral DNA nor the expression of the putative ORF1 capsid protein of TTSuV1 or TTSuV2 was endogenously present in five representative cell lines tested in this study. The present study first aimed to identify potential permissive cell lines supporting the TTSuV propagation. The inventors selected five commonly-used cell lines including three that are of pig origin: PCV1-free PK-15, 3D4/31 and IPEC-J2, and two other cell lines including BHK-21 and MARC-145. These cell lines are known to be permissive for a wide variety of animal virus infections. In order to rule out the possibility of endogenous contamination of TTSuV1 or TTSuV2 in cultured cell lines, both viral DNA and ORF1 protein expression were subjected to TTSuV1 or TTSuV2 real-time qPCR and IFA detections, respectively. An OIE diseases-free porcine serum, which had been shown to have a high level of anti-TTSuV2 ORF1 antibody, was also included as a control (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). The results obtained with the qPCR analysis showed that none of the five cell lines tested in the study were positive for TTSuV1 or TTSuV2 DNA, as determined by the analyses of fluorescence curves, melting curves and agarose gel electrophoresis, since their fluorescence curves were below the minimum detection limit, their melting curves did not overlap with that of the standards, and there were no detectable specific bands corresponding to the expected PCR products (FIG. 2). In contrast, as expected, the commercial porcine serum was positive for TTSuV1 and TTSuV2 DNA (FIG. 2).

Neither the viral DNA nor the expression of the putative ORF1 capsid protein of TTSuV1 or TTSuV2 was endogenously present in five representative cell lines tested in this study. The present study first aimed to identify potential permissive cell lines supporting the TTSuV propagation. The inventors selected five commonly-used cell lines including three that are of pig origin: PCV1-free PK-15, 3D4/31 and IPEC-J2, and two other cell lines including BHK-21 and MARC-145. These cell lines are known to be permissive for a wide variety of animal virus infections. In order to rule out the possibility of endogenous contamination of TTSuV1 or TTSuV2 in cultured cell lines, both viral DNA and ORF1 protein expression were subjected to TTSuV1 or TTSuV2 real-time qPCR and IFA detections, respectively. An OIE diseases-free porcine serum, which had been shown to have a high level of anti-TTSuV2 ORF1 antibody, was also included as a control (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). The results obtained with the qPCR analysis showed that none of the five cell lines tested in the study were positive for TTSuV1 or TTSuV2 DNA, as determined by the analyses of fluorescence curves, melting curves and agarose gel electrophoresis, since their fluorescence curves were below the minimum detection limit, their melting curves did not overlap with that of the standards, and there were no detectable specific bands corresponding to the expected PCR products (FIG. 2). In contrast, as expected, the commercial porcine serum was positive for TTSuV1 and TTSuV2 DNA (FIG. 2).

To develop cell-based serological methods such as IFA or immunoperoxidase monolayer assay (IPMA) for TTSuV detection, the inventors raised three specific antisera against the putative ORF1 capsid protein of TTSuV1a, TTSuV1b (Huang, Y. W., K. K. Harrall, B. A. Dryman, T. Opriessnig, E. M. Vaugh, M. B. Roof, and X. J. Meng. 2012. Serological profile of Torque teno sus virus species 1 (TTSuV1) in pigs and antigenic relationships between two TTSuV1 genotypes (1a and 1b), between two species (TTSuV1 and 2), and between porcine and human anelloviruses. J. Virol. Submitted Manuscript) or TTSuV2 in rabbits. When the five cell lines were stained with each of the three virus-specific antisera, respectively, no positive fluorescence signals were detected, indicating the absence of endogenous TTSuV1 or TTSuV2 ORF1 expression (data not shown). The IFA results were consistent with the qPCR detection, which demonstrated that the five selected cell lines were not contaminated with TTSuV1 or TTSuV2 and thus can be used for testing the susceptibility of TTSuV infection or replication by transfection with TTSuV DNA clones.

Construction and characterization of full-length TTSuV2 DNA clones in porcine kidney PK-15 cells. The inventors were particularly interested in characterizing the infectivity of TTSuV2 full-length DNA clone since TTSuV2 has been reported to be associated with PMWS or PCVAD at a high prevalence rate of viral DNA (Kekarainen, T., M. Sibila, and J. Segales. 2006. Prevalence of swine Torque teno virus in post-weaning multisystemic wasting syndrome (PMWS)-affected and non-PMWS-affected pigs in Spain. J Gen Virol 87:833-7), a high viral load (Aramouni, M., J. Segales, M. Sibila, G. E. Martin-Valls, D. Nieto, and T. Kekarainen. 2011. Torque teno sus virus 1 and 2 viral loads in postweaning multisystemic wasting syndrome (PMWS) and porcine dermatitis and nephropathy syndrome (PDNS) affected pigs. Vet Microbiol 153:377-81) and a low antibody level in disease-affected pigs with an unknown mechanism (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). The inventors first generated two monomeric full-length TTSuV2 DNA clones, pSC-PTTV2c and pSC-TTV2-#471942, derived from a prototype U.S. isolate PTTV2c-VA and a German isolate TTV2-#471942, respectively (FIGS. 1A & 1C) (Gallei, A., S. Pesch, W. S. Esking, C. Keller, and V. F. Ohlinger. 2010. Porcine Torque teno virus: determination of viral genomic loads by genogroup-specific multiplex rt-PCR, detection of frequent multiple infections with genogroups 1 or 2, and establishment of viral full-length sequences. Vet Microbiol 143:202-12; Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:287-97). Each of the full-length TTSuV2 genomic DNA was inserted into a cloning vector pSC-B-amp/kan that does not contain a eukaryotic promoter. The restriction site BamHI or EcoRV is the unique site on the PTTV2c-VA or TTV2-#471942 genome, which was engineered at both ends of genomic DNA to facilitate the generation of concatemers and thus to mimic the TTSuV circular DNA genome. BamHI or EcoRV single digestion of the plasmid DNA of each clone clearly resulted in two different fragments of 4.3-Kb and 2.8-Kb in size. The 4.3-Kb fragment represented the backbone vector whereas the 2.8-Kb fragment represented the inserted monomeric TTSuV2 genomic DNA (data not shown).

Subsequently, two copies of the full-length PTTV2c-VA genome from the clone pSC-PTTV2c were ligated in tandem into the pSC-B-amp/kan vector to generate the clone pSC-2PTTV2c-RR (FIG. 1B). Comparison of the AflII single digestion patterns between pSC-PTTV2c and pSC-2PTTV2c-RR showed that the latter clone had an additional 2.8-Kb fragment representing the intact single TTSuV2 genomic DNA (FIG. 3A, right panel). The inventors utilized the same cloning strategy to produce a tandem-dimerized TTSuV2 DNA clone, pSC-2PTTV2b-RR, derived from pSC-TTV2-#471942 (FIG. 1D). Similarly, when digested with HindIII alone, an additional 2.8-Kb fragment representing the intact single TTSuV2 genome was presented in this construct, compared to its monomeric parent clone (FIG. 3A, left panel), thus confirming the successful construction of the clone.

Circular TTSuV2 DNA was generated by tandem ligation of the purified linear TTSuV2 genomic DNA excised from the clone pSC-PTTV2c or pSC-TTV2-#471942. Typical monomer, dimer and high-copy-molecules of concatemerized TTSuV2 DNA were observed in the ligation products (FIG. 3B). The ligation mixture from PTTV2c-VA or TTV2-

471942 was transfected into PCV1-free PK-15 cells. IFA conducted at five days post-transfection, using the rabbit antiserum against PTTV2c-VA ORF1, indicated that TTSuV2 ORF1 antigen was expressed in the nuclei of the transfected cells with approximately 5% positive rate (FIGS. 4A & 4C). No fluorescent signal was observed in mock-transfected cells stained with the same anti-TTSuV2 serum (FIG. 4E) or in circular TTSuV2 DNA-transfected cells stained with the anti-TTSuV1a ORF1, anti-TTSuV1b ORF1 (Huang, Y. W., K. K. Harrall, B. A. Dryman, T. Opriessnig, E. M. Vaugh, M. B. Roof, and X. J. Meng. 2012. Serological profile of Torque teno sus virus species 1 (TTSuV1) in pigs and antigenic relationships between two TTSuV1 genotypes (1a and 1b), between two species (TTSuV1 and 2), and between porcine and human anelloviruses. J. Virol. Submitted Manuscript) or pre-bleed rabbit serum (data not shown). Passaging of the transfected cells for two times did not eliminate but reduced the fluorescent signal (data not shown). When the transfected cells were continuously passaged for up to 20 passages, no positive signal was detectable, suggesting that TTSuV2 infection did not occur (data not shown).

The inventors next tested whether direct transfection of plasmid DNA of the tandem-dimerized clone pSC-2PTTV2c-RR or pSC-2PTTV2b-RR into PK-15 cells resulted in the synthesis of TTSuV2 ORF1. The tandem-dimerized double-stranded DNA does not represent genomic anellovirus DNA but might represent an infectious replicative intermediate. IFA at 5 days post-transfection using the same anti-TTSuV2 ORF1 antiserum confirmed that both DNA clones also expressed ORF1 in transfected PK-15 cells (FIGS. 4B & 4D). Again, the ORF1 was expressed in cell nuclei. However, the fluorescent intensity and positive rate were lower than that in circular TTSuV2 DNA-transfected cells (FIGS. 4B & 4D). The inventors did not observe the localization of ORF1 antigen in the cytoplasm of the transfected cells.

Figure 5:
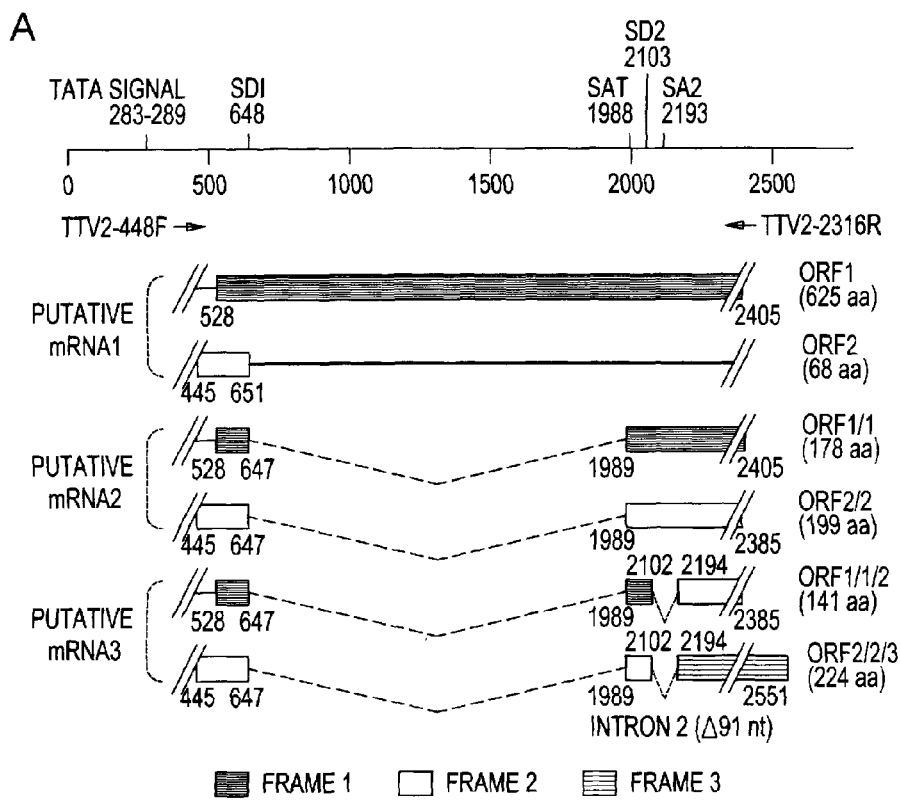
FIG. 5 illustrates the putative transcription profile and protein expression of TTSuV2 based on the PTTV2c-VA genome (a fragment of nucleotides which correspond to nucleotides 1-2500 of SEQ ID NO: 1). (A) Schematic diagram of three putative viral mRNAs and six viral proteins. The TATA box, splicing sites (SD: splicing donor; SA: splicing acceptor) and the positions of primers TTV2-448F (SEQ ID NO:6) and TTV2-2316R (SEQ ID NO:7) were indicated at the top. The three open reading frames (ORFs) are depicted by colored boxes. The sizes of the six ORFs and two introns are also shown. (B) Sequencing of the RT-PCR products amplified by primers TTV2-448F and TTV2-2316R verified the splicing of the putative intron 1. (C) Sequencing of the RT-PCR products amplified by primers TTV2-448F and TTV2-2316R identified an additional intron (intron 2). Arrows and numbers indicate the joint site of the exons.
Figure 5:
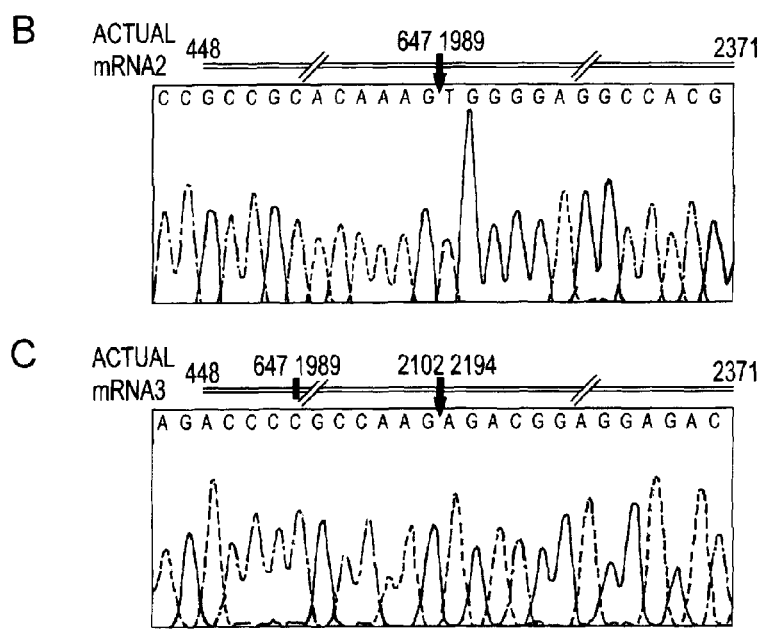

Experimental identification of two introns in the TTSuV2 genome. Although the transcriptional profile using cloned TTSuV full-length genomic DNA has not been reported, we previously speculated that TTSuV likely expresses two essential viral mRNA transcripts, mRNA1 and mRNA2, to produce the four known ORF counterparts of human TTV (FIG. 5A) (Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:287-97). The continuous mRNA1 encodes ORF1 and ORF2 whereas removal of the putative intron of 1341 nt (designated intron 1 here), corresponding to nt positions 648-1988 in PTTV2c-VA genome, generates the putative mRNA2 that encodes two discontinuous ORFs, ORF 1/1 and ORF2/2 (Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:287-97). The inventors also speculated that more spliced mRNAs and their encoding proteins of TTSuV may exist, as shown in human TTV (Mueller, B., A. Maerz, K. Doberstein, T. Finsterbusch, and A. Mankertz. 2008. Gene expression of the human Torque Teno Virus isolate P/1C1. Virology 381:36-45; Qiu, J., L. Kakkola, F. Cheng, C. Ye, M. Soderlund-Venermo, K. Hedman, and D. J. Pintel. 2005. Human circovirus TT virus genotype 6 expresses six proteins following transfection of a full-length clone, J Virol 79:6505-10).

To verify whether the splicing of the putative intron 1 in TTSuV2 occurred, total RNA was extracted in PK-15 cells transfected with circular PTTV2c-VA DNA followed by DNase I treatment and RT-PCR analysis. Two PCR product bands of approximately 500 bp and 600 bp in sizes were visualized by agarose gel electrophoresis. Sequencing of the cloned PCR fragments resulted in the identification of two sequences. As expected, the large cDNA fragment of 583 bp was exactly the intron 1-spliced product (FIG. 5B), whereas the small cDNA product of 492 bp contained two splicing regions including the intron 1 and an additional 91-nt intron, corresponding to nt positions 2103-2193 in PTTV2c-VA genome, which was designated intron 2 in this study (FIG. 5C). The splicing sites are conserved among all published TTSuV2 sequences (data not shown). Therefore, in this study for the first time the inventors experimentally demonstrated the existence of splicing of intron 1 and the viral mRNA2 transcripts. The inventors also identified a novel viral mRNA transcript, termed mRNA3, which encodes two putative proteins, ORF1/1/2 and ORF2/2/3, and which switches reading frames from 1 to 2, and 2 to 3, respectively, due to splicing of intron 2 (FIG. 5A). The mRNA3 transcript contains at least three exons on the TTSuV2 genome. Since the inventors failed to determine the 5'- and 3'-ends of the viral mRNA transcripts by rapid amplification of cDNA ends (RACE)-PCR, it is possible that there exists an additional TTSuV2 intron in the upstream of ORF2, as known in human TTV transcripts (Mueller, B., A. Maerz, K. Doberstein, T. Finsterbusch, and A. Mankertz. 2008. Gene expression of the human Torque Teno Virus isolate P/1C1. Virology 381:36-45). However, human TTV genome does not contain a short intron corresponding to the TTSuV intron 2 in the downstream of the large intron (intron 1).

Nevertheless, transfection of PK-15 cells with circularized TTSuV2 genomic DNA resulted in the synthesis of viral mRNA transcripts and the expression of ORF1 protein, indicating that the TTSuV2 concatemers mimicked the transcription and protein expression from the natural circular genome of TTSuV2.

A tandem-dimerized TTSuV2 clone, pSC-2PTTV2c-RR, is infectious when inoculated in the CD pigs. To test the infectivity of TTSuV2 DNA clones in pigs, the inventors first performed a pilot study with three groups of CD pigs with two pigs per group. The pigs were inoculated with PBS buffer (pig nos. 1 and 2) in group 1, the tandem-dimerized clone pSC-2TTV2c-RR (pig nos. 3 and 4) in group 2, and pSC-2TTV2b-RR (pig nos. 5 and 6) in group 3, respectively. Serum samples were collected from animals at 0, 7, 14, 21, 28, 35 and 42 days post-inoculation (DPI). Pig no. 2 died of septicemia due to an unidentified bacterial infection shortly after inoculation.

TTSuV2 DNA was detected in two pigs inoculated with pSC-2TTV2c-RR beginning at 28 DPI by real-time qPCR. The viral loads, although very low, increased weekly until 42 DPI before necropsy at 44 DPI in both pigs. The viral loads in serum of pig no. 3 increased from $1.93 \times 10^3$ at DPI 28 to $5.59 \times 10^3$ at DPI 35 and $4.36 \times 10^4$ at DPI 42 whereas the serum viral loads in pig no. 4 elevated from $5.07 \times 10^3$ at DPI 28 to $4.49 \times 10^4$ at DPI 35 and $8.87 \times 10^4$ at DPI 42. Moderate microscopic lesions in brain (lymphoplasmacytic encephalitis mainly perivascular), liver (lymphohistiocytic hepatitis) and kidney (lymphoplasmacytic interstitial nephritis) were observed in pig no. 3 but not in no. 4. The remaining three pigs including pigs inoculated with the clone pSC-2TTV2b-RR did not develop viremia throughout the study. However, pig no. 5 had mild lymphohistiocytic multifocal hepatitis. The results from this pilot pig experiment indicated that the clone pSC-2PTTV2c-RR originated from a U.S. strain of TTSuV2 is infectious.

Characterization of two TTSuV2 full-length DNA clones with engineered genetic markers and a derived mutant clone in vitro. To further rule out the possible contamination of other indigenous TTSuV2 infections in the pilot animal study, it is critical to introduce tractable genetic markers in the TTSuV2 genome so that the cloned virus and the potential indigenous contaminating virus in pigs can be discriminated in inoculated animals. The inventors introduced a unique HpaI restriction site and two unique restriction sites, PstI and MfeI, into two TTSuV2 monomeric DNA clones pSC-TTV2-#471942 and pSC-PTTV2c to produce two new clones pSC-TTV2-EU and pSC-TTV2-US, respectively (FIGS. 1E and 1F). The positions of these sites, located in the intron 1, were expected to not change the putative ORF1 capsid amino acid sequence. PK-15 cells were transfected with ligation mixtures of the linear TTSuV2 genomic DNA excised from these two marker clones, respectively. The ORF1 expression in nuclei of the transfected cells was detected by IFA at 3 days post-transfection, similar to the patterns of their parental clones (FIG. 6), indicating that the clones with introduced genetic markers are replication competent.

A mutant clone pSC-TTV2-ΔAA with a 104-bp deletion (nt positions 332-437) from the putative TATA box (nt positions 283-289; FIG. 5A) to the ORF1 (nt 528) and ORF2 (nt 445) start codons was generated based on the clone pSC-TTV2-US (FIG. 1G). When transfected into the PK-15 cells, the circularized DNA from this mutant clone did not express the ORF1 antigen (FIG. 6), suggesting that the deleted region likely contains a cis-acting element important for viral mRNA transcription or TTSuV2 ORF1 translation. The result of the deletion mutant clone also implied that the observed expression of ORF1 is likely driven by the replication-competent TTSuV2 DNA since the tandem-dimerized clone and concatemerized ligation products from the parental PTTV2c-VA genome were both infectious in pigs (see below).

Expression of the TTSuV2 ORF1 protein in various cell lines transfected with the circularized TTSuV2 DNA from the clone pSC-TTV2-US. From the in vitro transfection experiments described above, it appeared that, although the TTSuV2 putative ORF1 capsid protein is expressed, the PK-15 cells do not support the cell-to-cell spread of TTSuV2 recovered from the introduced TTSuV2 DNA clones. Alternatively, it is possible that the assembly of TTSuV2 virions in the transfected PK-15 cells may be deficient. To search for another cell line that may be permissive for TTSuV2 infection, the inventors subsequently transfected eleven other different cell lines with the circularized TTSuV2 DNA from the clone pSC-TTV2-US, respectively. These cell lines included the four cell lines (3D4/31, IPEC-J2, BHK-21 and MARC-145) that were tested negative for TTSuV1 or TTSuV2 at both the DNA and protein levels. The plain cells of the other seven cell lines (ST, Vero, and 293TT, HeLa, Huh-7, HepG2 and CHO-K1) were also negative for TTSuV2 ORF1 as determined by IFA (data not shown).

Figure 7:
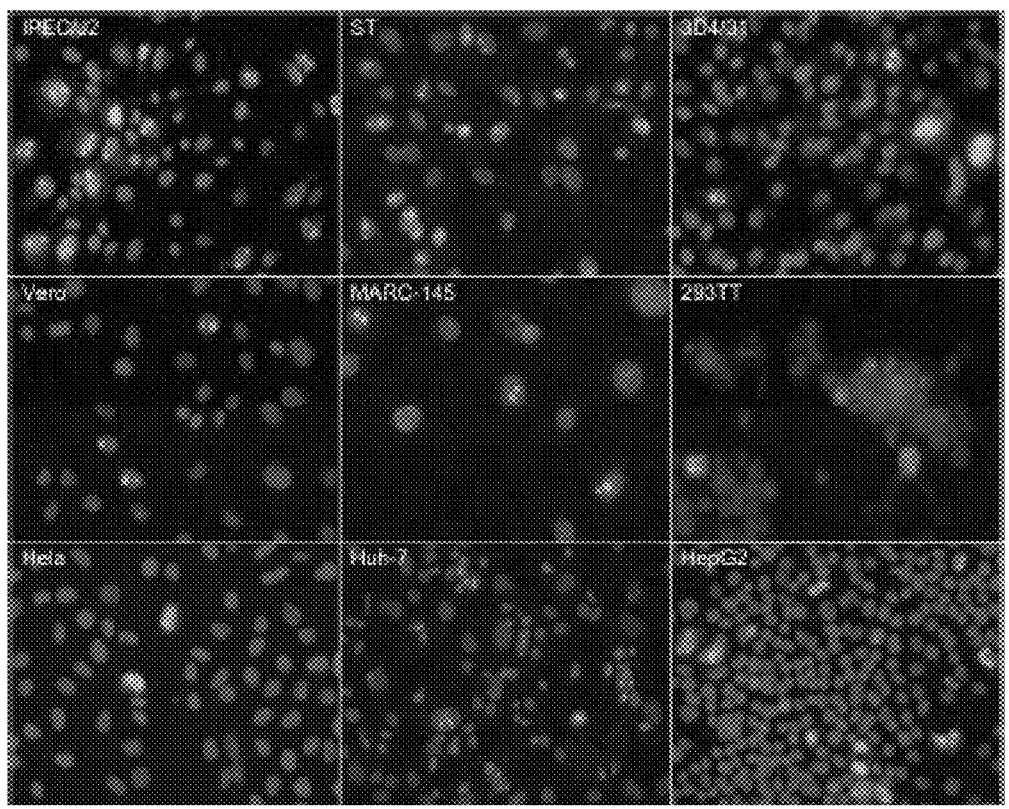
FIG. 7 illustrates transfection of nine different cell lines with the ligation mixture of linear TTsuV2 genomic DNA derived from the clone pSC-TTV2-US. Alexa fluor 488-conjugated antibody (Ab) staining (green) merged with nuclear staining using DAPI (blue) are shown. Magnification=200×.

After transfection, all the eleven cell lines expressed the ORF1 protein at 3 days post-transfection (FIG. 7; the results of BHK-21 and CHO-K1 not shown). The percentages of transfected cells with positive IFA signals were subjectively categorized into three levels: IPEC-J2, ST, PCV1-free PK-15, Huh-7 and HepG2 with a high level of positive rates (>5%); 3D4/31, Vero, MARC-145 and 293TT with a middle level of positive rates (between 2-5%); Hela, BHK-21 and CHO-K1 with a low level of positive rates (<2%). In general, TTSuV2-specific antibody staining patterns of individual positive cells by IFA could be divided into three different types: (i) cells displaying dense nuclear staining; (ii) cells displaying large nuclear inclusion staining; and (iii) cells displaying punctate nuclear staining. The last two patterns indicated the localization of ORF1 antigen in cell nucleoli. No cytoplasmic staining was observed in the transfected cells.

To test if some of these IFA-positive cells were susceptible to TTSuV2 infection, supernatants collected from cell lysates of PK-15, ST and 293TT cells transfected with circularized TTSuV2 DNA were inoculated into all cell lines with high level positive rates and some with middle level positive rates including the 293TT cell line, respectively. The inoculated cells were cultured for 3 to 5 days and examined by IFA. No fluorescent signal was detected in these cells (data not shown), indicating that none of the tested cell lines are susceptible to productive TTSuV2 infection.

Rescue of TTSuV2 from concatamerized TTSuV2 DNA of the clone pSC-TTV-US in CD/CD pigs. With the introduced genetic markers in the full-length DNA clones that can be used to distinguish between infections caused by the cloned virus and potential indigenous contaminating virus, the inventors performed an additional study in CD/CD pigs to further verify the in vivo infectivity of the TTSuV2 genomic DNA clones. Twelve CD/CD pigs were assigned into three groups with four pigs each. Pigs in each group were inoculated with PBS buffer, concatamerized "TTV2-EU DNA", and "TTV2-US DNA", respectively. Pre-inoculation serum samples for all pigs (collected at 30 days prior to inoculation) were tested negative for TTSuV1 or TTSuV2 DNA by real-time qPCR. Serum samples were collected from all animals at 0, 7, 14, 21, 28 and 35 DPI.

TTSuV2 DNA was detected in all eight inoculated pigs, but unfortunately, it was also detected in two negative control pigs, indicating contamination by other indigenous strains of TTSuV2 in the research facility or the source pigs, which is not uncommon. One pig (no. 133) inoculated with the concatamerized "TTV2-US DNA" had a detectable viremia even at 0 DPI, whereas the other pigs developed viremia at 14 or 21 DPI. Except for pig no. 133, the seven TTSuV2 DNA-inoculated pigs and the two TTSuV2-positive pigs in negative control group had an increased viral load until necropsy, indicating active virus infection. The inventors speculated that the source of the TTSuV2 contamination was likely due to the 1-month waiting period between the date of pre-inoculation serum sample testing (for which all animals were all negative) and 0 DPI.

However, thanks to the introduced genetic markers in the TTSuV2 DNA clones used in this study, the inventors were still able to determine if the TTSuV2 DNA clones were infectious in pigs, which was the main objective of our study. Since the inventors have previously demonstrated that a single pig can be infected by multiple strains of TTSuV2 and TTSuV1 (9, 17), then prior infection or concurrent infection of an indigenous TTSuV2 strain should not interfere with the infection of pigs by the TTSuV2 DNA clones the inventors intended to test in this study. To determine if the genetic markers of TTV2-EU or TTV2-US were present in viruses recovered from the sera of infected pigs under the mixed TTSuV2 infection status, the inventors amplified and sequenced a 620-bp region containing the engineered genetic markers from selected samples at 35 DPI from both inoculated and negative control pigs. The results showed that only the serum samples from pigs experimentally inoculated with the concatamerized "TTV2-US DNA" were found to have identical TTSuV2 sequences to the introduced genetic markers PstI and MfeI, whereas serum samples from the negative control group and from pigs inoculated with concatamerized "TTV2-EU DNA" did not contain any introduced genetic markers (data not shown). Therefore, this pig study further confirmed the initial pilot pig study that the TTSuV2-US full-length DNA clone is infectious in pigs. The results also experimentally verified, for the first time, that pigs can be co-infected by different strains of TTSuV2.

Little is known about the etiology and molecular biology of anelloviruses due to the lack of a cell culture system to propagate human TTV or TTSuV and the lack of a suitable animal model combined with reverse genetics systems for anellovirus studies. Reports of TTSuV DNA sequences detected in commercial porcine vaccine products, porcine-derived human drugs and in porcine-derived trypsin by nested PCR suggested a widespread contamination of TTSuV (Kekearainen, T., L. Martinez-Guino, and J. Segales. 2009. Swine torque teno virus detection in pig commercial vaccines, enzymes for laboratory use and human drugs containing components of porcine origin. J Gen Virol 90:648-53; Krakowka, S., S. S. Ringler, P. Arumugam, J. McKillen, K. McIntosh, C. Hartunian, A. Hamberg, M. Rings, G. Allan, and J. A. Ellis. 2008. Evaluation of *Mycoplasma hyopneumoniae* bacterins for porcine torque teno virus DNAs. Am J Vet Res 69:1601-7). Cell cultures may be one of the major sources for TTSuV contamination in biological products of pig origin. Therefore, the present study was first aimed at examining whether five selected cell lines harbor endogenous DNA and protein antigen of TTSuV1 or TTSuV2, and to further identify TTSuV-negative cell lines that are potentially permissive for TTSuV propagation.

Surprisingly, none of the five cell lines tested in the study were found to be positive for TTSuV1 or TTSuV2 DNA or ORF1 antigen (FIG. 2). Furthermore, screening of seven additional commonly-used cell lines also yielded negative results as determined by IFA detection, indicating that TTSuV contamination in cell cultures is probably not as common as the inventors originally thought. Our result was distinct from a recent study by a Brazilian group that reported TTSuV DNA contamination in 15 out of 25 cell lines (Teixeira, T. F., D. Dezen, S. P. Cibulski, A. P. Varela, C. L. Holz, A. C. Franco, and P. M. Roehe. 2011. Torque teno sus virus (TTSuV) in cell cultures and trypsin. PLoS One 6:e17501). In that study, the five cell lines that were also used here in our study, including PK-15, ST, BHK-21, Vero and MA-104 cells (from which the MARC-145 cell line is derived) had been shown to have detectable TTSuV1 and/or TTSuV2 sequences by using a one-round duplex PCR assay (Teixeira, T. F., D. Dezen, S. P. Cibulski, A. P. Varela, C. L. Holz, A. C. Franco, and P. M. Roehe. 2011. Torque teno sus virus (TTSuV) in cell cultures and trypsin. PLoS One 6:e17501). It is unclear why there is such a major discrepancy between our results in this study and those by the Brazilian group. A reliable approach to prove the presence of a contaminating virus in cell cultures used in biological products is to determine its susceptibility to virus infection, which has been exemplified by PCV1 (Beach, N. M., L. Cordoba, S. P. Kenney, and X. J. Meng. 2011. Productive infection of human hepatocellular carcinoma cells by porcine circovirus type 1. Vaccine 29:7303-6; Hattermann, K., C. Roedner, C. Schmitt, T. Finsterbusch, T. Steinfeldt, and A. Mankertz. 2004. Infection studies on human cell lines with porcine circovirus type 1 and porcine circovirus type 2. Xenotransplantation 11:284-94; Ma, H., S. Shaheduzzaman, D. K. Willliams, Y. Gao, and A. S. Khan. 2011. Investigations of porcine circovirus type 1 (PCV1) in vaccine-related and other cell lines. Vaccine 29:8429-37; Tischer, I., H. Gelderblom, W. Vettermann, and M. A. Koch. 1982. A very small porcine virus with circular single-stranded DNA. Nature 295:64-6). Theoretically, the possibility of TTSuV contamination in cell cultures is very low, since anellovirus has been shown to be extremely difficult to propagate in vitro. The present study utilized the (i) more sensitive qPCR assay (compared to the one-round PCR in the Teixeira et al study); (ii) the IFA; and (iii) transfection of circular TTSuV genomic DNA into the cells as the positive control (see below) to demonstrate the absence of TTSuV at both the DNA and amino acids levels in 12 representative cell lines including four of pig origin (PK-15, ST, 3D4/31 and IPEC-J2). Therefore, based on the results from this study, the inventors conclude that, contrary to what some may believe, there is very little, if any, endogenous TTSuV contamination in well-established continuous cell lineages. Instead, detection of contaminating TTSuV DNA sequences in biological products reported by other groups may come from the porcine-derived trypsin or serum (Kekearainen, T., L. Martinez-Guino, and J. Segales. 2009. Swine torque teno virus detection in pig commercial vaccines, enzymes for laboratory use and human drugs containing components of porcine origin. J Gen Virol 90:648-53; Teixeira, T. F., D. Dezen, S. P. Cibulski, A. P. Varela, C. L. Holz, A. C. Franco, and P. M. Roehe. 2011. Torque teno sus virus (TTSuV) in cell cultures and trypsin. PLoS One 6:e17501). The latter was actually confirmed in the present study for the first time (FIG. 2).

Figure 4:
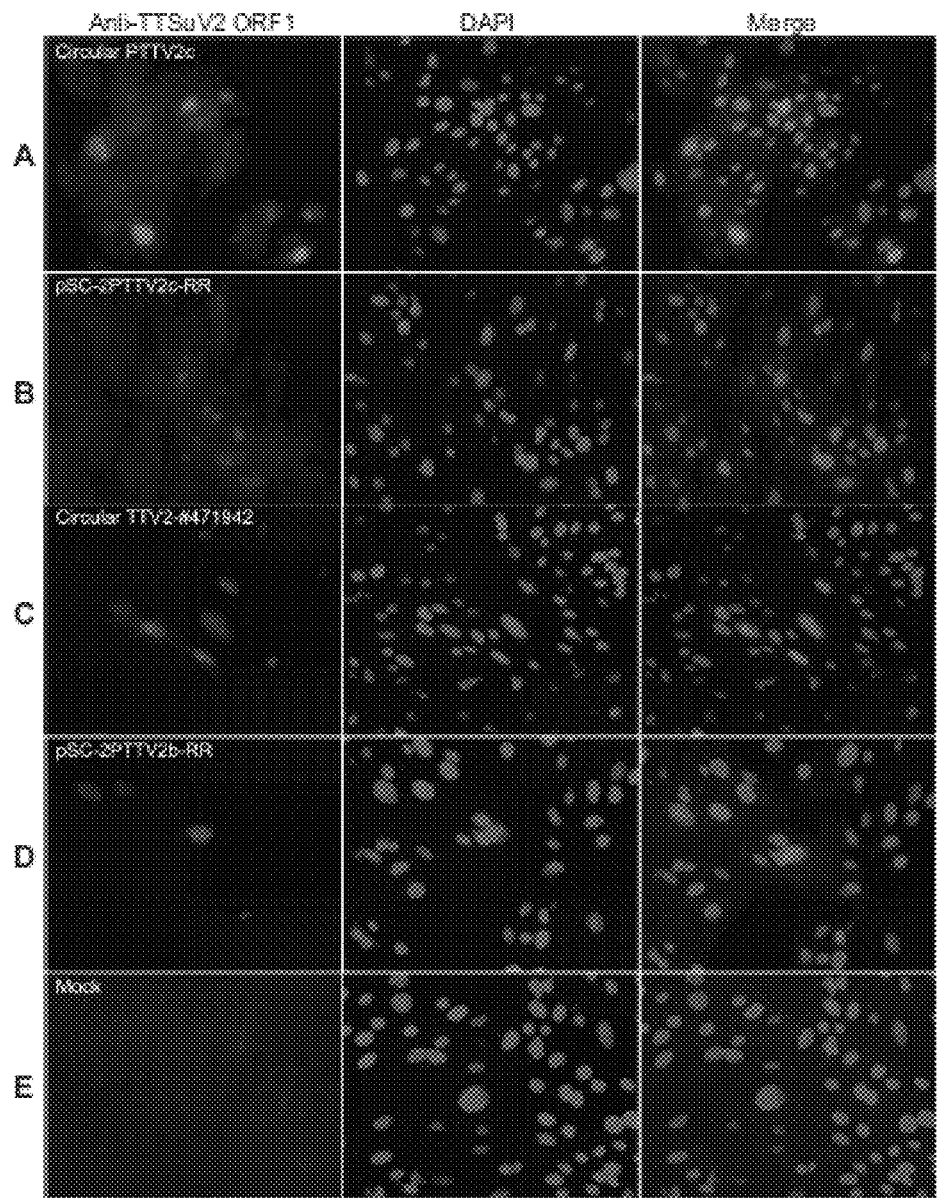
FIG. 4 illustrates Immunofluorescence assay (IFA) results on PCV1-free PK-15 cells transfected with the ligation mixtures of linear TTsuV2 genomic DNA derived from clones pSC-PTTV2c (A) or pSC-TTV2-#471942 (C), with plasmids pSC-2PTTV2c-RR (B) or pSC-2PTTV2b-RR (D), or with Lipofectamine LTX only (E). Cells were stained with a rabbit anti-TTsuV2 ORF1 polyclonal antibody (Ab) and a Texas Red-conjugated goat anti-rabbit IgG (red) at 5 days post-transfection (the left panels), DAPI (blue) was used to stain the cell nucleus (the middle panels). The Ab and DAPI stainings are merged (right panels). Magnification=200×.
Figure 6:
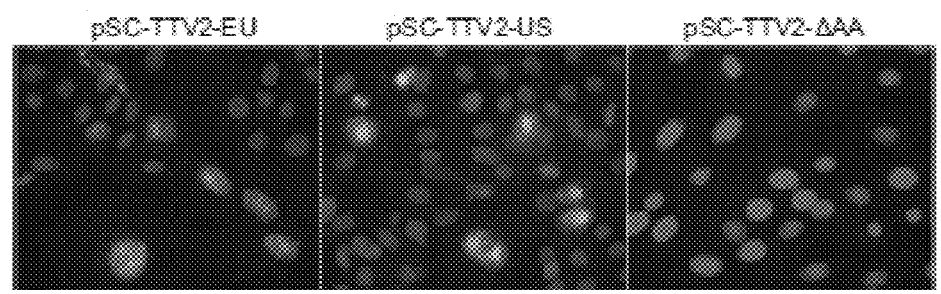
FIG. 6 illustrates IFA results of PCV1-free PK-15 cells transfected with the ligation mixtures of linear TTsuV2 genomic DNA derived from clones pSC-TTV2-EU, pSC-TTV2-US or pSC-TTV2-ΔAA. Cells were stained with an anti-TTsuV2 ORF1 antibody (Ab) and an Alexa fluor 488-conjugated goat anti-rabbit IgC (green) at 3 days post-transfection. DAPI (blue) was used to stain the cell nucleus. Only merge of Ab and DAPI stainings are shown. Magnification=200×.

Subsequently, the inventors demonstrated that all of these TTSuV-free cell lines supported TTSuV2 ORF1 expression by transfection with the circular TTSuV2 genomic DNA or the tandem-dimerized TTSuV2 plasmids (FIG. 4, FIG. 6 and FIG. 7). The TTSuV2 ORF1 protein was expressed in cell nuclei, especially in nucleoli, which is consistent with the localization of human TTV ORF1 in Huh-7 cells transfected with the circular full-length TTV genomic DNA by immunoblotting with the ORF1-specific antibody (Mueller, B., A. Maerz, K. Doberstein, T. Finsterbusch, and A. Mankertz. 2008. Gene expression of the human Torque Teno Virus isolate P/1C1. Virology 381:36-45). Most recently, it was also reported that TTSuV1 or TTSuV2 ORF1-GFP fusion protein expressed from the recombinant construct was accumulated in nucleoli of the PK-15 cells (Martinez-Guino, L., M. Ballester, J. Segales, and T. Kekarainen. 2011. Expression profile and subcellular localization of Torque teno sus virus proteins. J Gen Virol 92:2446-57).

In addition, in this study TTSuV2-specific roRNA splicing events were detected in transfected PK-15 cells by RT-PCR, indicating the synthesis of viral mRNA transcripts in the transfected cells. While the inventors experimentally demonstrated the existence of two viral mRNAs transcripts (mRNA2 and mRNA3) (FIG. 5), the putative mRNA 1 encoding the full-length ORF1 of TTSuV2 was not detected (data not shown), which may suggest a lower quantity and integrity of mRNA1 than that of mRNA2 and mRNA3. In accordance with the result described by Martinez-Guino et al., splicing of the 91-nt intron 2 sequence in mRNA3 also occurred in the post-transcription of TTSuV2 ORF1-GFP fusion gene based on none-full-length viral clone (Martinez-Guino, L., M. Ballester, J. Segales, and T. Kekarainen. 2011. Expression profile and subcellular localization of Torque teno sus virus proteins. J Gen Virol 92:2446-57).

The synthesis of viral mRNA transcripts and the subsequent expression of the ORF1 or ORF1-related viral proteins in transfected cells were driven by the endogenous TTSuV2 promoter. The processes were also regulated by the unidentified cis-acting elements, as we showed in this study that deletion of a 104-bp sequence downstream of the TATA box completely eliminated ORF1 expression (FIG. 6). To our knowledge, this is the first demonstration of porcine anellovirus viral mRNA and protein expression and mutagenesis analysis based on the viral DNA concatemers produced from circularized viral genomes or a tandem-dimerized full-length clone.

It appeared that both PTTV2c-VA and TTV2-#471942 DNA concatemers were replication-competent when transfected into cells since they mimicked the natural TTSuV2 circular genome. However, the rescue of PTTV2c-VA ("TTV2-US"), but not TTV2-#471942 ("TTV2-EU"), was only demonstrated in two in vivo animal experiments. The major sequence difference between these two TTSuV2 strains was in the GC-rich region. It has been proposed that the GC-rich region in anelloviruses forms unique stem-loop structures, which may play a significant role in viral replication (Miyata, H., H. Tsunoda, A. Kazi, A. Yamada, M. A. Khan, J. Murakami, T. Kamahora, K. Shiraki, and S. Hino. 1999. Identification of a novel GC-rich 113-nucleotide region to complete the circular, single-stranded DNA genome of TT virus, the first human circovirus. J Virol 73:3582-6; Okamoto, H., T. Nishizawa, M. Ukita, M. Taka hash i, M. Fukuda, H. Iizuka, Y. Miyakawa, and M. Mayumi. 1999. The entire nucleotide sequence of a TT virus isolate from the United States (TUS01): comparison with reported isolates and phylogenetic analysis. Virology 259:437-48). Further in-depth mutagenesis analysis, which was not the scope of the present study, is required to explain this discrepancy between the two clones.

The inventors also showed that, although the three cell lines (PK-15, ST and 293TT) tested in the study supported a limited level of TTSuV2 replication, the infection of these cells by TTSuV2, if any, was non-productive since the supernatants of the transfected cells did not induce a second-round infection. Most recently, the 293TT cell line was shown to be susceptible for human TTV propagation due to its expression of SV40 large T antigen at a high level (5). The authors proposed that the human TTV genome contains a conserved octanucleotide in the UTR forming a stem-loop as the putative origin of replication. Five 4-bp motifs (CGGG and GGGC) were found adjacent to the stem-loop, which may act as the recognition sites for the SV40 large T antigen to facilitate TTV replication (de Villiers, E. M., S. S. Borkosky, R. Kimmel, K. Gunst, and J. W. Fei. 2011. The diversity of torque teno viruses: in vitro replication leads to the formation of additional replication-competent subviral molecules. J Virol 85:7284-95). However, when the inventors performed a sequence alignment analysis of the corresponding sequences among human TTV, TTSuV, Torque teno canis virus (dog anellovirus) and Torque teno felis virus (cat anellovirus), neither the conserved octanucleotide nor the 4-bp motif was identified in the latter three anelloviruses (data not shown). Therefore, the SV40 large T protein expressed in 293TT cells likely does not provide the proposed helper effect on TTSuV replication. Further study is needed to screen whether additional cell lines are permissive to TTSuV2 infection.

Previous studies from our group and others have demonstrated that, even under strictly controlled experimental conditions in research facilities, TTSuV-negative pigs can easily acquire TTSuV infection due to the ubiquitous nature of this virus in pigs and environments (Gauger, P. C., K. M. Lager, A. L. Vincent, T. Opriessnig, M. E. Kehrli, Jr., and A. K. Cheung. 2011. Postweaning multisystemic wasting syndrome produced in gnotobiotic pigs following exposure to various amounts of porcine circovirus type 2a or type 2b. Vet Microbiol 153:229-39; Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). Although our second in vivo experiment in the present study unfortunately "validated" these previous reports, our results did demonstrate the successful rescue of TTSuV2 in pigs inoculated with either the tandem-dimerized plasmids or circular TTSuV2 DNA with the introduced genetic markers. Unfortunately, due to the presence of indigenous TTSuV2 in the CD/CD pigs from the second animal study, the inventors could not analyze or correlate any pathological lesions in the inoculated pigs to TTSuV infection. Therefore, a future study using the germ-free gnotobiotic pig and the infectious DNA clone is warranted to characterize the pathological lesions solely attributable to TTSuV2 infection. The availability of the pig model combined with the reverse genetics system of anellovirus described in this study will facilitate future studies of porcine and even human anellovirus biology and pathogenesis.

The family Anelloviridae includes human and animal Torque teno viruses (TTV) with extensive genetic diversity. The antigenic diversity among anelloviruses has never been assessed. Using Torque teno sus virus (TTSuV) as a model, the inventors describe here the first investigation on antigenic relationships among different anelloviruses. Using the TTSuV1a or TTSuV1b ELISA based on the respective recombinant ORF1 antigen and TTSuV1-specific real-time PCR, the combined serological and virological profile of TTSuV1 infection in pigs was determined and compared with that of TTSuV2. TTSuV1 is likely not associated with porcine circovirus associated disease since both the viral loads and antibody levels were not different between affected and unaffected pigs and since there was no synergistic effect of concurrent PCV2/TTSuV1 infections. The inventors did observe a higher correlation of IgG antibody levels between anti-TTSuV1a and -TTSuV1b than between anti-TTSuV1a or -1b and anti-TTSuV2 in these serum samples, implying potential antigenic cross-reactivity. To confirm this, rabbit antisera against the putative ORF1 capsid proteins of TTSuV1a, TTSuV1b or TTSuV2 were raised and the antigenic relationships and diversity among these TTSuVs were analyzed by ELISA. Additionally, antibody cross-reactivity was analyzed using PK-15 cells transfected with one of the three TTSuV ORF1 constructs. The results demonstrate antigenic cross-reactivity between the two genotypes, TTSuV1a and TTSuV1b, but not between the two species, TTSuV1a or 1b and TTSuV2. In addition, an anti-genogroup 1 human TTV serum did not react with any of the three TTSuV antigens. The results add to the knowledge base on diversity among anelloviruses and have important implications for diagnosis, classification and vaccine development of TTSuVs.

Expression and purification of the N-terminally truncated TTSuV1a and TTSuV1b ORF1 proteins. Previously the inventors had successfully expressed a truncated TTSuV2 ORF1 protein in E. coli (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). Using a similar strategy, the C-terminal region of the TTSuV1a-ORF1 or TTSuV1b-ORF1 gene with a C-terminally engineered 8×His-tag was inserted into the triple expression vector pTriEx1.1-Neo, resulting in two recombinant constructs, pTri-1aORF1 and pTri-1bORF1. The inventors also constructed an ORF1 C-terminally truncated version of 1b-ORF1 as a control, termed pTri-1bORF1-ctruc, which is 71-aa shorter than 1b-ORF1, to compare the size with that of pTri-1bORF1 in SDS-PAGE and WB analysis.

Figure 8:
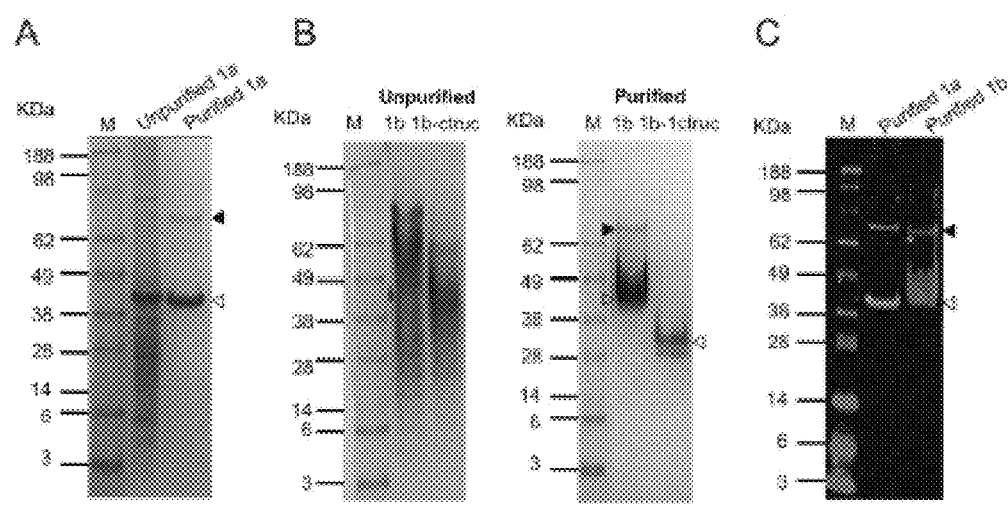
FIG. 8 illustrates expression and purification of the amino-terminaUy truncated TTsuV1a and TTsuV1b ORF1 proteins, respectively. (A) SDS-PAGE analysis of unpurified and purified TTsuV1a-ORF1 products. (B) SDS-PAGE analysis of unpurified and purified TTsuV1b-ORF1 products. An amino- and carboxyl-terminally double-truncated TTsuV1b-ORF1 (1b-ctruc) of smaller product size served as the control. (C) Near-infrared fluorescent WB analysis of purified 1a- and 1b-GRF1 products using an anti-His-tagged mAb. Open arrowheads indicate the truncated ORF1 protein of the expected size whereas filled arrowheads show the presumably homodimers of the expected proteins. M: protein markers.

The three recombinant proteins, 1a-ORF1, 1b-ORF1 and 1bORF1-ctruc were found to be insoluble and expressed within the bacteria as inclusion bodies. Purification of the crude lysates from 1a-ORF1 products with a nickel-affinity column resulted in visualization of two bands of ~40 KDa (white arrowheads) and ~70 KDa (black arrowheads), as analyzed by Coomassie blue staining (FIG. 8A). The ~40 KDa band is the expected product of the truncated 1a-ORF1 protein, whereas the ~70 KDa polypeptide is an unknown product but should be derived from the former since it also reacted with an anti-His-tagged Mab (see below). Expression of 1b-ORF1 or 1bORF1-ctruc showed a smear in the crude lysates (FIG. 8B). After purification, two bands of ~40 KDa and ~70 KDa, similar to 1a-ORF1, were also identified in the purified 1b sample, whereas only a ~30 KDa polypeptide (white arrowheads) was detected in the purified 1b-ctruc sample (FIG. 8B). The bands of ~40 KDa and ~30 KDa were consistent with the expected sizes of 1b-ORF1 and 1bORF1-ctruc protein products, respectively. All the identified polypeptides in the purified products were detected by WB using the anti-His-tagged Mab (FIG. 8C). The results indicated that both the truncated 1a-ORF1 and 1b-ORF1 proteins were successfully expressed in *E. coli* and thus can be used as antigens for TTSuV1a and TTSuV1b antibody detection in porcine sera.

Development of TTSuV1a- and TTSuV1b-based serum WB and indirect ELISAs. In order to identify reference positive and negative sera as controls, a total of 100 serum samples from different sources including those from the gnotobiotic pigs were collected. Samples were screened for anti-TTSuV1a or anti-TTSuV1b IgG seropositivity by serum WB analysis using the purified 1a-ORF1 or 1b-ORF1 as the antigens, respectively. A TTSuV2-seropositive and TTSuV1/TTSuV2-DNA positive porcine serum (Huang, Y. W., A. R. Patterson, T. Opriessnig, B. A. Dryman, A. Gallei, K. K. Harrall, E. M. Vaughn, M. B. Roof, and X. J. Meng. 2012. Rescue of a porcine anellovirus (Torque teno sus virus 2) from cloned genomic DNA in pigs. J. Virol. Submitted Manuscript) showed reactivity with the 1a-ORF1 and the 1b-ORF1 antigen, as the ~40 KDa band was presented in the WB analysis (FIG. 9A; two rightmost lanes). Therefore, this serum was considered to be TTSuV1a- and TTSuV1b-seropositive and thus was used as a reference positive control for the ELISAs. All the seven Virginia and 12 Iowa gnotobiotic pigs had no detectable TTSuV1a and TTSuV1b antibodies (FIG. 9A). Except for a few serum samples from conventional pigs from a Wisconsin swine farm (FIG. 9B; the two lanes on the left), the remaining samples were tested positive for both TTSuV1a and TTSuV1b antibodies by the WB analysis. The dual-negative serum samples from Wisconsin conventional pigs were pooled and used as a negative control reference serum.

With the available positive and negative control reference sera, TTSuV1a- and TTSuV1b-based ELISAs were subsequently developed and standardized, respectively. The concentrations of the purified 1a-ORF1 or 1b-ORF1 antigen, porcine sera and IgG conjugate were determined by a checkerboard titration assay to ensure low background signal and to give the highest difference of $OD_{450}$ values between the positive and negative controls. WB-negative gnotobiotic porcine sera showed very low OD values (<0.1) compared to the negative control reference serum (FIG. 9C), suggesting that these pig sera should not serve as a negative control reference for detection of porcine field samples in the ELISA test.

Association of TTSuV1 viral DNA loads and anti-TTSuV1a and anti-TTSuV1b IgG antibody levels. A total of 160 serum samples were collected and evaluated for the prevalence and viral DNA load of TTSuV1 by real-time qPCR and for seroprevalence and antibody levels (represented by S/N values) of anti-TTSuV1a and anti-TTSuV1b IgG by the ELISAs. Among the 160 samples, 138 sera in groups A to C were collected from three herds under field conditions whereas the remaining 22 sera in groups D (gnotobiotic pigs) and E were collected from pigs raised and housed under strictly controlled experimental conditions in research facilities.

None of the 12 TTSuV1a/TTSuV1b-seronegative gnotobiotic pigs in group D had a detectable viremia. In group E pigs, only one pig was viremic whereas six were seropositive for TTSuV1a and among them, one pig was also seropositive for TTSuV1b.

Figure 10:
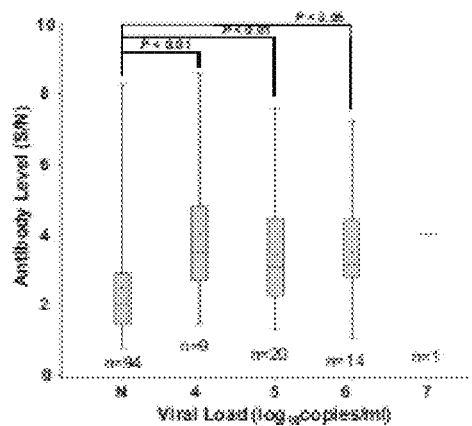
FIG. 10 illustrates serological and virological profiles of TTSuV1 infection in 138 sera of pigs from three different herds. (A) Distribution of TTsuV1 viremia, anti-TTsuV1a and anti-TTsuV1b IgG among 138 serum samples. Box-and-Whisker-plots of TTsuV1a (B) and TTsuV1b (C) serum antibody level by TTSuV1 viral DNA load. N: Negative. The detection limit of the TTSuV1 real-time qPCR was 4 log$_{10}$ copies/ml in this study.
Figure 10:
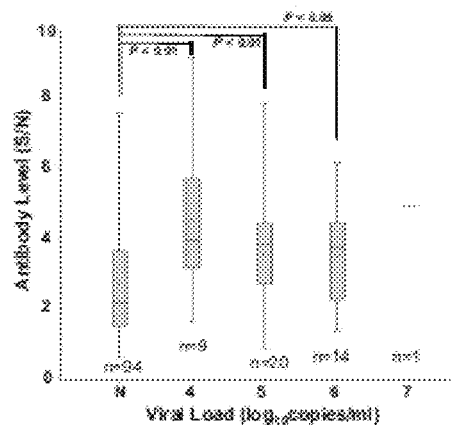

In groups A and C, 44 of 138 pigs were viremic (31.9%) whereas 128 were TTSuV1a-seropositive (92.8%) and 121 were TTSuV1b-seropositive (87.7%) (FIG. 10A). The incidence of TTSuV1 viremia was much lower than the TTSuV1a or 1b seropositive rate, suggesting previous clearance of the virus by neutralizing antibodies during the post-TTSuV1 infection convalescent period. Similar to the previously obtained results for TTSuV2 (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88), pigs with undetectable TTSuV1 viral DNA load were more likely to have lower levels of TTSuV1a and TTSuV1b antibody titers than pigs with TTSuV1 viral DNA load at the levels of $10^4$ to $10^6$ copies/ml (p<0.05) in these three groups (FIGS. 10B & 10C).

All three markers of TTSuV1 infection, TTSuV1 DNA and TTSuV1a/1b antibodies, were found in 40 serum samples. Notably, the number of pigs that were TTSuV1a/TTSuV1b-dually seropositive but viral DNA-negative (77 samples) was higher than that of pigs with TTSuV1a- or TTSuV1b-seropositivity only (FIG. 10A). In addition, the total number of porcine sera with both antibodies was 117 (40+77) among the 138 serum samples, implying that (i) co-infection rates of pigs with TTSuV1a and TTSuV1b are high, which was expected; and (ii) a certain degree of cross-reactivity may exist between anti-TTSuV1a and anti-TTSuV1b IgG antibodies.

The inventors had previously demonstrated that, over a two-month period, the 10 group-A pigs had decreasing TTSuV2 viral loads that were associated with elevated anti-TTSuV2 ORF1 IgG antibody levels (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). Whether an analogous situation for TTSuV1 in these ten pigs existed was subsequently analyzed in this study, by comparing the TTSuV1 viral DNA loads and the anti-TTSuV1a or anti-TTSuV1b antibody levels in sera from the time of their arrival until two months later. Five of ten pigs were TTSuV1 DNA negative during the two months, and in four pigs (ID#4314, 4316, 4319 and 4321) the viral DNA loads decreased after two months, including in 3 pigs (ID#4314, 4319 and 4321) with no detectable TTSuV1 DNA (FIG.

11A). In contrast, both the anti-TTSuV1a and anti-TTSuV1b antibody titers increased in all 10 pigs (FIGS. 11B & 11C). These results were consistent with those of the TTSuV2 study.

Figure 12:
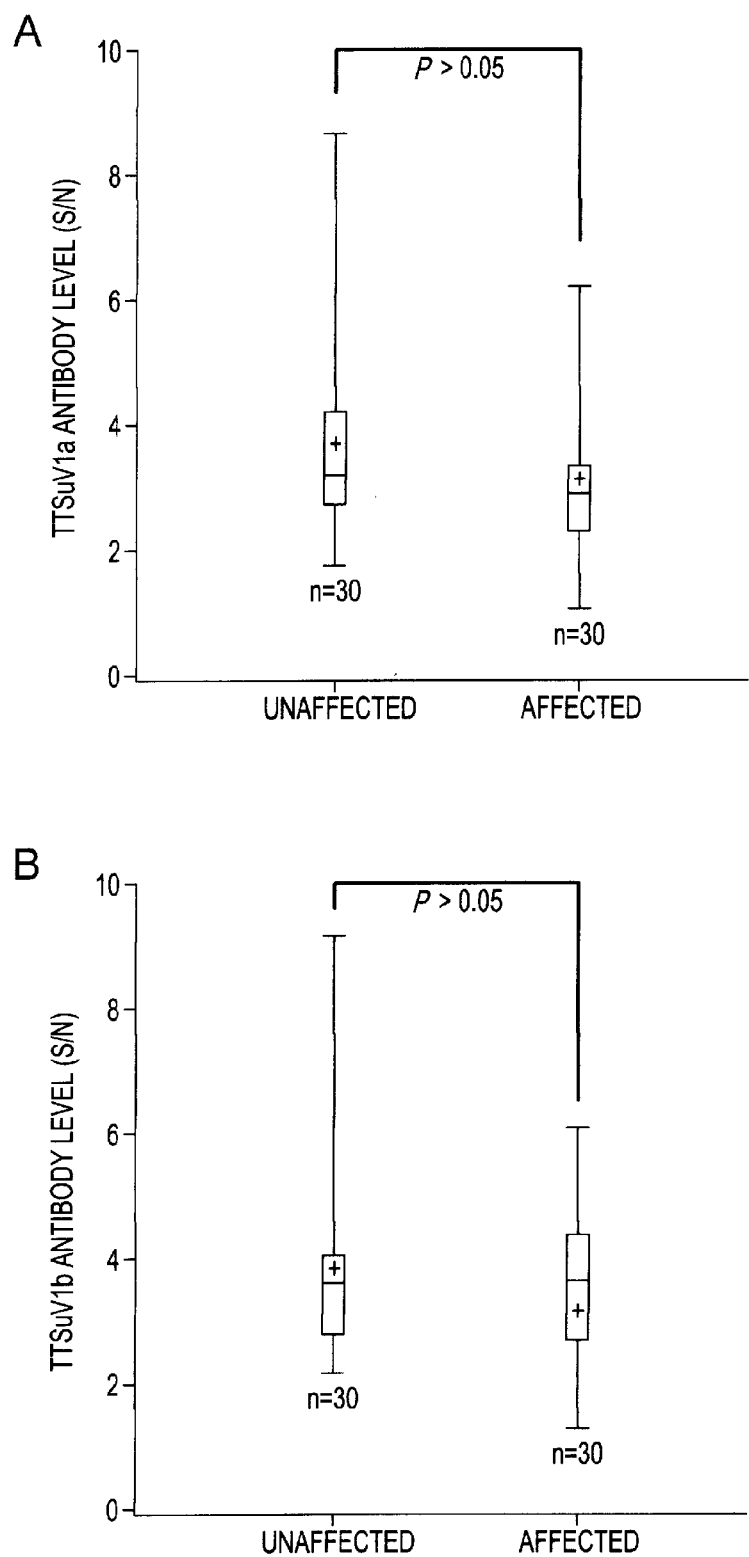
FIG. 12 illustrates box plots showing the comparisons of anti-TTSuV1a (A) or anti-TTSuV1b (B) ORF1 antibody levels and TTSuV1 (C) or PCV2 (D) viral loads between the PCVAD-affected and -unaffected pigs.
Figure 12:
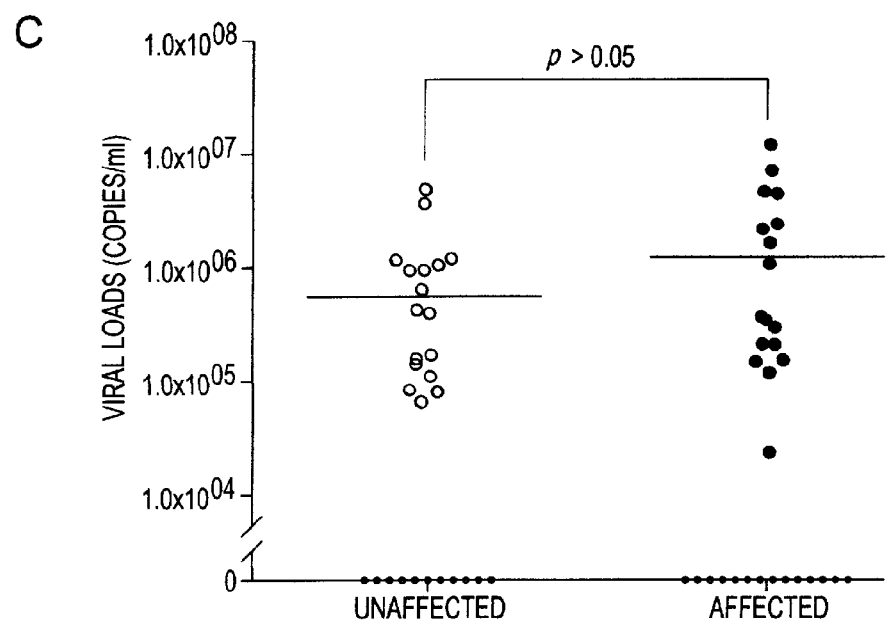
Figure 12:
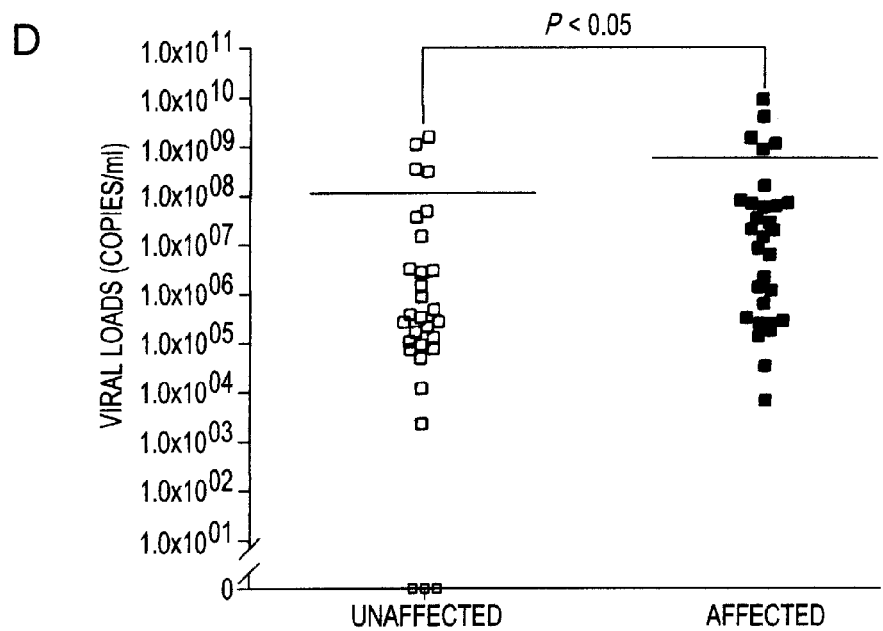

TTSuV1 is likely not associated with PCVAD. The inventors had previously found that PCVAD-affected pigs had a significantly lower level of TTSuV2 antibody than PCVAD-unaffected pigs in group B (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). However, determination of the levels of anti-TTSuV1a and anti-TTSuV1b IgG antibodies in these serum samples did not reveal a difference between the PCVAD-affected and -unaffected pigs (FIGS. 12A & 12B). In addition, there was no statistically significant difference of TTSuV1 viral loads between the PCVAD-affected and -unaffected pigs (FIG. 12C). In contrast, PCV2 viral load was significantly higher ($p<0.05$) in PCVAD-affected pigs compared to PCVAD-unaffected pigs (FIG. 12D).

The inventors further analyzed whether there existed a PCV2 and TTSuV1 synergistic effect associated with PCVAD. Serum viral DNA prevalence rates (viremia) of PCVAD-affected pigs were as follows: 50% (16/32) for PCV2 and TTSuV1, 56% (14/25) for PCV2 only, 0% (0/1) for TTSuV1 only, and 0% (0/2) for no detectable virus. These proportions were not significantly different ($p=0.4339$). The above results suggested that TTSuV1 is likely not associated with PCVAD.

Comparison and correlations of seroprevalence and antibody levels among anti-TTSuV 1a, anti-TTSuV1b and anti-TTSuV2. Mixed infections of TTSuV1 and TTSuV2 are common in pigs, as determined by the presence of viral DNA of both TTSuV1 and TTSuV2 in the same pig using PCR (Gallei, A., S. Pesch, W. S. Esking, C. Keller, and V. F. Ohlinger. 2010. Porcine Torque teno virus: determination of viral genomic loads by genogroup-specific multiplex rt-PCR, detection of frequent multiple infections with genogroups 1 or 2, and establishment of viral full-length sequences. Vet Microbiol 143:202-12; Huang, Y. W., B. A. Dryman, K. K. Harrall, E. M. Vaughn, M. B. Roof, and X. J. Meng. 2010. Development of SYBR green-based real-time PCR and duplex nested PCR assays for quantitation and differential detection of species- or type-specific porcine Torque teno viruses. J Virol Methods 170:140-6; Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88; Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:289-97). In this study, the inventors provided the serological evidence to support this conclusion by analyzing the seroprevalence distribution of anti-TTSuV1a, -TTSuV1b and -TTSuV2 IgG in the 138 serum samples in groups A-C. As shown in FIG. 6A, 82 of 138 serum samples were triple-seropositive, indicating that these pigs had been infected by TTSuV1 (TTSuV1a and/or TTSuV1b) and TTSuV2.

Figure 13:
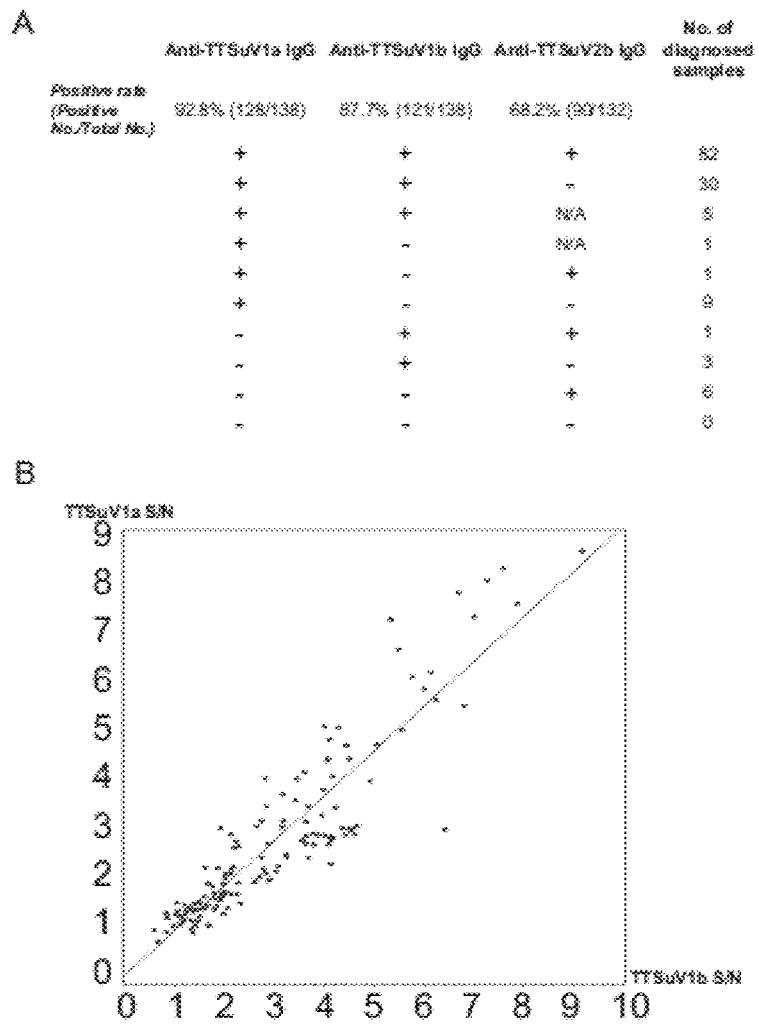
FIG. 13 illustrates a high correlation between anti-TTSuV1a and anti-TTSuV1b IgG in 138 serum samples. (A) Distribution of anti-TTSuV1a, -TTSuV1b and -TTSuV2 IgG. (B) Scatter plots showing a good linear relationship of antibody level between anti-TTSuV1a and anti-TTSuV1b (p<0.0001).

The distribution of dual seropositive samples was significantly different. A total of 117 (82+30+5) porcine sera were dually-seropositive for both anti-TTSuV1a and anti-TTSuV1b, which was consistent with the number calculated in FIG. 10A. In contrast, dual seropositivity to anti-TTSuV1a and anti-TTSuV2, or to anti-TTSuV1b and anti-TTSuV2, each occurred in only one sample (FIG. 13A).

Furthermore, correlations of antibody levels between anti-TTSuV1a and anti-TTSuV 1b, between anti-TTSuV1a and anti-TTSuV2, and between anti-TTSuV1b and anti-TTSuV2 were assessed in the 138 serum samples by using Spearman's correlation coefficient. A good linear relationship was observed between the anti-TTSuV1a and anti-TTSuV1b (FIG. 13B; Spearman's rank correlation coefficient=0.91, $p<0.0001$). When all the 160 samples were included, a better agreement was obtained (Spearman's rank correlation coefficient=0.93, $p<0.0001$). A lesser degree of correlation between anti-TTSuV1a and anti-TTSuV2 or between anti-TTSuV1b and anti-TTSuV2 was found when compared to that between anti-TTSuV1a and anti-TTSuV1b (data not shown). The results further revealed an association of seroprevalence and antibody levels between anti-TTSuV1a and anti-TTSuV1b, and thus it is logical to hypothesize that there exists an antigenic cross-reactivity between the two TTSuV1a and TTSuV1b genotypes.

Figure 14:
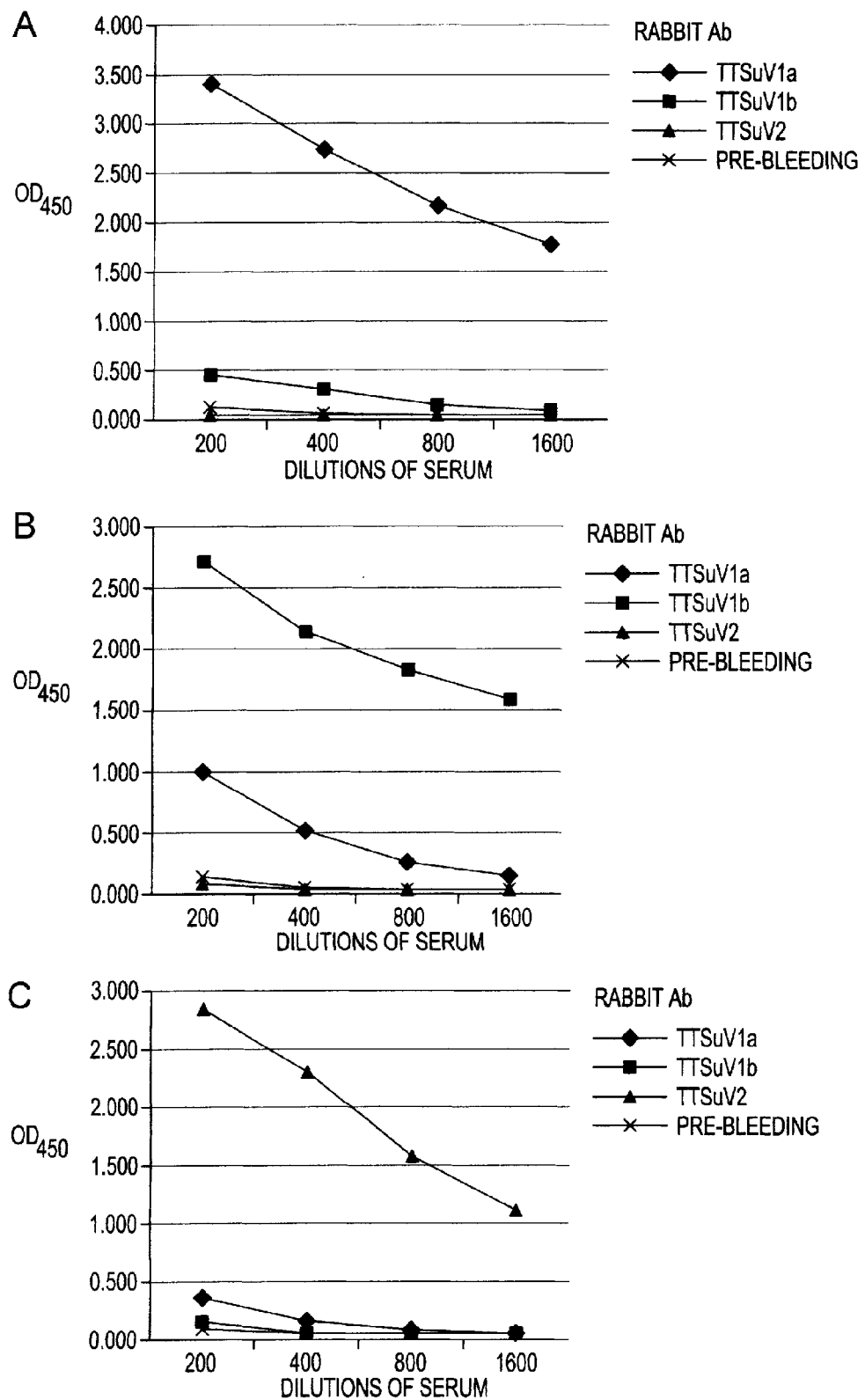
FIG. 14 illustrates reactivity of the three purified TTSuV ORF1 antigens: TTSuV1a (A), TTSuV1b (B) and TTSuV2 (C) with rabbit antisera against ORF1s of TTSuV1a, TTSuV1b or TTSuV2 or with pre-bleed rabbit serum with 2-fold serial dilutions by ELISAs. Each antigen was tested in duplicate against each serum sample. Mean OD values are presented.

Analysis of antigenic relationships among TTSuV1a, TTSuV1b and TTSuV2 by ELISA. Three antisera against the truncated recombinant ORF1s of TTSuV1a, TTSuV1b or TTSuV2 were raised by immunization of rabbits with the respective purified recombinant antigen. Cross-immunoreactivity studies were initially performed to assess whether one of these antigens could cross-react with antisera against the other two antigens in an ELISA format. The pre-bleed rabbit serum was used as the negative control. As expected, each of three TTSuV antigens reacted with its corresponding homologous antiserum but not with the pre-bleed negative control serum (OD values<0.1) that were serially diluted from 1:200 to 1:1600 (FIG. 14A-14C).

The TTSuV2 antigen did not appear to cross-react with TTSuV1a or TTSuV1b antiserum even at 1:200 dilution since the OD value was relatively low (FIG. 14C). In contrast, the TTSuV1b antigen did cross-react with the anti-TTSuV1a serum (as shown at 1:200 and 1:400 dilutions, both OD values>0.5) but not with the anti-TTSuV2 serum (FIG. 14B) whereas the TTSuV1a antigen likely cross-reacted with the anti-TTSuV1b serum (at 1:200 dilution) but not with the anti-TTSuV2 serum (FIG. 14A). The ELISA results strongly supported our hypothesis that there is an antigenic cross-reactivity between the two TTSuV1a and TTSuV1b genotypes but not between the two species TTSuV1a or 1b and TTSuV2.

Figure 15:
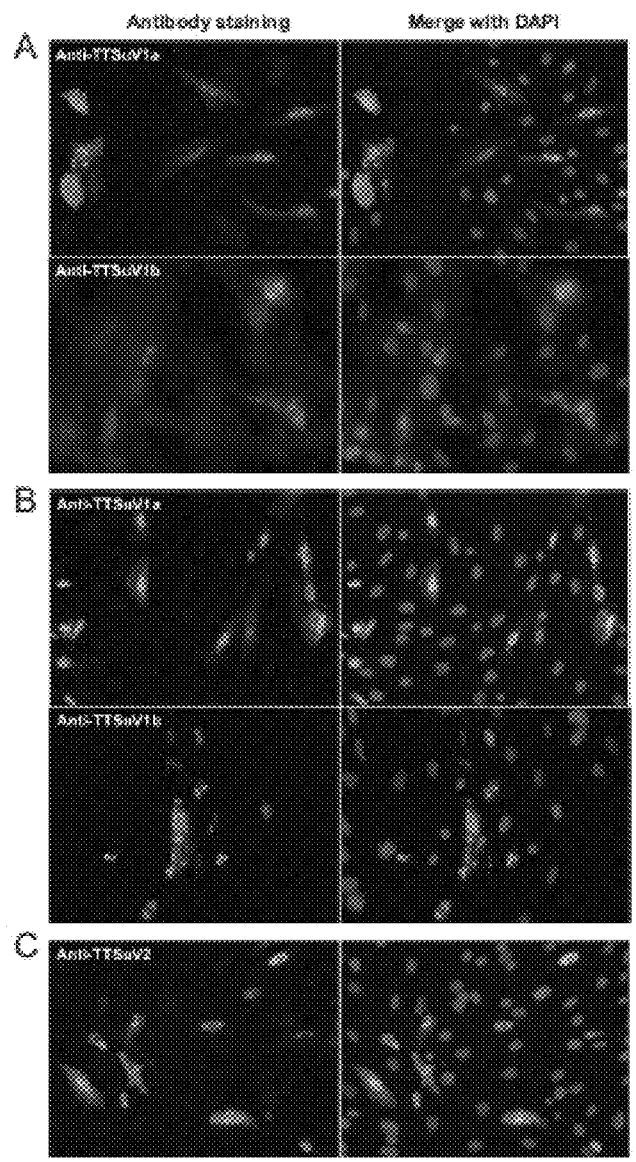
FIG. 15 illustrates Immunofluorescence assay (IFA) results of PCV1-free PK-15 cells transfected with the plasmids pTri-1aORF1 (A), pTri-1bORF1 (B) or pTri-2cORF1 (C) at 3 days post-transfection. pTri-1aORF1- or pTri-1bORF1-transfected cells were stained with the rabbit anti-TTSuV1a and -TTSuV1b ORF1 antiserum, respectively, whereas pTri-2cORF1-transfected cells were stained with the rabbit anti-TTSuV2 ORF1 antiserum. The Alexa fluor 488-conjugated goat anti-rabbit IgG was used as the secondary Ab in IFA (all the left panels). Ab staining merged with nuclear staining using DAPI (blue) are shown in the right panels. Magnification=200×.

Demonstration of antigenic relationships among TTSuV1a, TTSuV1b and TTSuV2, and between TTSuVs and a genogroup 1 human TTV by IFA. In order to definitely analyze the antigenic cross-reactivity among these viruses, an antibody cross-reactivity experiment was performed by using IFA staining. PK-15 cells were transfected with three plasmid constructs, pTri-1aORF1, pTri-1bORF1 and pTri-2cORF1, which harbor the truncated ORF1 capsid genes from TTSuV1a, TTSuV1b and TTSuV2, respectively. Three days post-transfection, cells were stained with anti-TTSuV1a, anti-TTSuV1b, anti-TTSuV2 and pre-bleed serum, respectively. As shown in FIG. 15, cells transfected with pTri-1aORF1 (FIG. 15A) or pTri-1bORF1 (FIG. 15B) stained positive with both anti-TTSuV1a and anti-TTSuV1b but not with the anti-TTSuV2 or the pre-bleed serum (data not shown), whereas cells transfected with pTri-2cORF1 only reacted with anti-TTSuV2 serum (FIG. 15C). Each TTSuV1 antiserum reacted stronger with its own homologous antigen than the heterologous antigen based on comparison of the positive cell numbers and fluorescence intensity (FIGS. 15A and 15B). The truncated ORF1s were expressed in both nuclei and cytoplasm of the transfected cells (FIG. 15), which was different from what we found in cells transfected with full-length TTSuV DNA clones (15), probably due to the lack of most of the putative nuclear localization signals (NLS) located at the N-terminal part of the ORF1 in the truncated genes (computer analysis; data not shown). Table 1 summarizes the results of the cross-reactive immunostaining study. In addition, when transfected cells were each stained with an anti-human genogroup 1 TTV ORF1 antiserum (AK47; raised in rabbits), no fluorescent signal was detected. Mock-transfected cells did not stain with any of the five antisera (Table 1). The IFA result further confirmed the presence of antigenic cross-reactivity between TTSuV1a and TTSuV1b as shown by the ELISA but not between the TTSuV1a or 1b and TTSuV2. The results also revealed that there was no antigenic cross-reactivity between genogroup 1 human TTV and porcine anelloviruses.

Identification of two putative antigenic sites on the ORF1 shared by TTSuV1a and TTSuV1b by sequence analyses. The full-length ORF1 proteins between TTSuV1 and TTSuV2 shared only 22.4-25.8% amino acid (aa) sequence identity with no significantly conserved regions identified (14). The ORF1 proteins of the two TTSuV species share only 19.1-21.0% aa sequence identity with that of the human genogroup 1 TTV isolate P/1C1 (GenBank accession no. AF298585). The high ORF1 sequence divergences between TTSuV1 and TTSuV2 and between porcine and human anelloviruses likely account for the absence of antigenic cross-reactivity observed in this study.

Figure 16:
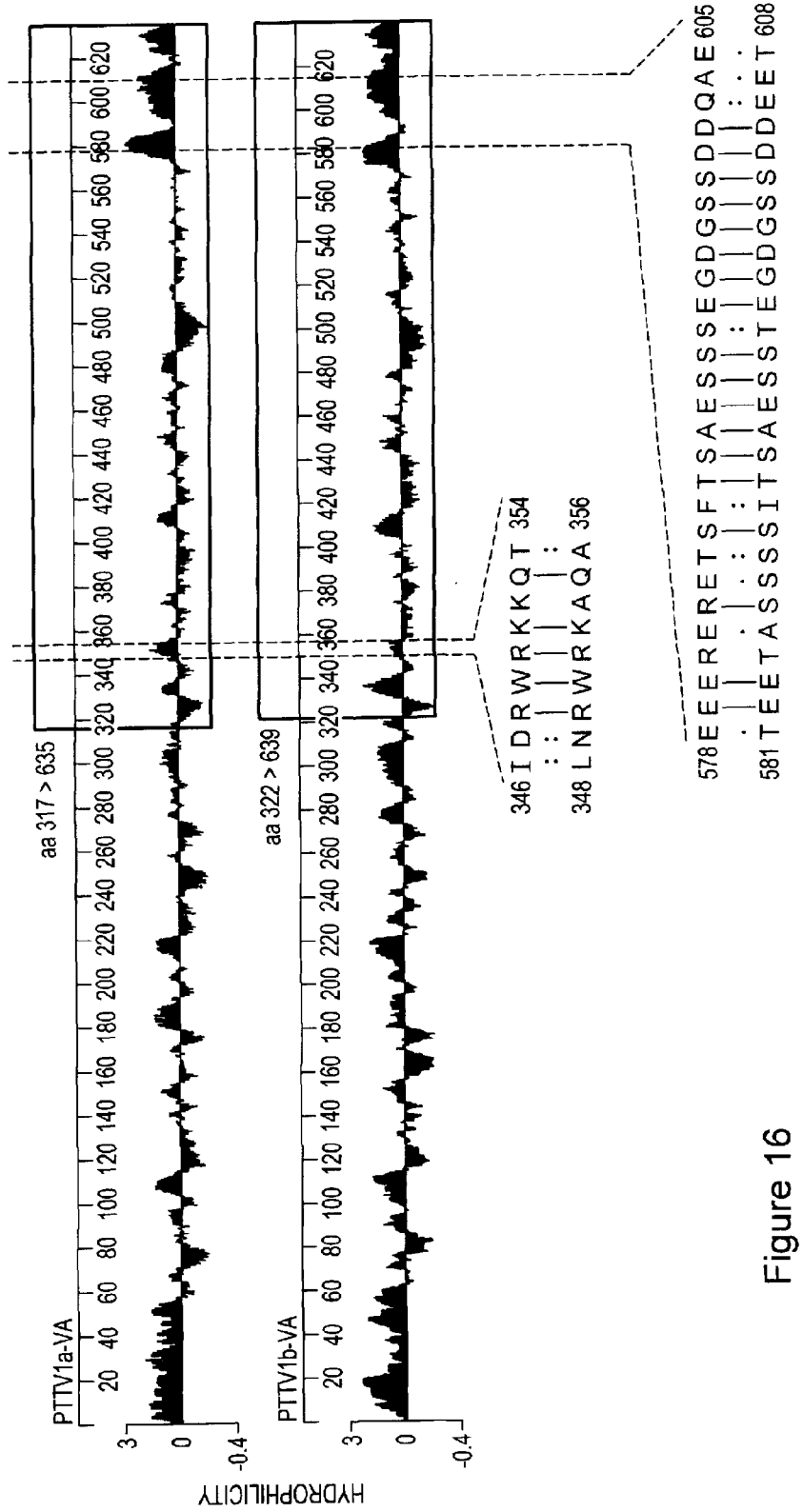
FIG. 16 illustrates comparison of hydrophilicity profiles of TTSuV1a (PTTV1a-VA strain (SEQ ID NO:12)) and TTSuV1b (PTTV1 b-VA strain (SEQ ID NO:13)) ORF1 and identification of two putative common antigenic domains in ORF1 of TTSuV1. The C-terminal region used for the expression of the truncated 1a- or 1b-ORF1 is indicated by a box. The corresponding alignment of amino acid (aa) sequences and aa positions of the two domains are also shown. Favorable mismatches of the aa were displayed as colons whereas neutral mismatches are depicted as periods.

However, the aa sequence identity of ORF1 between the two TTSuV1a and TTSuV1b genotypes (six isolates available in GenBank) ranged between 49.4-52.4%. The inventors have previously found that conserved sites exist in the ORF1 of different TTSuV1 stains except for the four proposed variable regions (30.0-37.5% aa identity) (Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:289-97). In order to identify the common antigenic sites on the ORF1 between the genotypes TTSuV1a and TTSuV1b, the inventors performed a comparative analysis of hydrophilicity profiles of the ORF1 aa sequences between PTTV1a-VA and PTTV1b-VA. Two conserved hydrophilic regions located at the middle and C-terminal regions were identified (FIG. 16). The C-terminal antigenic domain appeared to be more antigenic than the domain in the middle region. Alignment of the two putative antigenic regions among all published TTSuV1 sequences revealed a high degree of sequence conservation (data not shown).

The immunology of anellovirus is poorly understood (20). Detection of specific adaptive immune responses can provide insights into anellovirus epidemiology. By analogy to the chicken anemia virus (CAV), another single-stranded circular DNA virus, the ORF1 product of anelloviruses is believed to function as the putative capsid protein and thus represents the major viral antigen (Crowther, R. A., J. A. Berriman, W. L. Curran, G. M. Allan, and D. Todd. 2003. Comparison of the structures of three circoviruses: chicken anemia virus, porcine circovirus type 2, and beak and feather disease virus. J Virol 77:13036-41; Maggi, F., and M. Bendinelli. 2009. Immunobiology of the Torque teno viruses and other anelloviruses. Curr Top Microbiol Immunol 331:65-90).

Detection of human TTV IgG antibodies in human populations based on the human TTV ORF1 as the antigen has been reported (Maggi, F., and M. Bendinelli. 2009. Immunobiology of the Torque teno viruses and other anelloviruses. Curr Top Microbiol Immunol 331:65-90). Handa et al reported a 38% prevalence of human TTV antibody among 100 American blood donors when using the N-terminal part (aa 1-411) containing the arginine-rich region of ORF1 of a human genotype 1b TTV isolate as the antigen (Handa, A., B. Dickstein, N. S. Young, and K. E. Brown. 2000. Prevalence of the newly described human circovirus, TTV, in United States blood donors. Transfusion 40:245-51). In contrast, antibody reactivity in humans to the N-terminus of ORF1 (ORF1-N) of a human TTV genotype 6 was not detected by a Finish group. After removal of the arginine-rich region (aa 1-62), the arginine-deleted constructs (ORF1AArg and ORF1-NAArg) as well as the C-terminal portion (ORF1-C; aa 344-737) were expressed, 48% human TTV IgG prevalence was detected in sera of 21 healthy Finnish adults using the three products as the antigens (Kakkola, L., H. Bonden, L. Hedman, N. Kivi, S. Moisala, J. Julin, J. Yla-Liedenpohja, S. Miettinen, K. Kantola, K. Hedman, and M. Soderlund-Venermo. 2008. Expression of all six human Torque teno virus (TTV) proteins in bacteria and in insect cells, and analysis of their IgG responses. Virology 382:182-9). Two other groups also utilized similar strategies targeting the C-terminal region to successfully express human TTV ORF1. Muller et al demonstrated that an ORF1-specific antiserum against the C-terminal part of ORF1 (aa 402-733) of the human TTV isolate P/1C1 generated in a rabbit was able to detect ORF1 expression in cell culture (21), whereas a French group reported the detection of anti-human TTV ORF1 IgG antibodies in 69 of 70 French subjects including 30 blood donors, 30 cryptogenic hepatitis patients and 10 healthy children using an ORF1 C-terminus-based WB analysis (Ott, C., L. Duret, I. Chemin, C. Trepo, B. Mandrand, and F. Komurian-Pradel. 2000. Use of a TT virus ORF1 recombinant protein to detect anti-TT virus antibodies in human sera. J Gen Virol 81:2949-58). Most recently, our group successfully used the C-terminal fragment of the ORF1 protein of a U.S. strain of TTSuV2 as the antigen to detect TTSuV2-specific IgG antibodies in pig sera by ELISA (13). Together with the present study for serological detections of the two porcine TTV species-1 genotypes TTSuV1a and TTSuV1b, the obtained data suggest that the C-terminal portion of ORF1 of anelloviruses is an appropriate target for the development of serodiagnostic assays.

Indeed, based on the CAV virion structure determined by cryo-electron microscopic images, the C-terminal half portion of the ORF1 is proposed to form the outer part of the capsid that is exposed to the virion surface whereas the basic N-terminal part of the CAV ORF1 is proposed to be inside the capsid to bind the viral DNA, and the middle part of the ORF1 is proposed to form the inner shell of the capsid (Crowther, R. A., J. A. Berriman, W. L. Curran, G. M. Allan, and D. Todd. 2003. Comparison of the structures of three circoviruses: chicken anemia virus, porcine circovirus type 2, and beak and feather disease virus. J Virol 77:13036-41). The ORF1 polypeptide of anellovirus has been suggested to be organized in the same way as that of CAV (Crowther, R. A., J. A. Berriman, W. L. Curran, G. M. Allan, and D. Todd. 2003. Comparison of the structures of three circoviruses: chicken anemia virus, porcine circovirus type 2, and beak and feather disease virus. J Virol 77:13036-41). This proposed structure is consistent with the computer analysis of the ORF1 hydrophilicity profiles of TTSuV1 (FIG. 16) and TTSuV2 (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). In either case, there are two conserved major hydrophilic regions located at the middle and C-terminal regions that span the C-terminal half portion of the ORF1.

Figure 9:
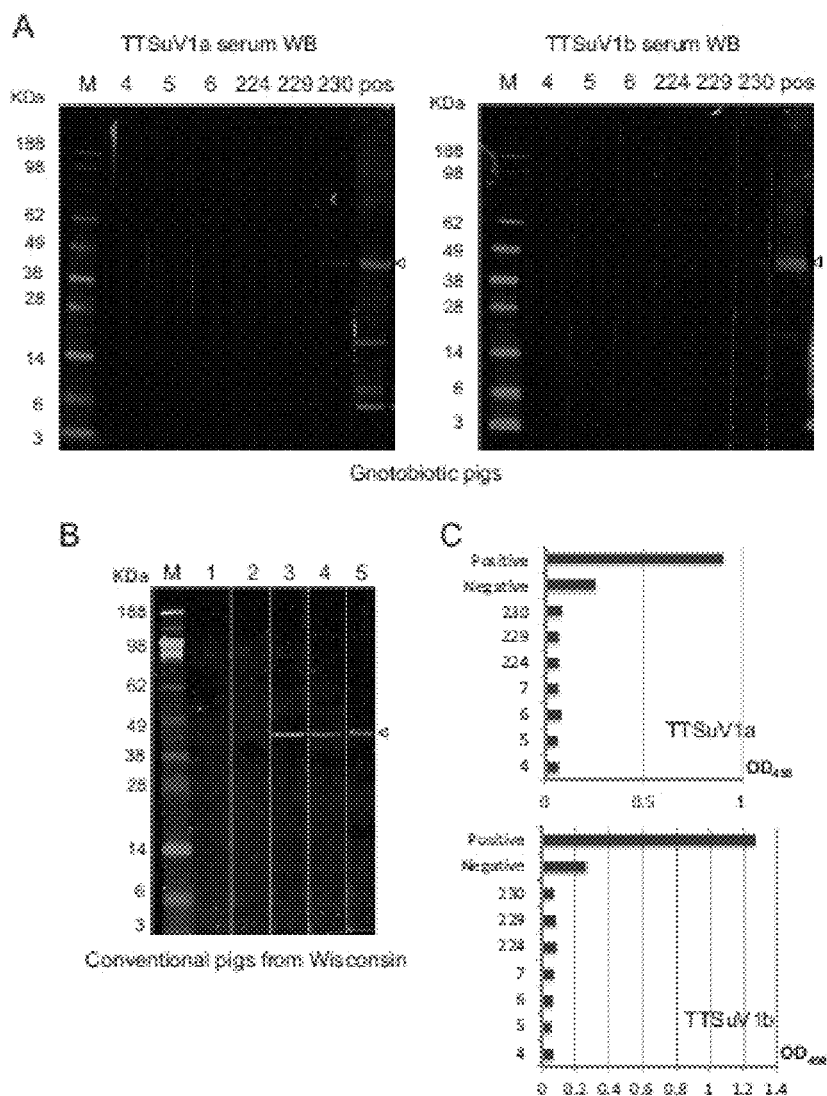
FIG. 9 illustrates TTsuV1a or TTsuV1b serum WB and ELISA. (A) WB analyses using the gnotobiotic pig serum samples from Virginia and a commercial OIE diseases-free porcine serum as the positive control reference serum (pos). (B) Representative results of TTsuV1a WB analyses of conventional pig sera from a farm in Wisconsin. Purified 1a-ORF1 protein was used as the antigen. Sera tested negative for both TTsuV1a and TTsuV1b antibodies by WB were pooled and used as the negative control reference serum. Open arrowheads indicate the truncated ORF1 protein of expected size. Only the bands in green color were considered as positive. M: protein markers. (C) TTsuV1a or TTsuV1b ELISA results of the seven Virginia gnotobiotic pig serum samples, positive and negative control reference sera.

Reliability and specificity of the established ELISAs for differential TTSuVs antibody detections were guaranteed by screening of the positive and negative reference sera through a serum WB. It was further demonstrated by triple seronegativity of TTSuV1a, TTSuV1b and TTSuV2 in gnotobiotic pigs of group D (FIG. 9). A high seropositive rate of TTSuV1a (92.8%) or TTSuV1b (87.7%) was revealed in the 138 groups A-C pigs (FIG. 10A), which was higher than that of TTSuV2 (~60%) (13), indicating a wider spread of actual TTSuV1 infection or the presence of long-persisting anti-TTSuV1 ORF1 antibodies in these pigs regardless of a low incidence of TTSuV1 viremia. Accordingly, these results, for the first time, provided serological evidence supporting multiple infections of TTSuV1a, TTSuV1b and TTSuV2 in the same pigs. To our knowledge, this is also the first study demonstrating multiple anellovirus infections in the same animals by using serological diagnosis in addition to the PCR assay. Therefore, the subsequent question raised was to determine the specificity of seropositivity and cross-antigenic reactivity among different TTSuV species and genotypes.

In this study, the inventors demonstrated by investigating four different aspects that indeed there exists antigenic cross-reactivity between the two TTSuV1a and TTSuV1b genotypes but not between the two TTSuV species (TTSuV1a or 1b and TTSuV2). First, when compared to the serum samples with single TTSuV1a- or TTSuV1b-seropositivity, the numbers of serum samples with TTSuV1a/1b-dual seropositivity was much higher (FIG. 10A), likely implying a certain degree of cross-antigenic reactivity between TTSuV1a and TTSuV1b antibodies. Secondly, the number of serum samples with dual TTSuV1a and TTSuV1b seropositivity was significantly higher than that of dual seropositivity to TTSuV1a and TTSuV2, or to TTSuV1b and TTSuV2 (FIG. 13A). In addition, a high correlation of antibody levels between anti-TTSuV1a and anti-TTSuV1b as assessed by Spearman's correlation coefficient was observed (FIG. 13B). These analyses were conducted under the background of multiple TTSuV infections in field samples, which led us to propose a logical hypothesis regarding the presence of an antigenic cross-reactivity between TTSuV1a and TTSuV1b. Thirdly, this hypothesis was experimentally confirmed by analysis of the antigenic relationships among TTSuV1a, TTSuV1b and TTSuV2 through antigen-specific ELISAs (FIG. 14), and antibody cross-reactivity studies in PK-15 cells transfected with the three TTSuV ORF1 constructs, respectively (FIG. 15 and Table 1). Finally, sequence comparison of ORF1 of the TTSuV also supported the observed epidemiologic and experimental data in this study: while there was no significant sequence homology of TTSuV1a or 1b ORF1 with that of TTSuV2, the inventors identified two putative antigenic sites on the ORF1 that are shared by TTSuV1a and TTSuV1b (FIG. 16).

In addition, in this study the inventors also demonstrated the absence of antigenic cross-reactivity between TTSuVs and a human genogroup 1 TTV by IFA. Taken together, the results from this study have important implications in predicting the antigenic cross-reactivity among different anelloviruses based on the ORF1 aa sequence homology. Currently, anelloviruses are classified into nine genera according to the infected host species (human/ape, tamarin, douroucouli, tupaia, pig, dog and cat), nucleotide sequence identity and the genome size of primate anelloviruses (TTV, TTMV and TTMDV) (Biagini, P., M. Bendinelli, S. Hino, L. Kakkola, A. Mankertz, C. Niel, H. Okamoto, S. Raidal, C. G. Teo, and D. Todd. 2011. Anelloviridae, p. 331-341. In A. M. Q. King, M. J. Adams, E. B. Carstens, and E. J. Lefkowitz (ed.), Virus Taxonomy, 9th Report of the ICTV. Elsevier Academic Press, London). The ORF1 of the TTSuV (Genus Iotatorquevirus) share 15.6-22.3% aa sequence identity with the other eight genera based on multiple sequence alignment (data not shown), which is similar to that between TTSuVs and the human genogroup 1 TTV (19.1-21.0%). Therefore, it is reasonable to deduce that porcine anellovirus is not antigenically cross-reactive with other anelloviruses in other animal species. The ORF1 aa sequence homologues among the nine genera range from 15.0% to 27.3% (data not shown), thus implying that antigenic diversity between different genera does exist.

The two TTSuV species (TTSuV1 and TTSuV2) do not share antigenicity in the ORF1 antigen since they only had 22.4-25.8% aa sequence identity, whereas the two TTSuV1 genotypes (TTSuV1a and 1b) were antigenically related and cross-reactive due to their higher aa sequence homology (49.4-52.4%). It is possible that the antigenic relationship of different anelloviruses in the same genus may depend on a threshold or a range of aa sequence homology. The available data using TTSuV as a model will provide insights into similar research of antigenic diversity on human anelloviruses (TTV, TTMV and TTMDV) in the future.

Figure 3:
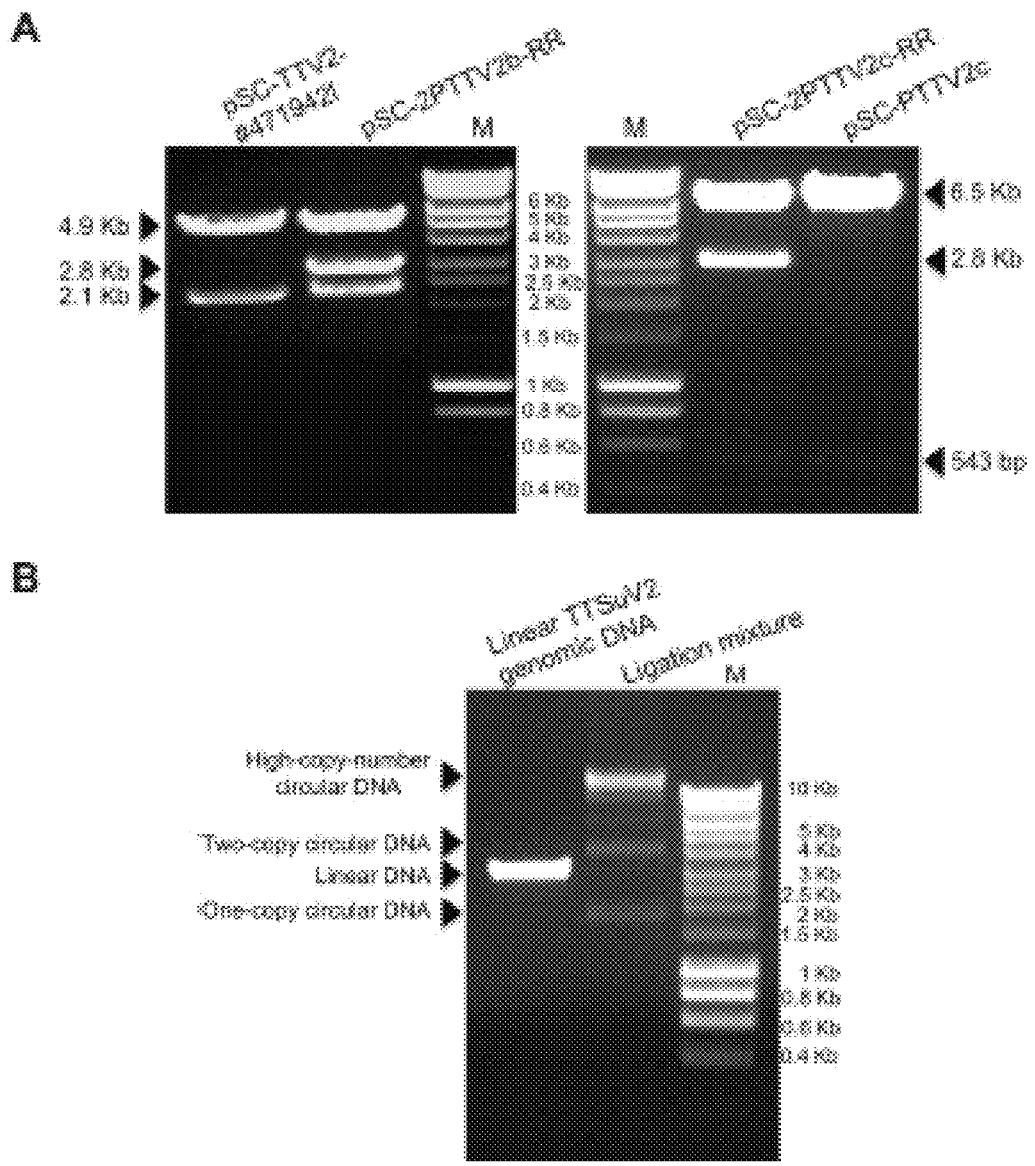
FIG. 3 illustrates identification and quality assessment of linear or circular TTsuV2 genomic DNA. (A) Comparisons of the HindIII single-digestion patterns between clones pSC-TTV2-#471942 and pSC-2PTTV2b-RR (left panel) and AflII single-digestion patterns between clones pSC-PTTV2c and pSC-2PTTV2c-RR (right panel) by agarose gel electrophoresis. M: DNA markers. The results were consistent to the predicted patterns of the digested fragments (shown by black arrowheads). The 2.8-Kb fragments indicate the intact single TTsuV2 genomic DNA from the clone pSC-2PTTV2b-RR or pSC-2PTTV2c-RR. (B) Quality assessment of concatemerized ligation products of the BamHI-digested and purified PTTV2c genomic DNA. The samples were electrophoresed in a 1% agarose gel before (linear DNA) and after (ligation mixture) T4 DNA ligase treatment. Linear DNA (~2.8 Kb) and formations of the putative one-copy (monomer), two-copy (dimer) and high-copy-number circular DNA are indicated by arrowheads.
Figure 11:
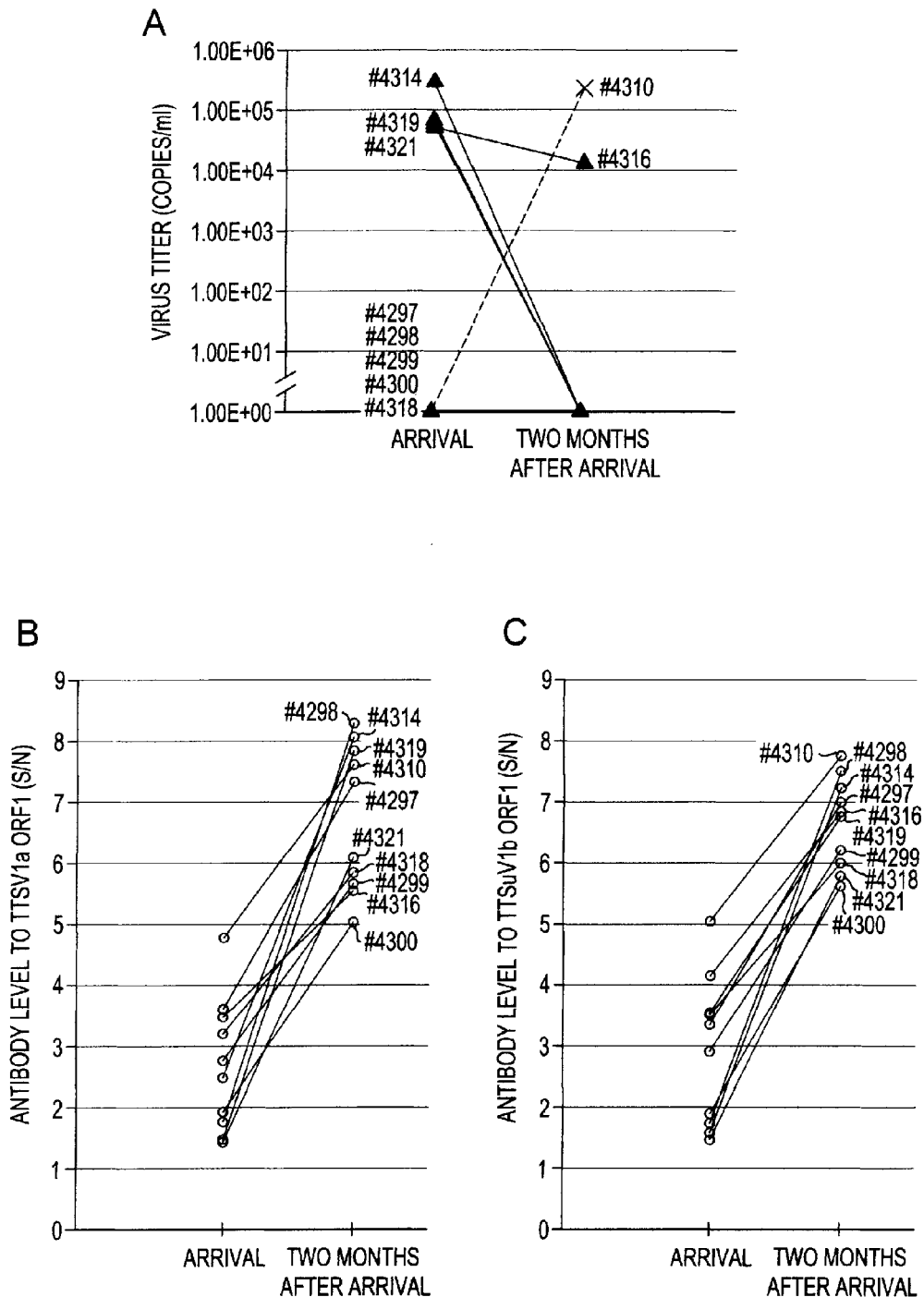
FIG. 11 illustrates a retrospective evaluation of TTSuV1 viral loads (A), antibody levels to the ORF1 protein of TTSuV1a (B) and TTSuV1b (C) in 10 pigs in group A from the time of their arrival at the research facility to two months after arrival.

The present study on TTSuV1 together with our previous study on TTSuV2 (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88) also revealed a broader picture of the nature of mixed TTSuVs infections under natural or clinically disease conditions by assessing the serological and virological profiles. It is not surprising to see in this study that several features of TTSuV1 infection were consistent with that of TTSuV2 (FIG. 3 & FIG. 11). More importantly, the inventors provided new evidence to support the current opinion that TTSuV1 is likely not associated with PCVAD (1, 18, 23), by demonstrating that both viral loads and antibody levels were not significant different between PCVAD-affected and -unaffected pigs (FIG. 12), and that there was no significant PCV2/TTSuV1 synergic effect. It is not known whether the presence of ORF1 antibody is protective against homologous TTSuV infection. However, since antibodies to TTSuV1 or TTSuV2 ORF1 do not cross-react with the heterologous TTSuV antigen, it appears that TTSuV1 infection and the consequent humoral immune response do not interfere with TTSuV2 infection. Therefore, this may make the development of a single vaccine against the two recognized TTSuV species difficult. Together, the results from the present study have important implications in understanding the diversity of anellovirus, and in diagnosis and vaccine development of TTSuVs.

Vaccines of the infectious viral and infectious molecular DNA clones, and methods of using them, are also included within the scope of the present invention. Inoculated pigs are protected from viral infection and associated diseases caused by TTV2 infection or co-infection. The novel method protects pigs in need of protection against viral infection by administering to the pig an immunologically effective amount of a vaccine according to the invention, such as, for example, a vaccine comprising an immunogenic amount of the infectious TTsuV DNA, a plasmid or viral vector containing the infectious DNA clone of TTsuV, the recombinant TTsuV DNA, the polypeptide expression products, the bacteria-expressed or baculovirus-expressed purified recombinant ORF1 capsid protein, etc. Other antigens such as PRRSV, PPV, other infectious swine agents and immune stimulants may be given concurrently to the pig to provide a broad spectrum of protection against viral infections.

The vaccines comprise, for example, the infectious viral and molecular DNA clones, the cloned TTsuV infectious DNA genome in suitable plasmids or vectors such as, for example, the pSC-B vector, an avirulent, live virus, an inactivated virus, expressed recombinant capsid subunit vaccine, etc. in combination with a nontoxic, physiologically acceptable carrier and, optionally, one or more adjuvants. The vaccine may also comprise the infectious TTsuV2 molecular DNA clone described herein. The infectious TTsuV DNA, the plasmid DNA containing the infectious viral genome and the live virus are preferred with the live virus being most preferred. The avirulent, live viral vaccine of the present invention provides an advantage over traditional viral vaccines that use either attenuated, live viruses which run the risk of reverting back to the virulent state or killed cell culture propagated whole virus which may not induce sufficient antibody immune response for protection against the viral disease.

Vaccines and methods of using them are also included within the scope of the present invention. Inoculated mammalian species are protected from serious viral infection, may also provide protection for disease related to co-infection of TTsuV, such as porcine dermatitis and nephropathy syndrome (PDNS), postweaning multisystemic wasting syndrome (PMWS), and other related illness. The vaccines comprise, for example, an inactivated or attenuated TTsuV virus, a nontoxic, physiologically acceptable carrier and, optionally, one or more adjuvants.

The adjuvant, which may be administered in conjunction with the vaccine of the present invention, is a substance that increases the immunological response of the pig to the vaccine. The adjuvant may be administered at the same time and at the same site as the vaccine, or at a different time, for example, as a booster. Adjuvants also may advantageously be administered to the pig in a manner or at a site different from the manner or site in which the vaccine is administered. Suitable adjuvants include, but are not limited to, aluminum hydroxide (alum), immunostimulating complexes (IS-COMS), non-ionic block polymers or copolymers, cytokines (like IL-1, IL-2, IL-7, IFN-α, IFN-β, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

The vaccines may further contain additional antigens to promote the immunological activity of the infectious TTsuV DNA clones such as, for example, porcine reproductive and respiratory syndrome virus (PRRSV), porcine parvovirus (PPV), other infectious swine agents and immune stimulants.

The new vaccines of this invention are not restricted to any particular type or method of preparation. The cloned viral vaccines include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

As a further benefit, the preferred live virus of the present invention provides a genetically stable vaccine that is easier to make, store and deliver than other types of attenuated vaccines.

Another preferred vaccine of the present invention utilizes suitable plasmids for delivering the nonpathogenic DNA clone to pigs. In contrast to the traditional vaccine that uses live or killed cell culture propagated whole virus, this invention provides for the direct inoculation of pigs with the plasmid DNA containing the infectious viral genome.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective response in pigs (e.g., proteins derived from ORF1, ORF1/1, ORF2, ORF2/2, etc.). Such identified genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product. The recombinant subunit vaccines are based on bacteria-expressed (FIG. 10, FIG. 15) or baculovirus-expressed ORF1 capsid proteins of TTsuV1a, PTTsuV1b and TTsuV2.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides (see, for instance, Zoller et al., DNA 3:479-488, 1984). An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

An immunologically effective amount of the vaccines of the present invention is administered to a pig in need of protection against viral infection. The immunologically effective amount or the immunogenic amount that inoculates the pig can be easily determined or readily titrated by routine testing. An effective amount is one in which a sufficient immunological response to the vaccine is attained to protect the pig exposed to the TTsuV virus. Preferably, the pig is protected to an extent in which one to all of the adverse physiological symptoms or effects of the viral disease are significantly reduced, ameliorated or totally prevented.

The vaccine can be administered in a single dose or in repeated doses. Dosages may range, for example, from about 1 microgram to about 1,000 micrograms of the plasmid DNA containing the infectious chimeric DNA genome (dependent upon the concentration of the immuno-active component of the vaccine), preferably 100 to 200 micrograms of the TTsuV DNA clone, but should not contain an amount of virus-based antigen sufficient to result in an adverse reaction or physiological symptoms of viral infection. Methods are known in the art for determining or titrating suitable dosages of active antigenic agent to find minimal effective dosages based on the weight of the pig, concentration of the antigen and other typical factors. Preferably, the infectious viral DNA clone is used as a vaccine, or a live infectious virus can be generated in vitro and then the live virus is used as a vaccine. In that case, from about 50 to about 10,000 of the 50% tissue culture infective dose (TCID 50) of live virus, for example, can be given to a pig.

The new vaccines of this invention are not restricted to any particular type or method of preparation. The vaccines include, but are not limited to, modified live vaccines, inactivated vaccines, subunit vaccines, attenuated vaccines, genetically engineered vaccines, etc.

The advantages of live vaccines are that all possible immune responses are activated in the recipient of the vaccine, including systemic, local, humoral and cell-mediated immune responses. The disadvantages of live virus vaccines, which may outweigh the advantages, lie in the potential for contamination with live adventitious viral agents or the risk that the virus may revert to virulence in the field.

To prepare inactivated virus vaccines, for instance, the virus propagation and virus production can occur in cultured porcine cell lines such as, without limitation PK-15 cells. Serial virus inactivation is then optimized by protocols generally known to those of ordinary skill in the art or, preferably, by the methods described herein.

Inactivated virus vaccines may be prepared by treating the TTsuV with inactivating agents such as formalin or hydrophobic solvents, acids, etc., by irradiation with ultraviolet light or X-rays, by heating, etc. Inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating, agent) temperature or pH to inactivate the virus. Inactivation by heating is conducted at a temperature and for a length of time sufficient to inactivate the virus. Inactivation by irradiation is conducted using a wavelength of light or other energy source for a length of time sufficient to inactivate the virus. The virus is considered inactivated if it is unable to infect a cell susceptible to infection.

The preparation of subunit vaccines typically differs from the preparation of a modified live vaccine or an inactivated vaccine. Prior to preparation of a subunit vaccine, the protective or antigenic components of the vaccine must be identified. In the present invention, antigenic components of TTsuV were identified as the ORF1 capsid proteins of TTsuV1a, TTsuV1b and TTsuV2, which were expressed and purified in *Escherichia coli* (*E. coli*) in this invention, and other expression system, such as baculovirus expression system, for use as subunit recombinant capsid vaccines. Such protective or antigenic components include certain amino acid segments or fragments of the viral capsid proteins which raise a particularly strong protective or immunological response in pigs; single or multiple viral capsid proteins themselves, oligomers thereof, and higher-order associations of the viral capsid proteins which form virus substructures or identifiable parts or units of such substructures; oligoglycosides, glycolipids or glycoproteins present on or near the surface of the virus or in viral substructures such as the lipoproteins or lipid groups associated with the virus, etc. Preferably, the ORF1 protein is employed as the antigenic component of the subunit vaccine. Other proteins may also be used such as those encoded by the nucleotide sequence in the ORF2, ORF1/1, and ORF2/2 gene. These immunogenic components are readily identified by methods known in the art. Once identified, the protective or antigenic portions of the virus (i.e., the "subunit") are subsequently purified and/or cloned by procedures known in the art. The subunit vaccine provides an advantage over other vaccines based on the live virus since the subunit, such as highly purified subunits of the virus, is less toxic than the whole virus.

If the subunit vaccine is produced through recombinant genetic techniques, expression of the cloned subunit such as the ORF1, ORF2, ORF1/1, and ORF2/2 genes, for example, may be expressed by the method provided above, and may also be optimized by methods known to those in the art (see, for example, Maniatis et al "Molecular Cloning: A Laboratory Manual," Cold Spring Harbor Laboratory, Cold Spring Harbor, Mass. (1989)). On the other hand, if the subunit being employed represents an intact structural feature of the virus, such as an entire capsid protein, the procedure for its isolation from the virus must then be optimized. In either case, after optimization of the inactivation protocol, the subunit purification protocol may be optimized prior to manufacture.

To prepare attenuated vaccines, the live, pathogenic virus is first attenuated (rendered nonpathogenic or harmless) by methods known in the art or, preferably, as described herein. For instance, attenuated viruses may be prepared by the technique of the present invention which involves the novel serial passage through embryonated pig eggs. Attenuated viruses can be found in nature and may have naturally-occurring gene deletions or, alternatively, the pathogenic viruses can be attenuated by making gene deletions or producing gene mutations. The attenuated and inactivated virus vaccines comprise the preferred vaccines of the present invention.

Genetically engineered vaccines, which are also desirable in the present invention, are produced by techniques known in the art. Such techniques involve, but are not limited to, the use of RNA, recombinant DNA, recombinant proteins, live viruses and the like.

For instance, after purification, the wild-type virus may be isolated from suitable clinical, biological samples such as serum, fecal, saliva, semen and tissue samples by methods known in the art, preferably by the method taught herein using infected pigs or infected suitable cell lines. The DNA is extracted from the biologically pure virus or infectious agent by methods known in the art, and purified by methods known in the art, preferably by ultracentrifugation in a CsCl gradient. The cDNA of viral genome is cloned into a suitable host by methods known in the art (see Maniatis et al., id.), and the virus genome is then analyzed to determine essential regions of the genome for producing antigenic portions of the virus. Thereafter, the procedure is generally the same as that for the modified live vaccine, an inactivated vaccine or a subunit vaccine.

Genetically engineered vaccines based on recombinant DNA technology are made, for instance, by identifying the portion of the viral gene which encodes for proteins responsible for inducing a stronger immune or protective response in pigs (e.g., proteins derived from ORF1, ORF2, ORF1/1, and ORF2/2, etc.). Such identified genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman Co. (1992)). The host cells are cultured, thus expressing the desired vaccine proteins, which can be purified to the desired extent and formulated into a suitable vaccine product.

Genetically engineered proteins, useful in vaccines, for instance, may be expressed in insect cells, yeast cells or mammalian cells. The genetically engineered proteins, which may be purified or isolated by conventional methods, can be directly inoculated into a porcine or mammalian species to confer protection against TTsuV.

An insect cell line (like sf9, sf21, or HIGH-FIVE) can be transformed with a transfer vector containing polynucleic acids obtained from the virus or copied from the viral genome which encodes one or more of the immuno-dominant proteins of the virus. The transfer vector includes, for example, linearized baculovirus DNA and a plasmid containing the desired polynucleotides. The host cell line may be co-transfected with the linearized baculovirus DNA and a plasmid in order to make a recombinant baculovirus.

Alternatively, DNA from the isolated TTsuV which encode one or more capsid proteins can be inserted into live vectors, such as a poxvirus or an adenovirus and used as a vaccine.

An immunologically effective amount of the vaccine of the present invention is administered to an porcine or mammalian species in need of protection against said infection or syndrome. The "immunologically effective amount" can be easily determined or readily titrated by routine testing. An effective amount is one in which a sufficient immunological response to the vaccine is attained to protect the pig or other mammal exposed to the TTsuV virus, or TTsuV co-infection, which may cause porcine dermatitis and nephropathy syndrome (PDNS), postweaning multisystemic wasting syndrome (PMWS) or related illness. Preferably, the pig or other mammalian species is protected to an extent in which one to all of the adverse physiological symptoms or effects of the viral disease are found to be significantly reduced, ameliorated or totally prevented.

The vaccine can be administered in a single dose or in repeated doses. Dosages may contain, for example, from 1 to 1,000 micrograms of virus-based antigen (dependent upon the concentration of the immuno-active component of the vaccine), but should not contain an amount of virus-based antigen sufficient to result in an adverse reaction or physiological symptoms of viral infection. Methods are known in the art for determining or titrating suitable dosages of active antigenic agent based on the weight of the bird or mammal, concentration of the antigen and other typical factors.

The vaccine can be administered to pigs. Also, the vaccine can be given to humans such as pig farmers who are at high risk of being infected by the viral agent. It is contemplated that a vaccine based on the TTsuV can be designed to provide broad protection against both porcine and human TTV. In other words, the vaccine based on the TTsuV can be preferentially designed to protect against human TTV infection through the so-called "Jennerian approach" (i.e., cowpox virus vaccine can be used against human smallpox by Edward Jenner). Desirably, the vaccine is administered directly to a porcine or other mammalian species not yet exposed to the TTV virus. The vaccine can conveniently be administered orally, intrabuccally, intranasally, transdermally, parenterally, etc. The parenteral route of administration includes, but is not limited to, intramuscular, intravenous, intraperitoneal and subcutaneous routes.

When administered as a liquid, the present vaccine may be prepared in the form of an aqueous solution, a syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions which contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of mammalian body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives which can be employed in the present vaccine include, but are not limited to, dextrose, conventional antioxidants and conventional chelating agents such as ethylenediamine tetraacetic acid (EDTA). Parenteral dosage forms must also be sterilized prior to use.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

EXAMPLES

Example 1

Cell Lines and Cell Cultures

A total of twelve continuous cell lines were used in this study. A type 1 porcine circovirus (PCV1)-free porcine kidney epithelial cell line PK-15 (Fenaux, M., T. Opriessnig, P.

G. Halbur, F. Elvinger, and X. J. Meng. 2004. A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs. J Virol 78:6297-303), a swine testis cell line ST (ATCC CRL-1746, passage 6), a baby hamster kidney fibroblast cell line BHK-21 (ATCC CCL-10, passage 62), and an African green monkey kidney epithelial Vero cell (ATCC CCL-81, passage 95) were each grown in modified Eagle's medium (MEM) supplemented with 10% fetal bovine serum (FBS) and antibiotics. A porcine monocytic cell line 3D4/31 (ATCCCRL-2844, passage 8), a porcine small intestinal epithelial cell line IPEC-J2 (a gift from Dr. Anthony Blikslager at North Carolina State University, Raleigh, N.C.) (Schierack, P., M. Nordhoff, M. Pollmann, K. D. Weyrauch, S. Amasheh, U. Lodemann, J. Jores, B. Tachu, S. Kleta, A. Blikslager, K. Tedin, and L. H. Wieler. 2006. Characterization of a porcine intestinal epithelial cell line for in vitro studies of microbial pathogenesis in swine. Histochem Cell Biol 125:293-305), and a hamster ovary cell line CHO-K1 (ATCC CCL-61, passage 12) were each cultured in Dulbecco's modified Eagle's medium (DMEM) and nutrient mixture F-12 (Ham) (1:1) with GlutaMAX™-I (Invitrogen, Carlsbad, Calif.) supplemented with 5% FBS and antibiotics. A monkey kidney cell line subclone MARC-145 (passage 42) derived from MA-104 (ATCC CRL-2378), a human cervical cancer cell line HeLa (ATCC CCL-2, passage 10), two human hepatocellular carcinoma cell lines Huh-7 (subclone 10-3; a gift from Dr. Suzanne U. Emerson at NIAID, NIH) (Emerson, S. U., H. Nguyen, J. Graff, D. A. Stephany, A. Brockington, and R. H. Purcell. 2004. In vitro replication of hepatitis E virus (HEV) genomes and of an HEV replicon expressing green fluorescent protein. J Virol 78:4838-46) and HepG2 (ATCC CRL-10741, passage 7) were each grown in DMEM supplemented with 10% fetal bovine serum (FBS) and antibiotics. A human 293 cell line, 293TT, engineered to stably express high levels of SV40 large T antigen (a gift from Dr. John T. Schiller, Laboratory of Cellular Oncology, National Cancer Institute, Bethesda, Md.) (Buck, C. B., D. V. Pastrana, D. R. Lowy, and J. T. Schiller. 2004. Efficient intracellular assembly of papillomaviral vectors. J Virol 78:751-7), was cultured in DMEM-10 medium (DMEM with 10% inactivated FBS, 1% nonessential amino acids and 1% GlutaMAX-I) supplemented with 400 µg/ml hygromycin B and antibiotics. All cells were grown at 37° C. with 5% $CO_2$.

Example 2

Analysis of TTSuV1 or TTSuV2 Contamination in Cultured Cells by Real-Time Quantitative PCR (qPCR)

To ensure that the porcine-derived cell lines used in the study were free of TTSuV contamination, five cell lines, PCV1-free PK-15, 3D4/31, IPEC/J2, BHK-21 and MARC-145, were tested for TTSuV1 or TTSuV2 DNA by using two singleplex SYBR green-based real-time qPCR assays (Huang, Y. W., B. A. Dryman, K. K. Harrall, E. M. Vaughn, M. B. Roof, and X. J. Meng. 2010. Development of SYBR green-based real-time PCR and duplex nested PCR assays for quantitation and differential detection of species- or type-specific porcine Torque teno viruses. J Virol Methods 170:140-6). Briefly, total DNA was extracted from each cell line using the QIAamp DNA mini kit (Qiagen) and was subsequently subjected to TTSuV1 or TTSuV2 qPCR detection in a 25-0 PCR system using SensiMix SYBR & Fluorescein kit (Quantace Ltd) as described previously (Huang, Y. W., B. A. Dryman, K. K. Harrall, E. M. Vaughn, M. B. Roof, and X. J. Meng. 2010. Development of SYBR green-based real-time PCR and duplex nested PCR assays for quantitation and differential detection of species- or type-specific porcine Torque teno viruses. J Virol Methods 170:140-6). A TTSuV1 or TTSuV2 standard template and a porcine serum sample from a commercial company used in cell culture, which is supposed to be OIE (The World Organization for Animal Health) diseases-free, were included as controls. All samples were run in duplicate on the same plate.

Example 3

Generation of a Rabbit Anti-TTSuV2 ORF1 Antiserum

The inventors have previously expressed and purified a recombinant truncated ORF1 protein of TTSuV2 (PTTV2c-VA strain) (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). The purified protein products were used to immunize two New Zealand white rabbits as a custom antibody production service at Rockland Immunochemicals (Gilbertsville, Pa.). Serum samples from both rabbits were collected before immunization (pre-bleed) and at 45 days post-immunization.

Example 4

Construction of Full-Length Genomic DNA Clones of TTSuV2

Two PCR fragments (E and F) covering the full-length genome of the U.S. strain of TTSuV2 isolate PTTV2c-VA (GenBank accession no. GU456386; SEQ ID NO:1) were re-amplified from the constructs reported previously (Huang, Y. W., Y. Y. Ni, B. A. Dryman, and X. J. Meng. 2010. Multiple infection of porcine Torque teno virus in a single pig and characterization of the full-length genomic sequences of four U.S. prototype PTTV strains: implication for genotyping of PTTV. Virology 396:287-97), which were subsequently assembled into a full-length genomic DNA by overlapping PCR using the Herculase II Fusion DNA Polymerase (Stratagene) in the vector pSC-B-amp/kan (Stratagene). The monomeric TTSuV2 DNA fragment was flanked by a BamHI restriction site at both ends. The resulting construct was designated pSC-PTTV2c (FIG. 1A). The full-length PTTV2c genome was excised from the clone pSC-PTTV2c using BamHI digestion, purified and ligated head-to-tail to form concatemers. Two-copy concatemers were cloned into the BamHI-pre-digested pSC-B-amp/kan vector to produce a tandem-dimerized TTSuV2 DNA clone, pSC-2PTTV2c-RR (FIG. 1B). Similarly, two plasmids harboring monomeric and tandem-dimerized TTSuV2 genomic DNA originated from German TTSuV2 isolate TTV2 #472142 (GenBank accession no. GU188046; SEQ ID NO:2) (Gallei, A., S. Pesch, W. S. Esking, C. Keller, and V. F. Ohlinger. 2010. Porcine Torque teno virus: determination of viral genomic loads by geno-group-specific multiplex rt-PCR, detection of frequent multiple infections with genogroups 1 or 2, and establishment of viral full-length sequences. Vet Microbiol 143:202-12) were constructed with the EcoRV site on the same vector backbone, respectively. Since the TTV2-#471942 strain was classified into the TTSuV2 subtype 2b together with the U.S. isolate PTTV2b-VA based upon phylogenetic analysis (data not shown), the inventors designated these two clones pSC-TTV2-#471942 (FIG. 1C) and pSC-2PTTV2b-RR (FIG. 1D), respectively.

Example 5

Introduction of Genetic Markers into the Two TTSuV2 Monomeric DNA Clones and Construction of a TTSuV2 Deletion Mutant An HpaI restriction enzyme site was engineered into the putative spliced region (intron) of TTSuV2 genome in the clone pSC-TTV2-#471942 for introducing a genetic marker to discriminate between the cloned virus and the potential indigenous viruses in the subsequent animal study. To create the unique HpaI site (GTTAAC; mutations are underlined; SEQ ID NO:3), three point mutations, C to T, C to A and T to A at nucleotide (nt) positions 1817, 1819 and 1820 corresponding to the TTV2-#471942 genome were generated by a fusion PCR technique using two pairs of primers containing the desired mutations. The fusion PCR product replaced the corresponding region on the clone pSC-TTV2-#471942 by using the cloning site KpnI at both ends. The mutations did not change the putative ORF1 capsid amino acid sequence. The resulting full-length DNA clone was named pSC-TTV2-EU (FIG. 1E). Using the same strategy, two unique restriction sites, PstI (CTGCAG; SEQ ID NO:4) and MfeI (CAATTG; SEQ ID NO:5), were introduced into the putative intron of the PTTV2c-VA genome in the pSC-PTTV2c clone (FIG. 1F). The new clone, designed pSC-TTV2-US, contained three silent mutations at nt positions 1613 (A to T), 1784 (T to C) and 1787 (C to T) corresponding to the PTTV2c-VA genome. A mutant clone pSC-TTV2-ΔAA, with a 104-bp deletion (nt positions 332-437) from the putative TATA box to the ORF1/ORF2 start codon on the clone pSC-TTV2-US, was also generated by removing the short deletion fragment with double-digestion with the AccI and ApaI enzymes followed by formation of two blunt ends with a Klenow enzyme and self-ligation (FIG. 1G). All mutagenesis were confirmed by DNA sequencing.

Example 6

In Vitro Transfection of TTSuV DNA Clones

The PCV1-free PK-15 cells were seeded at $2 \times 10^5$ cells per well onto a 6-well plate and grown until 60%-70% confluency before transfection. Two micrograms of the tandem-dimerized clones pSC-2PTTV2b-RR and pSC-2PTTV2c-RR were directly transfected into the cells, respectively, using Lipofectamine LTX (Invitrogen) according to the manufacturer's protocol. For monomeric clones pSC-PTTV2c, pSC-TTV2-#471942, pSC-TTV2-EU, pSC TTV2-US and pSC-TTV2-AAA, the respective genomic fragment was excised by BamHI or EcoRV enzyme, gel-purified, and re-ligated with the T4 DNA ligase overnight. The ligation mixtures (~2 μg) were used for transfection using Lipofectamine LTX, respectively. Cells were cultured for 3 to 5 days, and then subjected to an immunofluorescence assay (IFA) to detect the expression of ORF1. Alternatively, transfected cells were passaged into new 6-well plates and were cultured for 3 days before detection of ORF1 expression by IFA. Transfection of the other 11 cell lines and IFA detection were similar.

Example 7

Immunofluorescence Assay (IFA)

Transfected or passaged cells on 6-well plates were washed times with PBS and fixed with acetone. Five hundred microliters of the anti-TTSuV2 ORF1 antiserum at a 1:500 dilution in PBS, was added to the cells for each well and incubated for 1 hour at room temperature. Cells were washed 3 times with PBS and 500 μl Texas Red- or Alexa Fluor 488-conjugated goat anti-rabbit IgG (Invitrogen) at a 1:300 dilution was subsequently added. After incubation for 1 hour at room temperature, the cells were washed with PBS, stained with 500 μl DAPI (KPL, Inc.) at a 1:1000 dilution and visualized under a fluorescence microscope.

Example 8

RT-PCR

Total RNA was extracted from PCV1-free PK-15 cells transfected with circular TTSuV2 DNA using the RNeasy mini kit (Qiagen) followed by an RNase-free DNase I treatment. The cDNA synthesis was performed using SuperScript II reverse transcriptase (Invitrogen) with oligo-dT as the reverse primer. PCR was performed in a 50-μL reaction with the Advantage 2 PCR kit (Clontech) using primers TTV2-448F (5'-GAAGAAAGATGGCTGACGGTAGCGTACT-3'; SEQ ID NO:6) and TTV2-2316R (5'-AGGTGCTTGAG-GAGTCGTCGCTTG-3'; SEQ ID NO:7). The PCR products were gel-purified, cloned into a pCR2.1 vector (Invitrogen) by TA cloning strategy and sequenced.

Example 9

In Vivo Transfection of Colostrum Deprived (CD) Pigs with the Tandem-Dimerized TTSuV2 Clones It has been previously demonstrated that the infectivity of infectious DNA clones for viruses with a circular genome can be tested by direct inoculation of dimerized full-length genomic DNA into animals (Fenaux, M., T. Opriessnig, P. G. Halbur, F. Elvinger, and X. J. Meng. 2004. A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs. J Virol 78:6297-303). Therefore, in this study, a pilot animal study was initially conducted to determine the infectivity of the two tandem-dimerized TTSuV2 clones pSC-2TTV2c-RR and pSC-2TTV2b-RR. Briefly, six, 26-day old, CD pigs that were seronegative and viral DNA-negative for TTSuV1 and TTSuV2 were assigned into three groups of two each. Each group of pigs was housed separately and maintained under conditions that met all requirements of the Institutional Animal Care and Use Committee. The pigs in each group were injected by using a combination of intra-lymphoid (superficial inguinal lymph nodes) and intramuscular routes with the plasmid DNA of the full-length TTSuV2 clones. The two pigs (nos. 1 and 2) in group 1 were each given 1 ml of PBS buffer and used as the negative control. The two pigs (nos. 3 and 4) in group 2 were each injected with 200 μg of the pSC-2TTV2c-RR plasmid DNA whereas the remaining two pigs (nos. 5 and 6) in group 3 were each inoculated with 200 μg of the pSC-2TTV2b-RR clone.

Pigs were monitored daily for evidence of TTSuV2 infection for a total of 44 days. All pigs were necropsied at 44 days post-inoculation. Serum samples were collected from all pigs prior to inoculation and weekly thereafter until termination of the study. The samples were tested for the presence of TTSuV DNA and quantified for viral loads by a singleplex TTSuV2-specific real-time qPCR (Huang, Y. W., B. A. Dryman, K. K. Harrall, E. M. Vaughn, M. B. Roof, and X. J. Meng. 2010. Development of SYBR green-based real-time PCR and duplex nested PCR assays for quantitation and differential detection of species- or type-specific porcine Torque teno viruses. J Virol Methods 170:140-6). Samples of tissues including brain, lung, lymph nodes, liver, kidney, thymus, spleen, small intestines, large intestines, heart, tonsil, bone marrow were collected during necropsies and processed for microscopic examination. The tissues were examined in fashion blinded to the treatment status of the pigs and given a subjective score for severity of tissue lesions ranged from 0 (normal) to 3 (severe) (Fenaux, M., T. Opriessnig, P. G. Halbur, F. Elvinger, and X. J. Meng. 2004. A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs. J Virol 78:6297-303; Halbur, P. G., P. S. Paul, M. L. Frey, J. Landgraf, K. Eernisse, X. J. Meng, M. A. Lum, J. J. Andrews, and J. A. Rathje. 1995. Comparison of the pathogenicity of two US porcine reproductive and respiratory syndrome virus isolates with that of the Lelystad virus. Vet Pathol 32:648-60).

Example 10

In Vivo Transfection of Cesarean Derived, Colostrum Deprived (CD/CD) Pigs with the Circularized TTSuV2 Genomic DNA Containing Genetic Markers To further verify the results from the initial pilot pig study, the inventors introduced tractable genetic markers into the full-length DNA clones and conducted another CD/CD pig study. Approximately 600 µg of circular or concatamerized TTSuV2 genomic DNA derived from the clone pSC-TTV2-EU or pSC-TTV2-US was generated by ligation of the linearized TTSuV2 genomic DNA. To determine the infectivity of the full-length DNA clones, the inventors inoculated four, 40-day-old, CD/CD pigs (nos. 129, 135, 139 and 140 in group 1) each with 150 µg of concatamerized "TTV2-EU DNA" by a combination of both the intra-lymph node route and intra-muscular route. Another four CD/CD pigs (nos. 133, 137, 138 and 141) in group 2, which were housed in a separate room, were each similarly inoculated with 150 µg of concatamerized "TTV2-US DNA". The remaining four CD/CD pigs (nos. 127, 132, 136 and 142) in group 3 were each injected with 1.5 ml of PBS buffer and served as negative controls. All pigs were monitored for evidence of TTSuV2 infection for a total of 35 days, at which time they were necropsied. Viremia was tested by a TTSuV2 real-time qPCR (Huang, Y. W., B. A. Dryman, K. K. Harrall, E. M. Vaughn, M. B. Roof, and X. J. Meng. 2010. Development of SYBR green-based real-time PCR and duplex nested PCR assays for quantitation and differential detection of species- or type-specific porcine Torque teno viruses. J Virol Methods 170:140-6). A TTSuV2 genomic region of 620 bp containing the engineered genetic markers in TTV2-EU or TTV2-US was amplified from the sera of inoculated pigs by PCR using primers TTV2-tagF (5'-TGACACAGGA/CGTAGGAAATGCAGT-3'; SEQ ID NO:8) and TTV2-tagR (5'-TGAAGTATTTAGGGT-CATTTGTAGCA-3'; SEQ ID NO:9) from selected serum samples of pigs with viremia. The PCR products were gel-purified and cloned into a pCR2.1 vector by using the TA cloning strategy. The white bacterial clones on the X-gal-containing agar plates were picked up for subsequent DNA extraction and sequencing.

Example 11

Sources of Porcine Sera

Porcine sera used in this study were described previously (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88). Briefly, serum samples for serum Western blot (WB) analysis were collected from 20 conventional adult boars with no clinical symptoms from a Virginia pig farm, seven gnotobiotic pigs from Virginia (nos. 4 to 7, 224, 229 and 230; kindly provided by Drs. Lijuan Yuan and Guohua Li from Virginia Tech) and 12 from Iowa (group D), five cesarean-derived, colostrum-deprived (CD/CD) pigs and approximately 50 conventional piglets from a Wisconsin pig farm. A TTSuV2-seropositive porcine serum, which was manufactured in New Zealand and free of all known OIE (The World Organization for Animal Health) notifiable diseases, was also used in this study.

One hundred and sixty porcine serum samples were used for assessing the virological and serological profiles of TTSuV1a and TTSuV1b infection and were divided into five groups (A to E) as described previously (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88): (i) Twenty group-A samples were from 10 specific-pathogen-free (SPF) pigs (60-80 days old at arrival) free of known pathogens and were collected at arrival in the facility and two months after arrival; (ii) Sixty group-B samples were collected from 105 days old pigs in a farm with an outbreak of porcine circovirus associated disease (PCVAD): 30 were from clinically affected pigs and 30 were clinically unaffected pigs; (iii) Fifty-eight group-C samples were collected from 28 days old pigs with unknown disease status: 28 were clinically affected and 30 were clinically unaffected; (iv) Twelve group-D samples were from 14-42 days old gnotobiotic pigs located in Iowa; (v) Ten group-E sera were from 21-30 days old SPF pigs used for an experimental PCV2 infection study.

Example 12

Construction of the TTSuV1a- and TTSuV1b-ORF1 Expression Plasmids

The C-terminal part of the ORF1 of two TTSuV1 strains, PTTV1a-VA (GenBank accession no. GU456383; SEQ ID NO:10) and PTTV1b-VA (GenBank accession no. GU456384; SEQ ID NO:11) was amplified, respectively, from the available PCR fragments reported previously. The amplicon was expected to encode a truncated PTTV1a-VA ORF1 protein of 319 aa (positions 317-635 corresponding to PTTV1a-VA) or a truncated PTTV1b-VA ORF1 protein of 318 aa (positions 322-639 corresponding to PTTV1b-VA).

An additional methionine was introduced at the N-terminus of each amplified fragments. Two ORF1 expression plasmids, designated pTri-1aORF1 and pTri-1bORF1, were each constructed by cloning the respective PCR product into a bacterial/insect/mammalian-triple expression vector pTriEx1.1-Neo (Novagen) between the NcoI and XhoI restriction sites to generate two C-terminally 8×His-tagged fusion proteins. The recombinant plasmids were confirmed by DNA sequencing. The TTSuV2 ORF1 expression construct, pTri-2cORF1, had been described previously (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88).

Example 13

Expression and Purification of the Recombinant TTSuV1a- and TTSuV1b-ORF1 Proteins The two plasmids were each transformed into Rosetta 2 (DE3) pLacI competent cells (Novagen). The bacteria were grown in 100-ml of Overnight Express TB Media (Novagen) for 16-18 hours at 37° C. and then the bacterial culture was harvested by centrifugation at 3,400 rpm for 15 minutes at 4° C. The resulting bacterial pellet was treated with BugBuster and rLysozyme according to the manufacture's protocol (Novagen). Benzonase Nuclease (Novagen) was added to degrade DNA and RNA. The resulting inclusion bodies were lysed in 6 M guanidine hydrochloride, 0.1 M sodium phosphate, 0.01 M Tris-Chloride, and 0.01 M imidazole with a pH value of 8.0. The lysate supernatants were collected by centrifugation and were used for His-tagged protein purification by a Ni-NTA His●Bind Resin 50% (Novagen) under denaturing condition with 8 M urea. Proteins were dialyzed as described previously (13). The recombinant His-tagged TTSuV1a- or TTSuV1b ORF1 proteins used as the antigen for ELISA and rabbit immunization were quantified using a NanoDrop spectrophotometry and frozen at −80° C. until use.

Example 14

Generation of Anti-ORF1 Antisera of TTSuV1a and TTSuV1b in Rabbits

The two ORF1 proteins of TTSuV1a and TTSuV1b expressed in *E. coli* were purified and used to immunize two New Zealand white rabbits, respectively, at a custom antibody production service at Rockland Immunochemicals (Gilbertsville, Pa.). Antisera were harvested at 50 days post-immunization.

Example 15

SDS-PAGE, Anti-His-Tagged WB and Serum WB Analysis

The unpurified or purified recombinant TTSuV1 ORF1 proteins were resolved on a 4-12% Bis-Tris Polyacrylamide Gel (Invitrogen) by electrophoresis and were subsequently transferred onto a polyvinylidene difluoride (PVDF) membrane. Proteins were detected on the PVDF membrane using an anti-6×His-tagged Mab at a 1:1000 dilution at 4° C., followed by incubation with an IRDye 800CW conjugated goat anti-rabbit IgG (LI-COR Biosciences) at a 1:10,000 dilution at room temperature. After three washing steps using Tris buffered saline/0.05% Tween 20 (TBS-T; Sigma), the membrane was analyzed using the Odyssey Infrared Imaging System (LI-COR Biosciences).

For serum WB analysis, the purified TTSuV1a- or TTSuV1b-ORF1 proteins were incubated with individual porcine sera at a 1:200 dilution and with IRDye 800CW conjugated rabbit F(ab')$_2$ anti-swine IgG (Rockland Immunochemicals, Inc.) at a 1:10,000 dilution at room temperature. The membrane was then analyzed using the Odyssey Infrared Imaging System.

Example 16

Indirect ELISAs

TTSuV1a- and TTSuV1b-based ELISAs were developed. The optimal concentration of the antigens and the optimal dilutions of sera and HRP conjugates were determined by checkerboard titrations. Similar to the TTSuV2-based ELISA reported previously, the optimal amount of the ORF1 antigen of TTSuV1a or TTSuV1b was 68 ng per well. The optimal ELISA results were obtained by using a 1:100 dilution of serum samples and a 1:4000 dilution of IgG conjugates.

The ELISA was initiated by diluting the purified ORF1 proteins in carbonate coating buffer (pH=9.6) that was used for coating 96-well ELISA plates (Greiner Bio-One) with 100 µl/well. After incubation at 37° C. for 2 hours, each well was washed 3 times with 300 µl of Tris-buffered saline-Tween 20 solution (TBS-T) and blocked with protein-free blocking buffer (Pierce) at a volume of 300 µl for 1 hour at 37° C. One hundred µl of each diluted serum sample was transferred to the corresponding well on the ELISA plates and incubated at 37° C. for 2 hours. After washing the wells three times with 300 µl of TBS-T buffer, the diluted HRP-conjugated rabbit anti-swine IgG (Rockland) was added to each well in a volume of 100 µl and the plate was incubated at 37° C. for 1 hour. A volume of 100 µl of Sure Blue Reserve 1-Component (KPL) was added to each well and incubated for 10 minutes at room temperature. The reaction was stopped by adding 100 µl/well of 1 N HCL. The plates were then read at 450 nm using a spectrophotometer. All serum samples were run in duplicates. Positive and negative controls run in quadruplicates were included on each plate. In general, the mean OD value of the negative control was less than 0.5 whereas the mean OD value of the positive control was greater than 1.5. The ELISA value was calculated as the S/N value that was expressed as a ratio of the mean OD value of a sample to the mean OD value of the negative control (n=4). A subjective cut-off S/N value of 1.2 was used to distinguish between positive and negative samples.

Example 17

Real-Time qPCR Assay for Quantitation of TTSuV1

A SYBR green-based TTSuV1-specific real-time quantitative PCR (qPCR) developed recently in our laboratory was used to measure the total TTSuV1 viral loads (both TTSuV1a and TTSuV1b) in the five groups of pig sera as described previously (12). The minimal detection limit was $1.0 \times 10^4$ copies per ml in this study. The TTSuV1 qPCR assay does not cross-amplify TTSuV2 DNA (Huang, Y. W., B. A. Dryman, K. K. Harrall, E. M. Vaughn, M. B. Roof, and X. J. Meng. 2010. Development of SYBR green-based real-time PCR and duplex nested PCR assays for quantitation and differential detection of species- or type-specific porcine Torque teno viruses. J Virol Methods 170:140-6). Quantitation of TTSuV2 and PCV2 viral loads in group-B sera had been reported previously (Huang, Y. W., K. K. Harrall, B. A. Dryman, N. M. Beach, S. P. Kenney, T. Opriessnig, E. M. Vaughn, M. B. Roof, and X. J. Meng. 2011. Expression of the putative ORF1 capsid protein of Torque teno sus virus 2 (TTSuV2) and development of Western blot and ELISA serodiagnostic assays: correlation between TTSuV2 viral load and IgG antibody level in pigs. Virus Res 158:79-88).

Example 18

Statistical Analyses

Data were analyzed using SAS software (version 9.2; SAS Institute Inc., Cary, N.C.) and GraphPad Prism software (version 5.0; San Diego, Calif.), respectively. Antibody levels (represented by S/N values) were compared between categories of $\log_{10}$ viral titers using the Kruskal-Wallis test followed by Dunn's procedure. For each group that contained clinically affected and non-affected pigs (groups B and C), $\log_{10}$ virus titers were compared between pigs with and without clinical signs using a Wilcoxon 2-sample test. Antibody levels were compared between pigs with and without disease using a 2-sample t-test. Using a cutoff point of 1.2, the proportion of pigs with antibodies was compared between affected and unaffected pigs using a Fisher's exact test.

Correlations between S/N values for TTSuV1a and S/N values for TTSuV1b, and between S/N values for TTSuV1a or TTSuV1b (separately) and TTSuV2 were assessed using Spearman's correlation coefficient. The correlations were separately generated for a combination of 3 groups (group-A to group-C).

To assess the synergistic effects between PCV2 and TTSuV1 on disease prevalence, the pigs in group B were categorized as follows: pigs positive for both PCV2 and TTSuV1, pigs only positive for PCV2, pigs only positive for TTSuV1, and pigs with neither PCV2 nor TTV1. Subsequently, the proportions of affected pigs were compared between the groups using Fisher's exact test. Statistical significance was set to alpha=0.05.

Example 19

Transfection of PK-15 Cell with TTSuV Expression Constructs

PK-15 cells were seeded onto a 6-well plate and grown until 70%-80% confluency before transfection. Two micrograms of each of the three constructs pTri-1aORF1, pTri-1bORF1 and pTri-2cORF1, mixed with 10 µl of Lipofectamine LTX (Invitrogen), were transfected into the cells, respectively. Cells were cultured for 3 days and were subjected to IFA to detect the ORF1 expression.

Example 20

Immunofluorescence Assay (IFA)

Five rabbit antisera were used for IFA staining, including anti-TTSuV1a, anti-TTSuV1b, anti-TTSuV2, pre-bleed rabbit negative control serum, and rabbit anti-human genogroup-1 TTV ORF1 antiserum (AK47; a generous gift from Dr. Annette Mankertz at the Robert Koch-Institute, Berlin, Germany) (21). Transfected cells were fixed with acetone. Five hundred microliters of each of the five antisera, at a 1:500 dilution in PBS, was added on top of the cells in each well and incubated for 1 hour at room temperature. After three washing steps with PBS, the cells were incubated with 500 µl Alexa Fluor 488-labeled goat anti-rabbit IgG (Invitrogen) at a 1:200 dilution for 1 hour incubation at room temperature. Cells were stained with 500 µl DAPI (KPL, Inc.) at a 1:1000 dilution and visualized under a fluorescence microscope.

TABLE 1

Reactivity of anti-TTSuV1a, anti-TTSuV1b, anti-TTSuV2, pre-bleed rabbit and anti human TTV (AK47) sera in PCV1-free PK-15 cells transfected with plasmids encoding truncated ORF1s from TTSuV1a, TTSuV1b and TTSuV2, respectively, as determined by IFA. The intensity of the fluorescent signal was determined visually and expressed ranging from − to ++.

| | Ab | | | | |
|---|---|---|---|---|---|
| Transfection | Anti-TTSuV1a | Anti-TTSuV1b | Anti-TTSuV2 | Pre-bleed rabbit serum | Anti-human TTV (AK47) |
| pTri-1aORF1 | ++ | + | − | − | − |
| pTri-1bORF1 | + | ++ | − | − | − |
| pTri-2cORF1 | − | − | ++ | − | − |
| Mock | − | − | − | − | − |

What is claimed is:

1. An infectious nucleic acid molecule comprising at least two concatemeric or tandem copies of a full-length genome of TTsuV2.

2. The infectious nucleic acid molecule of claim 1, wherein the full-length genome of TTsuV2 is set forth in SEQ ID NO:1.

3. The infectious nucleic acid molecule of claim 1, wherein the genomic sequence is selected from sequences set forth in SEQ ID NO:2.

4. The infectious nucleic acid molecule of claim 2, wherein the full-length genome of TTsuV2 comprising at least one genetic marker in intron 1.

5. The infectious nucleic acid molecule of claim 4, wherein the genetic marker in intron 1 is an artificially introduced restriction site.

6. A biologically functional plasmid or viral vector containing the infectious nucleic acid molecule according to claim 1.

7. The biologically functional plasmid or viral vector of claim 6, containing more than one copy of the infectious nucleic acid molecule.

8. The biologically functional plasmid or viral vector of claim 6, wherein the full-length genome of TTsuV2 is selected from SEQ ID NO:1 or SEQ ID NO:2.

9. An isolated host cell transfected by a vector comprising the infectious nucleic acid molecule according to claim 1.

10. An infectious TTsuV produced by isolated cells containing the infectious nucleic acid molecule according to claim 5.

* * * * *

SEQUENCE LISTING

<160> NUMBER OF SEQ ID NOS: 13

<210> SEQ ID NO 1
<211> LENGTH: 2803
<212> TYPE: DNA
<213> ORGANISM: Torque teno sus virus

<400> SEQUENCE: 1

```
tcatgacagg gttcaccgga agggctgcaa aattacagct aaaaccacaa gtctaacaca      60
ataaaccaca aagtattaca ggaaactgca ataaatttag aaatagatta cacataacca     120
ccaaaccaca ggaaacctac acataaccac caaaccacag gaaacataac caccaaacca     180
caggaaactg tgcaaaaaag gggaaataaa ttctattggc tgggcctgaa gtcctcatta     240
gaataataaa agaaccaatc agaagaactt cctcttttag agtatataag taagtgcgca     300
```

```
gacgaatggc tgagtttatg ccgctggtgg tagacacgaa cagagctgag tgtctaaccg    360
cctgggcggg tgccggagct cctgagagcg gagtcaaggg gcttatcggg caggcggtaa    420
tccagcggaa ccgggccccc ctcgatggaa gaaagatggc tgacggtagc gtactgcgcc    480
cacggattat tctgcggatg taaagacccg aaaaaacacc ttgaaaaatg ccttacagac    540
gctatcgcag acgccgaagg agaccgacac ggagatggag gcaccggagg tggagacgct    600
tctttcgata tcggtatcga cgcgctcctc gccgccgccg cacaaaggta aggagacgga    660
ggagaaaagc tccggtcata caatggttcc ctcctagccg gaggacctgc ctcatagagg    720
gcttctggcc gttgagctac ggacactggt tccgtacctg tctccctatg agaaggctga    780
acggactcat tttcacgggt ggcggttgtg actggacaca gtggagttta caaaacttat    840
accatgaaaa acttaactgg agaaatatat ggacagcttc taatgttggc atggaatttg    900
ctagattttt aagaggaaaa ttttacttct tcagacaccc ctggagaagc tatattatta    960
cttgggacca agacattcct tgcaaacctt taccatacca aaacttacat ccactactta   1020
tgctattaaa aaacaacat aaacttgtac tatctcaaaa agactgtaat ccaaacagaa    1080
gacaaaaacc agtaacttta aaaataagac ctccaccaaa attaacatca cagtggagat   1140
taagcagaga actagcaaaa atgccacttg tcagactagg agtcagtcta atagacctct   1200
cagaaccatg gttagaaggc tggggaaatg cttttttacag cgtactggga tatgaagcta   1260
gtaaacactc agggagatgg tcaaactgga cacaaataaa atacttctgg atatatgaca   1320
caggagtagg aaatgcagtt tatgtcattt tattaaaaca agaggtggat gataatccag   1380
gggcaatggc aacaaaattt gtaactggac caggacaaca cccagatgcc atagacagga   1440
tcgaacaaat aaatgaagga tggccttact ggcttttctt ttacggacag tcagaacaag   1500
acataaaaaa attagcacac gatcaagaaa tagcaaggga atatgcaaac aatccaaaat   1560
ctaaaaaatt aaaaatagga gtgataggat gggctagcag taactttaca acagcaggca   1620
gctcacaaaa tcaaacacca caaacaccag aagccataca aggaggatac gtagcatatg   1680
caggctcaaa aatacaagga gcaggagcaa ttacaaactt atacacagat gcatggccgg   1740
gagaccaaaa ttggccacct ctaaatagag aacaaacaaa ctttaactgg ggcttaagag   1800
gactctgtat aatgagagat aatatgaaac tgggagctca agaactagat gatgaatgta   1860
caatgctcac acttttttgga cctttttgtgg aaaaagcaaa cacagctttt gctacaaatg   1920
accctaaata cttcagacca gaactcaaag actataacat agtaatgaaa tatgccttta   1980
aatttcagtg gggaggccac ggaaccgaaa gattcaaaac aaccatcgga gatcccagca   2040
ccataccatg tccctttgaa cccggggaac ggtaccacca cggggtacaa gaccccgcca   2100
aggtacaaaa cacagtcctc aacccttggg actatgactg tgacgggatt gttagaacag   2160
atactctcaa aagacttctc gaactcccca cagagacgga ggagacggag aaggcgtacc   2220
cactccttgg acaaaaaaca gagaaagagc cattatcaga ctccgacgaa gagagcgtta   2280
tctcaagcac gagcagtgga tcctctcaag aagaagagc gcagagaaga agacagcaca   2340
agccaagcaa gcgacgactc ctcaagcacc tccagcgggt ggtaaagaga atgaagacac   2400
tgtgatagat aaatatagaa acctagcaga ccctcactc aatgtcacag gacacatgga    2460
aaaattcatg caactgcaca tacaaaacgt acaagaaata agagctaaaa atgctaaaaa   2520
atccctcaat aaactttact tttctgatta ataccggcct cctgtgtcca atctattttt    2580
cctacacccc ttcaaaatgg cgggcggac acaaatggc ggaggaaact aagggggggg    2640
caagcccccc ccgggggtt gaggggggt ttccccccct cccccggtg caggggcgg     2700
```

```
agccccccgca cccccccctgc gggggctccg cccccctgcac ccccgggagg gggggaaacc    2760 cccccctcaac cccccgcggg gggcaagccc ccctgcaccc ccc                        2803

<210> SEQ ID NO 2
<211> LENGTH: 2802
<212> TYPE: DNA
<213> ORGANISM: Torque teno sus virus

<400> SEQUENCE: 2
tcatgacagg gttcaccgga agggctgcaa aattacagct aaaaccacaa gtctaacaca         60
ataaaccaca aagtattaca ggaaactgca ataaatttag aaataaatta cacataacca        120
ccaaaccaca ggaaactgtg caaaaaagag gaaataaatt ctattggctc ggtctaaagt        180
cctcattaga ataataaaag aaccaatcag aagaacttcc tcttttagag tatataagta        240
agtgcgcaga cgaatggctg agtttatgcc gctggtggta gacacgaaca gagctgagtg        300
tctaaccgcc tgggcgggtg ccggagctcc agagagcgga gtcaagggc ctatcgggca         360 ggcggtaatc cagcggaacc gggcccccac cctccatgga agaaagatgg ctgacggtag        420
cgtactgcgc ccacggatta ttctgcggct gtaaaaaccc aaaaaaacat ctagaaaaat        480
gccttacaga cgctatcgca gacgccggag gagacccacc agaagatgga ggcaccggag        540
gtggagacgc tactttcgat atcggtatcg acgcgctcct cgccgccgcc gcgcaaaggt        600
aaggagacgg aggaggaaag ctccggtcat acaatggaac cctcctagcc ggaggacctg        660
cctcatagag ggcttctggc cgttgagcta cggacactgg ttccgtacct gtctccctat        720
gagaaggcta acggactta tattcacggg tggcggttgt gactggactc aatggagttt         780
acaaaacttg ttccatgaaa aacttaactg gaggaatata tggacagctt ctaacgtagg        840
catggaattt gctagatttt taagaggaaa attctacttc ttcagacatc cctggagaag        900
ctacatagta acatgggatc aggacattcc ttgtaaacct ctcccatatc aaaacttgca        960
acctctatta atgctactca aaaaacagca taaattagta ctctcacaaa aagactgtaa       1020
cccgagcaga aaacagaaac cggtcacatt aaaattcaga cctccaccaa aattaacatc       1080
acaatggaga ctaagtagag aactctctaa atacctctg attagactag gaataagcct        1140
tatagacctc tcagaaccat ggctagaagg gtggggaaat gcattttaca gtgtcctcgg       1200
atatgaagct tctaaacact ccgggagatg gtcaaactgg acacaaatga aatatttttg       1260
gatatatgac acaggcgtag gaaatgcagt ctacgttatt ttactaaaaa aagatgtaga       1320
tgacaatccc ggagatatgg ctacaaaatt tgtaacagga caagggcaac acccagacgc       1380
tatagatcat atagaaatgg tcaatgaagg gtggccttac tggctattt tttatggaca        1440 atcagaacaa gacattaaaa aactagcaca cgaccaagac atagctagag aatatgccag       1500
agacccaaaa tccaaaaaac taaaaatagg agtcataggg tgggcgagta gcaactatac       1560
aacagcaggc agtaatcaaa acaccacagc acaaacacca gaagcaatac agggaggata       1620
tgtggcctat gcaggttcaa gaataccagg cgcaggatca atcaccaatt tatttcaaat       1680
gggatggcca ggagatcaaa actggccccc cacaaaccaa gaacaaacca attttaactg       1740
gggactcaga ggactctgcg tactcagaga taatatgaaa ttaggagcac aagaactaga       1800
cgatgaatgt acaatgctct cacttttttgg gccttttgtt gaaaaagcaa acacagcctt       1860
tgctacaaat gaccctaaat acttcagacc agaactcaaa gactataatg tagtaatgaa       1920
atatgccttt aaatttcagt ggggaggcca cggaaccgaa agattcaaaa caaccattgg       1980
```

```
agatcccagc accataccat gtcccttcga acccggggaa cggtaccacc acggggtaca    2040 agacccccgcc aagtacaaa acacagtgct caacccttgg gactatgact gtgacgggat    2100
tgttagaaca gatactctca aaagacttct cgaactcccc acagagacgg aggagacgga    2160
gaaggcgtac ccactccttg gacaaaaaac agagaaagag ccattatcag actccgacga    2220
agagagcgtt atctcaagca cgagcagtgg atcgtctcaa gaagaagaga cgcagagaag    2280
aagacagcac aagccaagca agcgacgact cctcaagcac ctccagcggg tggtaaagag    2340
aatgaaaaca ctgtaataga taaatataga aacctagcag acccctcact caatgtcact    2400
ggacacatgg aaaaattcat gcagctacac atacaaaacg tacaagaaat aagagctaaa    2460
aatgctaaaa aatccctcaa taaactttac ttttctgatt aatagcggcc tcctgtgtcc    2520
aatctatttt tcctacaccc attcaaaatg gcgggcggga cacaaatgg cggagggact    2580 aaggggggg caagcccccc ccaccccca tgcggggct ccgcccctg cacccttg    2640 ctaagtcaca aaatggcggc gcggctagga cacaaatgg cggcgtagcg ggggggggga    2700
cccccccgca ccccctgc ggggctccgc ccctgcacc ccggggggg ggggaaaccc    2760 cccctcaacc ccccgcgggg ggcaagcccc cctgcaccccc cc                     2802

<210> SEQ ID NO 3
<211> LENGTH: 10
<212> TYPE: DNA
<213> ORGANISM: Artificial Sequence
<220> FEATURE:
<223> OTHER INFORMATION: sythetically synthesized sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 3 nngttaacnn                                                             10

<210> SEQ ID NO 4
<211> LENGTH: 10
<212> TYPE: DNA
<213> ORGANISM: Artificial Sequence
<220> FEATURE:
<223> OTHER INFORMATION: synthetically synthesized sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 4 nnctgcagnn                                                             10

<210> SEQ ID NO 5
<211> LENGTH: 10
<212> TYPE: DNA
<213> ORGANISM: Artificial Sequence
<220> FEATURE:
<223> OTHER INFORMATION: synthetically synthesized sequence
<220> FEATURE:
<221> NAME/KEY: misc_feature
<222> LOCATION: (1)..(2)
<223> OTHER INFORMATION: n is a, c, g, or t
```

```
<220> FEATURE:
<221> NAME/KEY: misc_feature
<222> LOCATION: (9)..(10)
<223> OTHER INFORMATION: n is a, c, g, or t

<400> SEQUENCE: 5 nncaattgnn                                                                   10

<210> SEQ ID NO 6
<211> LENGTH: 28
<212> TYPE: DNA
<213> ORGANISM: Torque teno sus virus

<400> SEQUENCE: 6
gaagaaagat ggctgacggt agcgtact                                               28

<210> SEQ ID NO 7
<211> LENGTH: 24
<212> TYPE: DNA
<213> ORGANISM: Torque teno sus virus

<400> SEQUENCE: 7
aggtgcttga ggagtcgtcg cttg                                                   24

<210> SEQ ID NO 8
<211> LENGTH: 25
<212> TYPE: DNA
<213> ORGANISM: Torque teno sus virus

<400> SEQUENCE: 8
tgacacagga cgtaggaaat gcagt                                                  25

<210> SEQ ID NO 9
<211> LENGTH: 26
<212> TYPE: DNA
<213> ORGANISM: Torque teno sus virus

<400> SEQUENCE: 9
tgaagtattt agggtcattt gtagca                                                 26

<210> SEQ ID NO 10
<211> LENGTH: 2878
<212> TYPE: DNA
<213> ORGANISM: Torque teno sus virus

<400> SEQUENCE: 10
tacacttccg ggttcaggag gctcaatttg gctagcttcg ctcgcaccac gtttgctgcc            60
aggcggacct gattgaagac tgaaaaccgt taaattcaaa tttgaaaatg gcgggcaaaa           120
tggcggaagg ggggcggagt ttatgcaaat taatttatgc aaagtaggag gagctcgatt           180
ttaatttatg caaagtagga ggagtcaatt ctgattggtc gggagctcaa gtcctcatttt          240 gcatagggtg taaccaatca gatttaaggc gttccccccaa aagtgaatat aagtaagcgc          300
agttccgaat ggctgagttt atgccgccag cggtagacag aactgtctag cgactgggcg           360
ggtgccggag gatccctgat ccggagtcaa ggggcctatc gggcaggagc agctgagcgg           420
agggcctaca tgaaggagaa agactactgg gaggaagcct ggctgaccag ctgtacatct           480
atacacgacc accactgcaa ctgcggtagc tggagagacc acctgtggac gctatgcgct           540
ttagacgacg cagatttggc cgccgccgca gatattatag aaagagaaga ggcggatgga           600
ggagaagatt tcggattcgt agacggagac cctggagacg ctggcgggta aggagatggc           660
```

```
ggcgttccgt cttccgtaga gggggacgta gagcgcgccc ctaccgcatt agcgcttgga      720
accctaaggt tctcagaaac tgccgcatca cgggatggtg gccagttata cagtgtatgg      780
acgggatgga gtggataaaa tacaagccta tggacttaag agtcgaggca aactggatat      840
tcaataaaca ggacagtaaa atagagacag aacagatggg atacctgatg cagtatggag      900
gagggtggtc aagcggagta atcagcttag agggactatt caatgaaaac agactgtgga      960
gaaatatatg gtcaaaaagc aatgacggga tggacttggt cagatacttt ggctgtagaa     1020
ttagactata tccaacagag aatcaggact acttgttctg gtatgacaca gaatttgacg     1080
aacagcaaag gagaatgcta gatgaataca cacaacctag tgtgatgctg caggctaaaa     1140
actcgcgtct aatagtgtgt aaacagaaga tgccaattag acgcagagta aaaagtattt     1200
ttataccgcc gcctgcacag ttaacaactc agtggaaatt tcaacaggaa ctatgtcagt     1260
ttccactgtt taactgggcc tgtatctgca tagacatgga cacgccgttc gactacaacg     1320
gcgcatggcg aaatgcctgg tggctaatga gaaggctgca aaacgaaaac atggagtaca     1380
tagaaagatg gggcagaata ccaatgacag agacacagaa actaccacca gcagacgact     1440
tcaaggcagg aggggtgaac aaaaacttca aaccgacagg tattcaaaga atatacccga     1500
tagtagcggt atgccttgta aagggaacaa aagagtagt caaatgggcc acagtacaca     1560
atggtcccat agacagatgg agaaaaaaac agacaggaac tttaaagctc tctaacctga     1620
gaggcctagt actgagagta tgctcagaga gtgaaacata ctataagtgg acaggatcag     1680
aatttacagg ggcatttcaa caagactggt ggccagtagg cggaacagaa tacccgcttt     1740
gtaccattaa aatggaccca gaatatgaaa accctacagt agaggtatgg tcctggaaag     1800
caaatatacc gacatcaggg actcttaaag actacttcgg actgagtaca gggcaacagt     1860
ggaaagacac tgactttgcg aggctgcaac tacctagaag cagccacaat gtggactttg     1920
gacataaagc tagatttggg ccatttttgcg ttaaaaagcc tccagtagag ttcagagata     1980
cagccccaaa cccactaaat atatgggtaa aatacacgtt ctattttcag ttcggcggca     2040
tgtaccagcc tcccaccgga atccaagatc cctgcacttc taacccgacc tatcctgtca     2100
gaatggtcgg agcagttaca caccccaaat acgccgggca aggcggaatc acgacccaaa     2160
ttggagatca aggtatcacc gctgcctcta tccgtgccat cagtgcagct ccaccagata     2220
cctacacgca gtcggcgttc ctcaaagccc cggaaaccga aaagaagag aaagagaga     2280 gtgagaccag tttcacgagt gccgaaagct cttctgaggg agatggatcg tctgatgacc     2340
aagcagagag acgcgctgcc agaaagcgag tcatcaagtt acttctcaag cgactcgctg     2400
acagacccgt ggacaacaag cgacgacgat tttcagagtg accctgaccc cctcaccaat     2460
aaacgcaaaa aacgcttgca attctaactc tgtctctgtg acttcattgg ggggtccgg     2520 ggggcttgc ccccccgtta gttgggttct cgcactcccg cctgccaagt gaaactcggg     2580
gaggagtgag tgcgggacat cccgtgtaat ggctacataa ctaccggct ttgcttcgac     2640 agtggccgtg gctcgaccct cacacaacac tgcagatagg gggcgcaatt gggatcgtta     2700
gaaaactatg gccgagcatg gggggggctc cgcccccccc aacccccccg gtgggggggc     2760
caaggccccc cctacacccc cccatggggg gctgccgccc cccaaacccc ccgcgtcgga     2820
tggggggggc tgcgcccccc ccaaaccccc cttgcccggg gctgtgcccc ggaccccc      2878
```

<210> SEQ ID NO 11
<211> LENGTH: 2875
<212> TYPE: DNA
<213> ORGANISM: Torque teno sus virus

<400> SEQUENCE: 11

```
tacacttccg ggttcaggag gctcaatttg gctcgcttcg ctcgcaccac gtttgctgcc      60
aagcggacct gattgaagac tgacaaccgt tacattcaaa tttgaaaatg gcgcccaaac     120
atggcggcgg ggggcggagt ttatgcaaat taatttatgc aaagtaggag gagctccatt     180
ttaatttatg caaagtagga ggagtcaatt ctgattggtc gggagctcaa gtcctcattt     240
gcatagggtg taaccaatca gatttaaggc gttcccatta aagcgaatat aagtaagtga     300
ggttccgaat ggctgagttt atgccgccag cggtagacag aactgtctag cgactgggcg     360
ggtgccggag gatccctgat ccggagtcaa ggggcctatc gggcaggagc agctgagcgg     420
agggcctatg ccggaacact gggaggaagc ctggttggaa gctaccaagg gctggcacga     480
tctcgactgc cgctgcggta actggcagga ccacctatgg ctcctactcg ccgatggaga     540
cgccgctttg gccgccgccg tagacgctat agaaagagac gctatgggtg gagaagacgt     600
tactaccgct acagaccgcg ttactatagg agacgatggc tggtaaggag aaggcggcgt     660
tccgtctacc gtagaggtgg acgtagagcg cgcccctacc gaataagtgc ttttaaccca     720
aaagtaatgc ggagggtggt gattagaggt tggtggccaa tattacagtg tctaaaagga     780
caggaatcac taagatatag accactgcag tgggacactg aaaaacagtg gagagtaaag     840
aaagactatg aggacaacta cggctacttg gtgcagtacg gaggaggttg ggggagtggt     900
gaagtgacat tggagggatt atatcaggaa cacttactct ggagaaactc ttggtcaaag     960
ggaaatgatg gcatggacct agtgagatac tttggctgca tagtatacct gtacccactg    1020
caggaccaag actactggtt tggtgggat acagacttta agaactata cgcagagagc    1080
atcaaagaat actcccagcc aagtgttatg atgatggcca acgcactag actagtaata    1140
gctagagaca gagcaccaca cagaagaaga gtaagaaaaa ttttcatacc cccgccaagc    1200
agagacacca cacaatggca atttcagaca gacttctgca aaaggccact attcacatgg    1260
gcggcaggat taatagacat gcagaaacca tttgatgcaa acggagcgtt tagaaacgcc    1320
tggtggctag aaacaaggaa tgaccaggga gaaatgaaat acattgaact atggggaagg    1380
gtgccaccac agggtgacac agaactgcca aaacagagtg agtttaagaa gggagataat    1440
aaccctaact ataacataac ggaaggacat gaaaaaaata tttacccaat aatcatatac    1500
gttgaccaga aagaccagaa aacaagaaaa aaatactgtg tatgctacaa caaaacttta    1560
aatagatgga gaaaagccca ggcgagtaca ttagcaatag gagatcttca aggactagta    1620
ctgcgtcagc ttatgaatca ggagatgaca tactactgga atcgggaga gttttcctca    1680
ccattcctgc aaagatggaa aggaactagg ctaataacca tagacgcaag aaaggcagac    1740
acagaaaacc caaagtaag ttcgtgggaa tgggggcaaa actggaacac aagcggaaca    1800
gtgctacagg aggtattcaa catttcactg aacaacactc aaataagaca ggatgacttt    1860
gcaaaattga cactgccaaa gtcaccacat gacatagact ttggacatca cagcagattt    1920
ggaccattct gtgttaaaaa cgaaccacta gaattccaac tactgcctcc aacaccaact    1980
aacctatggt ttcagtacaa atttctcttt cagtttggcg gtgaatacca gccaccaaca    2040
ggtatccgcg atccctgcat tgatacacca gcctatcctg tgccgcagtc aggaagtgtt    2100
acacacccca aattcgccgg aaagggcgga atgctcacgg aaacagaccg ttggggtatc    2160
actgctgcct cttccagaac cctcagtgca gatacaccca ccgaagcagc gcaaagtgca    2220
cttctcagag gggacgcgga aaagaaagga gaggaaaccg aggaaaccgc gtcatcgtcc    2280
```

-continued

```
agtatcacga gtgccgaaag ctctactgag ggagatggat cgtctgatga tgaagagaca    2340
atcagacgca gaaggaggac ctggaagcga ctcagacgga tggtcagaca gcagcttgac    2400
cgacgaatgg accacaagcg acagcgactt cattgatacc cccataagag aaagatgcct    2460
caataaaaaa caaaaaaaac gctaaacagt gtccgcctat tagtgggggg gtccggggg    2520 gcttgccccc ccgtaagcgg ggttaccgca ctaactccct gccaagtgaa actcggggac    2580
gagtgagtgc gggacatccc gtgtaatggc tacataacta cccggctttg cttcgacagt    2640
ggccgtggct cgaccctcgc acaacactgc aggtaggggg cgcaattggg atcgttagaa    2700
aactatggcc gagcatgggg ggggctccgc cccccccaac cccccggtg ggggggccaa    2760 ggccctccct acaccccccc atgggggggct gccgccccc aaaccccccg cgtcggatgg    2820 gggggggctgc gccccccca aaccccccctt gcccggggct gtgccccgga ccccc        2875
```

<210> SEQ ID NO 12
<211> LENGTH: 635
<212> TYPE: PRT
<213> ORGANISM: Torque teno sus virus

<400> SEQUENCE: 12

```
Met Arg Phe Arg Arg Arg Phe Gly Arg Arg Arg Tyr Tyr Arg
  1               5                  10                  15

Lys Arg Arg Gly Gly Trp Arg Arg Phe Arg Ile Arg Arg Arg
             20                  25                  30

Pro Trp Arg Arg Trp Arg Val Arg Arg Trp Arg Arg Ser Val Phe Arg
         35                  40                  45

Arg Gly Gly Arg Arg Ala Arg Pro Tyr Arg Ile Ser Ala Trp Asn Pro
     50                  55                  60

Lys Val Leu Arg Asn Cys Arg Ile Thr Gly Trp Trp Pro Val Ile Gln
 65                  70                  75                  80

Cys Met Asp Gly Met Glu Trp Ile Lys Tyr Lys Pro Met Asp Leu Arg
                 85                  90                  95

Val Glu Ala Asn Trp Ile Phe Asn Lys Gln Asp Ser Lys Ile Glu Thr
            100                 105                 110

Glu Gln Met Gly Tyr Leu Met Gln Tyr Gly Gly Gly Trp Ser Ser Gly
        115                 120                 125

Val Ile Ser Leu Glu Gly Leu Phe Asn Glu Asn Arg Leu Trp Arg Asn
    130                 135                 140

Ile Trp Ser Lys Ser Asn Asp Gly Met Asp Leu Val Arg Tyr Phe Gly
145                 150                 155                 160

Cys Arg Ile Arg Leu Tyr Pro Thr Glu Asn Gln Asp Tyr Leu Phe Trp
                165                 170                 175

Tyr Asp Thr Glu Phe Asp Glu Gln Gln Arg Arg Met Leu Asp Glu Tyr
            180                 185                 190

Thr Gln Pro Ser Val Met Leu Gln Ala Lys Asn Ser Arg Leu Ile Val
        195                 200                 205

Cys Lys Gln Lys Met Pro Ile Arg Arg Val Lys Ser Ile Phe Ile
    210                 215                 220

Pro Pro Pro Ala Gln Leu Thr Thr Gln Trp Lys Phe Gln Glu Leu
225                 230                 235                 240

Cys Gln Phe Pro Leu Phe Asn Trp Ala Cys Ile Cys Ile Asp Met Asp
                245                 250                 255

Thr Pro Phe Asp Tyr Asn Gly Ala Trp Arg Asn Ala Trp Leu Met
            260                 265                 270
```

Arg Arg Leu Gln Asn Gly Asn Met Glu Tyr Ile Glu Arg Trp Gly Arg
            275                 280                 285

Ile Pro Met Thr Gly Asp Thr Glu Leu Pro Ala Asp Asp Phe Lys
290                 295                 300

Ala Gly Gly Val Asn Lys Asn Phe Lys Pro Thr Gly Ile Gln Arg Ile
305                 310                 315                 320

Tyr Pro Ile Val Ala Val Cys Leu Val Glu Gly Asn Lys Arg Val Val
                325                 330                 335

Lys Trp Ala Thr Val His Asn Gly Pro Ile Asp Arg Trp Arg Lys Lys
            340                 345                 350

Gln Thr Gly Thr Leu Lys Leu Ser Asn Leu Arg Gly Leu Val Leu Arg
        355                 360                 365

Val Cys Ser Glu Ser Glu Thr Tyr Tyr Lys Trp Thr Gly Ser Glu Phe
    370                 375                 380

Thr Gly Ala Phe Gln Gln Asp Trp Trp Pro Val Gly Gly Thr Glu Tyr
385                 390                 395                 400

Pro Leu Cys Thr Ile Lys Met Asp Pro Glu Tyr Glu Asn Pro Thr Val
                405                 410                 415

Glu Val Trp Ser Trp Lys Ala Asn Ile Pro Thr Ser Gly Thr Leu Lys
            420                 425                 430

Asp Tyr Phe Gly Leu Ser Thr Gly Gln Gln Trp Lys Asp Thr Asp Phe
        435                 440                 445

Ala Arg Leu Gln Leu Pro Arg Ser Ser His Asn Val Asp Phe Gly His
    450                 455                 460

Lys Ala Arg Phe Gly Pro Phe Cys Val Lys Lys Pro Pro Val Glu Phe
465                 470                 475                 480

Arg Asp Thr Ala Pro Asn Pro Leu Asn Ile Trp Val Lys Tyr Thr Phe
                485                 490                 495

Tyr Phe Gln Phe Gly Met Tyr Gln Pro Pro Thr Gly Ile Gln Asp
            500                 505                 510

Pro Cys Thr Ser Asn Pro Thr Tyr Pro Val Arg Met Val Gly Ala Val
        515                 520                 525

Thr His Pro Lys Tyr Ala Gly Gln Gly Ile Thr Thr Gln Ile Gly
    530                 535                 540

Asp Gln Gly Ile Thr Ala Ala Ser Ile Arg Ala Ile Ser Ala Ala Pro
545                 550                 555                 560

Pro Asp Thr Tyr Thr Gln Ser Ala Phe Leu Lys Ala Pro Glu Thr Glu
                565                 570                 575

Lys Glu Glu Glu Arg Glu Ser Glu Thr Ser Phe Thr Ser Ala Glu Ser
            580                 585                 590

Ser Ser Glu Gly Asp Gly Ser Ser Asp Asp Gln Ala Glu Arg Arg Ala
        595                 600                 605

Ala Arg Lys Arg Val Ile Lys Leu Leu Leu Lys Arg Leu Ala Asp Arg
    610                 615                 620

Pro Val Asp Asn Lys Arg Arg Arg Phe Ser Glu
625                 630                 635

<210> SEQ ID NO 13
<211> LENGTH: 639
<212> TYPE: PRT
<213> ORGANISM: Torque teno sus virus

<400> SEQUENCE: 13

Met Ala Pro Thr Arg Arg Trp Arg Arg Phe Gly Arg Arg Arg
1               5                   10                  15

```
Arg Tyr Arg Lys Arg Arg Tyr Gly Trp Arg Arg Tyr Tyr Arg Tyr
            20                  25                  30

Arg Pro Arg Tyr Tyr Arg Arg Trp Leu Val Arg Arg Arg Arg
        35                  40                  45

Ser Val Tyr Arg Arg Gly Gly Arg Arg Ala Arg Pro Tyr Arg Ile Ser
    50                  55                  60

Ala Phe Asn Pro Lys Val Met Arg Arg Val Val Ile Arg Gly Trp Trp
65              70                  75                  80

Pro Ile Leu Gln Cys Leu Lys Gly Gln Glu Ser Leu Arg Tyr Arg Pro
                85                  90                  95

Leu Gln Trp Asp Thr Glu Lys Gln Trp Arg Val Lys Lys Asp Tyr Glu
            100                 105                 110

Asp Asn Tyr Gly Tyr Leu Val Gln Tyr Gly Gly Trp Gly Ser Gly
            115                 120                 125

Glu Val Thr Leu Glu Gly Leu Tyr Gln Glu His Leu Leu Trp Arg Asn
    130                 135                 140

Ser Trp Ser Lys Gly Asn Asp Gly Met Asp Leu Val Arg Tyr Phe Gly
145                 150                 155                 160

Cys Ile Val Tyr Leu Tyr Pro Leu Gln Asp Gln Asp Tyr Trp Phe Trp
                165                 170                 175

Trp Asp Thr Asp Phe Lys Glu Leu Tyr Ala Glu Ser Ile Lys Glu Tyr
            180                 185                 190

Ser Gln Pro Ser Val Met Met Ala Lys Arg Thr Arg Leu Val Ile
    195                 200                 205

Ala Arg Asp Arg Ala Pro His Arg Arg Val Arg Lys Ile Phe Ile
210                 215                 220

Pro Pro Pro Ser Arg Asp Thr Thr Gln Trp Gln Phe Gln Thr Asp Phe
225                 230                 235                 240

Cys Lys Arg Pro Leu Phe Thr Trp Ala Ala Gly Leu Ile Asp Met Gln
                245                 250                 255

Lys Pro Phe Asp Ala Asn Gly Ala Phe Arg Asn Ala Trp Trp Leu Glu
            260                 265                 270

Thr Arg Asn Asp Gln Gly Glu Met Lys Tyr Ile Glu Leu Trp Gly Arg
            275                 280                 285

Val Pro Pro Gln Gly Asp Thr Glu Leu Pro Lys Gln Ser Glu Phe Lys
    290                 295                 300

Lys Gly Asp Asn Asn Pro Asn Tyr Asn Ile Thr Glu Gly His Glu Lys
305                 310                 315                 320

Asn Ile Tyr Pro Ile Ile Tyr Val Asp Gln Lys Asp Gln Lys Thr
                325                 330                 335

Arg Lys Lys Tyr Cys Val Cys Tyr Asn Lys Thr Leu Asn Arg Trp Arg
            340                 345                 350

Lys Ala Gln Ala Ser Thr Leu Ala Ile Gly Asp Leu Gln Gly Leu Val
    355                 360                 365

Leu Arg Gln Leu Met Asn Gln Glu Met Thr Tyr Tyr Trp Lys Ser Gly
    370                 375                 380

Glu Phe Ser Ser Pro Phe Leu Gln Arg Trp Lys Gly Thr Arg Leu Ile
385                 390                 395                 400

Thr Ile Asp Ala Arg Lys Ala Asp Thr Glu Asn Pro Lys Val Ser Ser
                405                 410                 415

Trp Glu Trp Gly Gln Asn Trp Asn Thr Ser Gly Thr Val Leu Gln Glu
            420                 425                 430
```

-continued

```
Val Phe Asn Ile Ser Leu Asn Asn Thr Gln Ile Arg Gln Asp Asp Phe
            435                 440                 445

Ala Lys Leu Thr Leu Pro Lys Ser Pro His Asp Ile Asp Phe Gly His
    450                 455                 460

His Ser Arg Phe Gly Pro Phe Cys Val Lys Asn Glu Pro Leu Glu Phe
465                 470                 475                 480

Gln Leu Leu Pro Pro Thr Pro Thr Asn Leu Trp Phe Gln Tyr Lys Phe
                485                 490                 495

Leu Phe Gln Phe Gly Gly Glu Tyr Gln Pro Pro Thr Gly Ile Arg Asp
                500                 505                 510

Pro Cys Ile Asp Thr Pro Ala Tyr Pro Val Pro Gln Ser Gly Ser Val
            515                 520                 525

Thr His Pro Lys Phe Ala Gly Lys Gly Gly Met Leu Thr Glu Thr Asp
            530                 535                 540

Arg Trp Gly Ile Thr Ala Ala Ser Ser Arg Thr Leu Ser Ala Asp Thr
545                 550                 555                 560

Pro Thr Glu Ala Ala Gln Ser Ala Leu Leu Arg Gly Asp Ala Glu Lys
                565                 570                 575

Lys Gly Glu Glu Thr Glu Glu Thr Ala Ser Ser Ser Ser Ile Thr Ser
                580                 585                 590

Ala Glu Ser Ser Thr Glu Gly Asp Gly Ser Ser Asp Asp Glu Glu Thr
                595                 600                 605

Ile Arg Arg Arg Arg Thr Trp Lys Arg Leu Arg Arg Met Val Arg
            610                 615                 620

Gln Gln Leu Asp Arg Arg Met Asp His Lys Arg Gln Arg Leu His
625                 630                 635
```